United States Patent
Huang et al.

(10) Patent No.: US 11,013,723 B1
(45) Date of Patent: May 25, 2021

(54) SOLID FORMS OF A THIAZOLIDINONE COMPOUND, COMPOSITIONS AND METHODS OF USE THEREOF

(71) Applicant: Celgene Corporation, Summit, NJ (US)

(72) Inventors: Lianfeng Huang, Basking Ridge, NJ (US); Daozhong Zou, Raritan, NJ (US)

(73) Assignee: CELGENE CORPORATION, Summit, NJ (US)

( * ) Notice: Subject to any disclaimer, the term of this patent is extended or adjusted under 35 U.S.C. 154(b) by 0 days.

(21) Appl. No.: 16/653,173

(22) Filed: Oct. 15, 2019

Related U.S. Application Data

(60) Provisional application No. 62/746,439, filed on Oct. 16, 2018.

(51) Int. Cl.
| | | |
|---|---|---|
| *A61K 31/426* | (2006.01) | |
| *C07D 277/54* | (2006.01) | |
| *A61K 47/22* | (2006.01) | |
| *A61K 45/06* | (2006.01) | |
| *C07D 207/16* | (2006.01) | |

(52) U.S. Cl.
CPC ............ *A61K 31/426* (2013.01); *A61K 45/06* (2013.01); *A61K 47/22* (2013.01); *C07D 207/16* (2013.01); *C07D 277/54* (2013.01); *C07B 2200/13* (2013.01)

(58) Field of Classification Search
None
See application file for complete search history.

(56) References Cited

U.S. PATENT DOCUMENTS

| | | |
|---|---|---|
| 7,435,828 B2 | 10/2008 | Binkert et al. |
| 8,263,780 B2 | 9/2012 | Abele et al. |
| 8,273,779 B2 | 9/2012 | Binkert et al. |
| RE43,728 E | 10/2012 | Binkert et al. |
| 8,399,514 B2 | 3/2013 | Lukashev et al. |
| 8,524,752 B2 | 9/2013 | Binkert et al. |
| 8,785,484 B2 | 7/2014 | Brossard et al. |
| 8,912,340 B2 | 12/2014 | Abele et al. |
| 9,000,018 B2 | 4/2015 | Binkert et al. |
| 9,062,014 B2 | 6/2015 | Bonham et al. |
| 9,340,518 B2 | 5/2016 | Herse |
| 2007/0134803 A1* | 6/2007 | Blatter ................ B01J 19/0046 436/96 |
| 2014/0303217 A1 | 10/2014 | Brossard et al. |
| 2014/0316140 A1 | 10/2014 | Brossard et al. |

FOREIGN PATENT DOCUMENTS

| | | |
|---|---|---|
| EP | 2 316 430 B1 | 6/2012 |
| WO | WO 2005/054215 A1 | 6/2005 |
| WO | WO 2005/123677 A1 | 12/2005 |
| WO | WO 2006/010379 A1 | 2/2006 |
| WO | WO 2006/010544 A2 | 2/2006 |
| WO | WO 2006/100633 A1 | 9/2006 |
| WO | WO 2006/100635 A2 | 9/2006 |
| WO | WO 2007/080542 A1 | 7/2007 |
| WO | WO 2008/029306 A2 | 3/2008 |
| WO | WO 2008/062376 A2 | 5/2008 |
| WO | WO 2008/097596 A2 | 8/2008 |
| WO | WO 2008/114157 A1 | 9/2008 |
| WO | WO 2009/024905 A1 | 2/2009 |
| WO | WO 2009/074950 A2 | 6/2009 |
| WO | WO 2009/115954 A1 | 9/2009 |
| WO | WO 2010/046835 A1 | 4/2010 |
| WO | WO 2011/007324 A1 | 1/2011 |
| WO | WO 2013/184888 A1 | 12/2013 |
| WO | WO 2014/027330 A1 | 2/2014 |
| WO | WO 2016/091996 A1 | 6/2016 |
| WO | WO 2016/092042 A1 | 6/2016 |
| WO | WO 2017/107972 A1 | 6/2017 |
| WO | WO 2018/167030 A1 | 9/2018 |
| WO | WO 2019/060147 A1 | 3/2019 |

OTHER PUBLICATIONS

Background Information for the October ACPS Meeting, FDA, 2002.*
B. Rodriquez-Spong et al. Advanced Drug Delivery Reviews, 2004, 56, pp. 241-274.*
Hilfiker, R. Polymorphism in the Pharmaceutical Industry, Wiley, 2006, 213-216.*
Boehler et al., "Absolute Bioavailability of Ponesimod, a Selective S1P 1 Receptor Modulator, in Healthy Male Subjects," *Eur J Drug Metab Pharmacokinet.*, 42(1):129-134 (2017).
Bolli et al., "2-imino-thiazolidin-4-one Derivatives as Potent, Orally Active S1P1 Receptor Agonists," J Med Chem.;53(10):4198-4211 (2010).
Brossard et al., "Multiple-dose Tolerability, Pharmacokinetics, and Pharmacodynamics of Ponesimod, an S1P1 Receptor Modulator: Favorable Impact of Dose Up-Titration," *J. Clin. Pharmacol.*, 54(2):179-188 (2014).
D'Ambrosio et al., *Immunopharmacol Immunotoxicol.* 37(1):103-109. (2015).
D'Ambrosio et al., "Ponesimod, a Selective S1P1 Receptor Modulator: A Potential Treatment for Multiple Sclerosis and Other Immune-Mediated Diseases," *Ther. Adv. Chronic. Dis.*, 7(1):18-33 (2016).
Guerard et al., "Effect of Hepatic or Renal Impairment on the Pharmacokinetics, Safety, and Tolerability of Ponesimod, a Selective S1P1 Receptor Modulator," *Basic Clin. Pharmacol. Toxicol.*, 118(5):356-368 (2016).
Hoch et al., "Effect of Ponesimod, a Selective S1P1 Receptor Modulator, on the QT Interval in Healthy Individuals," *Basic Clin. Pharmacol. Toxicol.*, 116(5): 429-437 (2015).
Hoch et al., "Clinical Pharmacology of Ponesimod, a Selective S1P$_1$ Receptor Modulator, After Uptitration to Supratherapeutic Doses in Healthy Subjects," *Eur. J. Pharm. Sci.*, 63:147-153 (2014).

(Continued)

*Primary Examiner* — Samantha L Shterengarts
(74) *Attorney, Agent, or Firm* — Jones Day

(57) ABSTRACT

Provided herein are formulations, processes, solid forms and methods of use relating to (Z)-5-((Z)-3-chloro-4-((R)-2,3-dihydroxypropoxy)benzylidene)-2-(propylimino)-3-(o-tolyl)thiazolidin-4-one.

30 Claims, 24 Drawing Sheets

(56) References Cited

OTHER PUBLICATIONS

Juif et al., "Biocomparison of three formulations of the SIP receptor modulator ponesimod in healthy subjects," *Drugs R D.* 15(2):203-210 (2015).

Juif et al., "Clinical Pharmacology, Efficacy, and Safety Aspects of sphingosine-1-phosphate Receptor Modulators,"*Expert Opin Drug Metab Toxicol.* 12(8):879-895 (2016).

Juif et al., "Mitigation of Initial Cardiodynamic Effects of the S1P 1 Receptor Modulator Ponesimod Using a Novel Up-Titration Regimen," *J. Clin. Pharmacol.,* 57(3):401-410 (2017).

Jurcevic et al., "Effects of Multiple-Dose Ponesimod, a Selective S1P 1 Receptor Modulator, on Lymphocyte Subsets in Healthy Humans," *Drug Des. Devel Ther.,* 11:123-131 (2016).

Krause et al., "Population Pharmacokinetics and Pharmacodynamics of Ponesimod, a Selective S1P1 Receptor Modulator," *J Pharmacokinet Pharmacodyn.,* 41(3):261-278 (2014).

Lott et al., "Impact of Demographics, Organ Impairment, Disease, Formulation, and Food on the Pharmacokinetics of the Selective S1P 1 Receptor Modulator Ponesimod Based on 13 Clinical Studies," *Clin. Pharmacokinet.,* 56(4):395-408 (2017).

Lott et al., "Population Pharmacokinetics of Ponesimod and its Primary Metabolites in Healthy and Organ-Impaired Subjects," *Eur J Pharm Sci.,*89:83-93 (2016).

Lott et al., Pharm Res.;34(3):599-609 (2017).

NCT01006265: Clinical Study to Evaluate the Efficacy, Safety, and Tolerability of ACT-128800 in Patients With Relapsing-remitting Multiple Sclerosis. https://clinicaltrials.gov/ct2/show/NCT01006265. First posted Nov. 1, 2009; last update posted Apr. 4, 2017; downloaded May 28, 2020.

NCT01093326: Clinical Study to Investigate the Long-term Safety, Tolerability, and Efficacy of Ponesimod in Patients With Relapsing-remitting Multiple Sclerosis. https://clinicaltrials.gov/ct2/show/NCT01093326?term=NCT01093326&draw=2&rank=1. Fist posted Mar. 25, 2010; last updated posted May 21, 2020; downloaded May 28, 2020.

NCT01755871: Long-term Effect of Fingolimod on Circulating Immunocompetent Mononuclear Cells in Patients With Multiple Sclerosis (terminated). https://clinicaltrials.gov/ct2/show/NCT01755871?term=NCT01755871&draw=2&rank=1. First posted Dec. 24, 2012; Last Update Posted Jun. 9, 2016; downloaded May 28, 2020.

NCT02029482: Study to Investigate the Safety, Tolerability, Pharmacokinetics, and Pharmacodynamics of ACT-128800 in Healthy Subjects. https://clinicaltrials.gov/ct2/show/NCT02029482?term=NCT02029482&draw=2&rank=1. First Posted Jan. 8, 2014; Last Update Posted Jan. 8, 2014; downloaded May 28, 2020.

NCT02068235: Study to Investigate the Absolute Bioavailability of a Single Oral Dose of Ponesimod in Healthy Male Subjects. https://clinicaltrials.gov/ct2/show/NCT02068235?term=NCT02068235&draw=2&rank=1. First Posted Feb. 21, 2014; Last Update Posted May 21, 2015; downloaded May 28, 2020.

NCT02126956: Mass Balance, Pharmacokinetics, and Metabolism of 14C-labeled ACT-128800 Administered to Healthy Male Subjects. https://clinicaltrials.gov/ct2/show/NCT02126956?term=NCT02126956&draw=2&rank=1. First Posted Apr. 30, 2014; Late Update Posted Apr. 30, 2014; downloaded May 28, 2020.

NCT02136888: Study of the Electrocardiographic Effects of Ponesimod in Healthy Male and Female Subjects. https://clinicaltrials.gov/ct2/show/NCT02136888?term=NCT02136888&draw=2&rank=1. First Posted May 13, 2014; Last Update Posted May 13, 2014; downloaded May 28, 2020.

NCT02223832: Study to Evaluate the Pharmacokinetics, Tolerability, and Safety of ACT-128800 in Japanese and Caucasian Healthy Male and Female Subjects. https://clinicaltrials.gov/ct2/show/NCT02223832?term=NCT02223832&draw=2&rank=1. First Posted Aug. 22, 2014; Last Update Posted Aug. 22, 2014; downloaded May 22, 2020.

NCT02425644: Oral Ponesimod Versus Teriflunomide in Relapsing MUltiple Sclerosis (OPTIMUM). https://clinicaltrials.gov/ct2/show/NCT02425644?term=NCT02425644&draw=2&rank=1. First Posted Apr. 24, 2015; Last Update Posted May 27, 2020; downloaded May 28, 2020.

NCT02461134: Clinical Study to Investigate the Biological Activity, Safety, Tolerability, and Pharmacokinetics of Ponesimod in Subjects With Symptomatic Chronic GVHD (terminated). https://clinicaltrials.gov/ct2/show/NCT02461134?term=NCT02461134&draw=2&rank=1. First Posted Jun. 3, 2015; Last Update Posted May 9, 2018; downloaded May 28, 2020.

NCT02907177: Clinical Study to Compare the Efficacy and Safety of Ponesimod to Placebo in Subjects With Active Relapsing Multiple Sclerosis Who are Treated With Dimethyl Fumarate (Tecfidera®). https://clinicaltrials.gov/ct2/show/NCT02907177?term=NCT02907177&draw=2&rank=1. First Posted Sep. 20, 2016; Last Update Posted Apr. 6, 2020; downloaded May 28, 2020.

Olsson et al., "Oral Ponesimod in Relapsing-Remitting Multiple Sclerosis: A Randomised Phase II Trial," *Neuro.l Neurosurg. Psychiatry.,* 85(11):1198-1208 (2014).

Piali et al., "The Selective Sphingosine 1-phosphate Receptor 1 Agonist Ponesimod Protects Against Lymphocyte-Mediated Tissue Inflammation," *J. Pharmacol. Exp. Ther.,* 337(2):547-556 (2011).

Rey et al., "Desensitization by Progressive Up-Titration Prevents First-Dose Effects on the Heart: Guinea Pig Study With Ponesimod, a Selective S1P1 Receptor Modulator," *PLoS One.,* 8(9):e74285 (2013).

Reyes et al., "Effects of Ethnicity and Sex on the Pharmacokinetics and Pharmacodynamics of the Selective sphingosine-1-phosphate Receptor 1 Modulator Ponesimod: A Clinical Study in Japanese and Caucasian Subjects," *Pharmacology,* 94(5-6): 223-229 (2014).

Reyes et al., "Mass Balance, Pharmacokinetics and Metabolism of the Selective S1P1 Receptor Modulator Ponesimod in Humans," *Xenobiotica.,* 45(2):139-149 (2015).

Scherz et al. "Three Different Up-Titration Regimens of Ponesimod, an S1P1 Receptor Modulator, in Healthy Subjects," *J. Clin. Pharmacol.,* 55(6):688-697 (2015).

\* cited by examiner

SOLID FORMS OF A THIAZOLIDINONE COMPOUND, COMPOSITIONS AND METHODS OF USE THEREOF

This application claims priority to U.S. Provisional Application No. 62/746,439, filed Oct. 16, 2018, the entirety of which is incorporated herein by reference.

1. FIELD

Provided herein are solid forms, including co-crystals of (Z)-5-((Z)-3-chloro-4-((R)-2,3-dihydroxypropoxy)benzylidene)-2-(propylimino)-3-(o-tolyl)thiazolidin-4-one. Pharmaceutical compositions and formulations comprising such solid forms and co-crystals and methods of use of the same for treating, preventing, and managing various disorders are also provided herein.

2. BACKGROUND

When the immune system functions normally, it produces a response intended to protect against harmful or foreign substances such as bacteria, parasites, and cancerous cells. Autoimmune diseases arise when the immune system attacks one or more of the body's normal constituents as if they were a foreign substance. These attacks cause inflammation and tissue damage that may lead to autoimmune disorders. There are more than 80 diseases that occur as a result of the body's autoimmune response to various harmful or foreign substances, affecting more than 23.5 million people in the United States. Some of the most common types of autoimmune diseases include multiple sclerosis, and psoriasis.

Multiple Sclerosis ("MS") is an autoimmune disease of the central nervous system, characterized by degeneration of the protective sheath ("myelin") that covers nerve fibers in the brain and spinal cord. More than 2.5 million people in the world suffer from MS, and it is the most common neurologic, disabling disease in young adults. Diagnosis is generally made between 15 and 50 years of age, with symptoms either occurring in recurring, isolated attacks (i.e., relapsing forms) or symptoms increasing over time (i.e., progressive forms). Permanent neurological dysfunction can result from incomplete recovery from acute relapses or as a consequence of slow progression of disability.

There is a need in the art for novel drug products for the treatment of MS and other autoimmune diseases of the central nervous systems. In recent years, pharmaceutical co-crystals have emerged as a possible alternative approach to modulate or enhance the physical and chemical properties of drug products. Co-crystals are crystalline solids composed of two or more different compounds bound together in a crystal lattice. Pharmaceutical co-crystals are co-crystals of a therapeutic compound, e.g., an active pharmaceutical ingredient ("API"), and one or more non-volatile compound(s) (referred to herein as coformer). A coformer in a pharmaceutical co-crystal is typically a non-toxic pharmaceutically acceptable molecule.

Notably, it is not possible to predict a priori if crystalline forms of a compound even exist, let alone how to successfully prepare them (see, e.g., Braga and Grepioni, 2005, "Making crystals from crystals: a green route to crystal engineering and polymorphism," *Chem. Commun.*: 3635-3645 (with respect to crystal engineering, if instructions are not very precise and/or if other external factors affect the process, the result can be unpredictable); Jones et al., 2006, Pharmaceutical Co-crystals: An Emerging Approach to Physical Property Enhancement," *MRS Bulletin* 31: 875-879 (at present it is not generally possible to computationally predict the number of observable polymorphs of even the simplest molecules); Price, 2004, "The computational prediction of pharmaceutical crystal structures and polymorphism," *Advanced Drug Delivery Reviews* 56: 301-319 ("Price"); and Bernstein, 2004, "Crystal Structure Prediction and Polymorphism," *ACA Transactions* 39: 14-23 (a great deal still needs to be learned and done before one can state with any degree of confidence the ability to predict a crystal structure, much less polymorphic forms)).

The variety of possible solid forms creates potential diversity in physical and chemical properties for a given pharmaceutical compound. The discovery and selection of solid forms are of great importance in the development of an effective, stable and marketable pharmaceutical product.

3. SUMMARY

Provided herein are solid forms, including co-crystals of Compound 1:

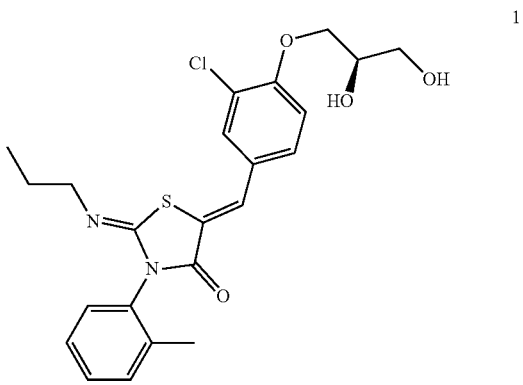 [SMILES: CCC/N=C1\S/C(=C\c2ccc(OC[C@H](O)CO)c(Cl)c2)C(=O)N1c1ccccc1C]

having the chemical name (Z)-5-((Z)-3-chloro-4-((R)-2,3-dihydroxypropoxy)benzylidene)-2-(propylimino)-3-(o-tolyl)thiazolidin-4-one (also known as ponesimod). The solid forms, including co-crystals, also include solid forms comprising a tautomer of Compound 1. Also provided herein are methods of preparing, isolating, and characterizing the solid forms.

In certain embodiments, provided herein is a co-crystal comprising (a) Compound 1 and (b) a coformer. In certain embodiments, the coformer is selected from the group consisting of L-prolinamide, pyrogallol, aspartame, citric acid, nicotinamide, 1-hydroxy-2-naphthoic acid, L-malic acid, urea, quercetin, camphoric acid, and L-mandelic acid.

In certain embodiments, provided herein is a pharmaceutical composition comprising (1) a co-crystal comprising (a) Compound 1 and (b) a coformer; and (2) a pharmaceutically acceptable excipient or carrier.

In certain embodiments, provided herein is a solid form comprising (a) Compound 1 and (b) a second compound selected from the group consisting of L-prolinamide, pyrogallol, aspartame, citric acid, nicotinamide, 1-hydroxy-2-naphthoic acid, L-malic acid, urea, quercetin, camphoric acid, and L-mandelic acid.

In certain embodiments, provided herein is a pharmaceutical composition comprising (1) a solid form comprising (a) Compound 1 and (b) a second compound; and (2) a pharmaceutically acceptable excipient or carrier.

In certain embodiments, provided herein is a method of treating multiple sclerosis comprising administering to a patient in need thereof a co-crystal comprising (a) Compound 1 and (b) a coformer. In certain embodiments, the coformer is selected from the group consisting of L-prolinamide, pyrogallol, aspartame, citric acid, nicotinamide, 1-hydroxy-2-naphthoic acid, L-malic acid, urea, quercetin, camphoric acid, and L-mandelic acid.

In certain embodiments, provided herein is a method of treating multiple sclerosis comprising administering to a patient in need thereof a solid form comprising (a) Compound 1 and (b) a second compound. In certain embodiments, the second compound is selected from the group consisting of L-prolinamide, pyrogallol, aspartame, citric acid, nicotinamide, 1-hydroxy-2-naphthoic acid, L-malic acid, urea, quercetin, camphoric acid, and L-mandelic acid.

In certain embodiments, provided herein is a method of treating multiple sclerosis comprising administering to a patient in need thereof a pharmaceutical composition comprising (1) a co-crystal comprising (a) Compound 1 and (b) a coformer; and (2) a pharmaceutically acceptable excipient or carrier.

In certain embodiments, provided herein is a method of treating multiple sclerosis comprising administering to a patient in need thereof a pharmaceutical composition comprising (1) solid form comprising (a) Compound 1 and (b) a second compound; and (2) a pharmaceutically acceptable excipient or carrier.

In certain embodiments, provided herein is a method of treating psoriasis comprising administering to a patient in need thereof a co-crystal comprising (a) Compound 1 and (b) a coformer. In certain embodiments, the coformer is selected from the group consisting of L-prolinamide, pyrogallol, aspartame, citric acid, nicotinamide, 1-hydroxy-2-naphthoic acid, L-malic acid, urea, quercetin, camphoric acid, and L-mandelic acid.

In certain embodiments, provided herein is a method of treating psoriasis comprising administering to a patient in need thereof a solid form comprising (a) Compound 1 and (b) a second compound. In certain embodiments, the second compound is selected from the group consisting of L-prolinamide, pyrogallol, aspartame, citric acid, nicotinamide, 1-hydroxy-2-naphthoic acid, L-malic acid, urea, quercetin, camphoric acid, and L-mandelic acid.

In certain embodiments, provided herein is a method of treating psoriasis comprising administering to a patient in need thereof a pharmaceutical composition comprising (1) a co-crystal comprising (a) Compound 1 and (b) a coformer; and (2) a pharmaceutically acceptable excipient or carrier.

In certain embodiments, provided herein is a method of treating psoriasis comprising administering to a patient in need thereof a pharmaceutical composition comprising (1) solid form comprising (a) Compound 1 and (b) a second compound; and (2) a pharmaceutically acceptable excipient or carrier.

4. BRIEF DESCRIPTION OF THE DRAWINGS

5. DETAILED DESCRIPTION

5.1 Definitions

Figure 1:
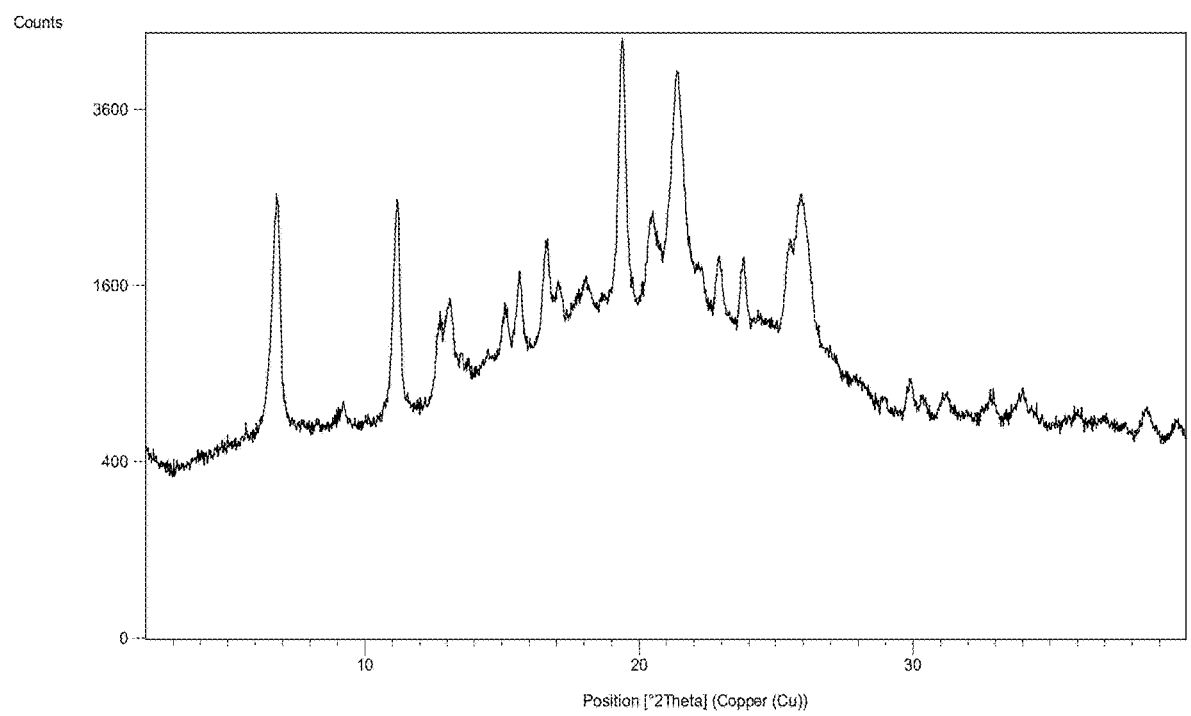
FIG. 1 depicts a representative X-ray powder diffraction (PXRD) pattern of co-crystal Form 1 of Compound 1.

As used herein, and unless otherwise specified, the terms "about" and "approximately," when used in connection with doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. In certain embodiments, the terms "about" and "approximately," when used in this context, contemplate a dose, amount, or weight percent within 30%, within 20%, within 15%, within 10%, or within 5%, of the specified dose, amount, or weight percent.

As used herein, and unless otherwise specified, the terms "about" and "approximately," when used in connection with a numeric value or range of values which is provided to characterize a particular solid form, e.g., a specific temperature or temperature range, such as, for example, that describes a melting, dehydration, desolvation, or glass transition temperature; a mass change, such as, for example, a mass change as a function of temperature or humidity; a solvent or water content, in terms of, for example, mass or a percentage; or a peak position, such as, for example, in analysis by, for example, infrared (IR) or Raman spectroscopy or X-ray powder diffractometry (PXRD); indicate that the value or range of values may deviate to an extent deemed reasonable to one of ordinary skill in the art while still describing the solid form. If the term "approximately" is followed by a series of PXRD peak positions, the term applies equally to each of the peak positions. Techniques for characterizing crystal forms and amorphous forms include, but are not limited to, thermal gravimetric analysis (TGA), differential scanning calorimetry (DSC), PXRD, single-crystal X-ray diffractometry, vibrational spectroscopy, e.g., IR and Raman spectroscopy, solid-state and solution nuclear magnetic resonance (NMR) spectroscopy, polarized light microscopy (PLM), optical microscopy, hot stage optical microscopy, scanning electron microscopy (SEM), electron crystallography and quantitative analysis, particle size analysis (PSA), surface area analysis, solubility studies, and dissolution studies. In certain embodiments, the terms "about" and "approximately," when used in this context, indicate that the numeric value or range of values may vary within 30%, 20%, 15%, 10%, 9%, 8%, 7%, 6%, 5%, 4%, 3%, 2%, 1.5%, 1%, 0.5%, or 0.25% of the recited value or range of values. For example, in some embodiments, the value of a PXRD peak position may vary by up to ±0.2 2θ while still describing the particular PXRD peak.

As used herein, and unless otherwise specified, a crystalline that is "pure," i.e., substantially free of other crystalline or amorphous forms, contains less than about 10% by weight of one or more other crystalline or amorphous forms, less than about 5% by weight of one or more other crystalline or amorphous forms, less than about 3% by weight of one or more other crystalline or amorphous forms, or less than about 1% by weight of one or more other crystalline or amorphous forms.

As used herein and unless otherwise indicated, the term "substantially pure" when used to describe a solid form of a compound, i.e., a crystal form or an amorphous form of a compound, means a crystal form or an amorphous form of the compound that comprises that crystal form or amorphous form and is substantially free of other solid forms of the compound. A substantially pure crystal form is no less than about 95% pure, no less than about 96% pure, no less than about 97% pure, no less than about 98% pure, no less than about 98.5% pure, no less than about 99% pure, no less than about 99.5% pure, or no less than about 99.8% pure. In certain embodiments, a form that is substantially pure contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more other polymorphs on a weight basis.

As used herein, and unless otherwise specified, a solid form that is "substantially chemically pure" is substantially free from other chemical compounds (i.e., chemical impurities). In certain embodiments, a solid form that is substantially chemically pure contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more other chemical compounds on a weight basis. The detection of other chemical compounds can be accomplished by any method apparent to a person of ordinary skill in the art, including, but not limited to, methods of chemical analysis, such as, e.g., mass spectrometry analysis, spectroscopic analysis, thermal analysis, elemental combustion analysis and/or chromatographic analysis.

As used herein, and unless otherwise indicated, a chemical compound, solid form, or composition that is "substantially free" of another chemical compound, solid form, or composition means that the compound, solid form, or composition contains, in certain embodiments, less than about 10%, 9%, 8%, 7%, 6%, 5%, 4%, 3%, 2%, 1%, 0.5%, 0.4%, 0.3%, 0.2%, 0.1%, 0.05%, or 0.01% by weight of the other compound, solid form, or composition.

As used herein, and unless otherwise indicated, the terms "solvate" and "solvated" refer to a solid form of a substance which contains solvent. The terms "solvate" and "solvated," as used herein, can also refer to a solvate of a salt, co-crystal, or molecular complex.

As used herein, and unless otherwise indicated, the terms "hydrate" and "hydrated" refer to a solvate wherein the solvent is water. The terms "hydrate" and "hydrated," as used herein, can also refer to a hydrate of a salt, co-crystal, or molecular complex.

As used herein, and unless otherwise indicated, the term "composition" is intended to encompass a product comprising the specified ingredient(s) (and in the specified amount(s), if indicated), as well as any product which results, directly or indirectly, from combination of the specified ingredient(s) in the specified amount(s). By "pharmaceutically acceptable," as used herein, it is meant a diluent, excipient, or carrier in a formulation must be compatible with the other ingredient(s) of the formulation and not deleterious to the recipient thereof.

As used herein, and unless otherwise indicated, the term "solid form" refers to a physical form which is not predominantly in a liquid or a gaseous state. The term "solid form," when used herein to refer to Compound 1, refers to a physical form comprising Compound 1 which is not predominantly in a liquid or a gaseous state. A solid form may be a crystalline form or a mixture thereof. In certain embodiments, a solid form may be a liquid crystal. In certain embodiments, the term "solid forms comprising Compound 1" includes crystal forms comprising Compound 1. In certain embodiments, a solid form may be a co-crystal, e.g., a co-crystal of Compound 1.

As used herein and unless otherwise specified, the term "crystalline" when used to describe a compound, substance, modification, material, component or product, unless otherwise specified, means that the compound, substance, modification, material, component or product is substantially crystalline as determined by X-ray diffraction. See, e.g., Remington: The Science and Practice of Pharmacy, 21st edition, Lippincott, Williams and Wilkins, Baltimore, Md. (2005); The United States Pharmacopeia, $23^{rd}$ ed., 1843-1844 (1995).

As used herein, and unless otherwise indicated, the term "crystal form" or "crystalline form" refers to a solid form that is crystalline. In certain embodiments, crystal forms include salts. In certain embodiments, a crystal form of a substance may be substantially free of amorphous forms and/or other crystal forms. In certain embodiments, a crystal form of a substance may contain less than about 1%, less than about 2%, less than about 3%, less than about 4%, less than about 5%, less than about 6%, less than about 7%, less than about 8%, less than about 9%, less than about 10%, less than about 15%, less than about 20%, less than about 25%, less than about 30%, less than about 35%, less than about 40%, less than about 45%, or less than about 50% by weight of one or more amorphous forms and/or other crystal forms. In certain embodiments, a crystal form of a substance may be physically and/or chemically pure. In certain embodiments, a crystal form of a substance may be about 99%, about 98%, about 97%, about 96%, about 95%, about 94%, about 93%, about 92%, about 91%, or about 90% physically and/or chemically pure.

As used herein, and unless otherwise indicated, the term "co-crystal" refers to a crystalline material comprised of a compound (e.g., Compound 1) and one or more non-volatile compounds in a defined stoichiometric ratio. As used herein, and unless otherwise indicated, the term "coformer" refers to the one or more non-volatile compounds bound with the compound. In certain embodiments, the compound and the coformer are bound within the same crystal lattice. In certain embodiments, the co-crystal and the coformer are associated by nonionic and/or noncovalent interactions within the crystal lattice.

As used herein, and unless otherwise indicated, the term "amorphous" or "amorphous form" means that the substance, component, or product in question is not substantially crystalline as determined by X-ray diffraction. In particular, the term "amorphous form" describes a disordered solid form, i.e., a solid form lacking long range crystalline order. In certain embodiments, an amorphous form of a substance may be substantially free of other amorphous forms and/or crystal forms. In certain embodiments, an amorphous form of a substance may contain less than about 1%, less than about 2%, less than about 3%, less than about 4%, less than about 5%, less than about 10%, less than about 15%, less than about 20%, less than about 25%, less than about 30%, less than about 35%, less than about 40%, less than about 45%, or less than about 50% by weight of one or more other amorphous forms and/or crystal forms on a weight basis. In certain embodiments, an amorphous form of a substance may be physically and/or chemically pure. In certain embodiments, an amorphous form of a substance be about 99%, about 98%, about 97%, about 96%, about 95%, about 94%, about 93%, about 92%, about 91%, or about 90% physically and/or chemically pure.

As used herein, and unless otherwise indicated, the term "treating" means an alleviation, in whole or in part, of the disease or disorder, or symptoms associated with the disease or disorder, or slowing, or halting of further progression or worsening of the disease or disorder, or symptoms associated with the disease or disorder.

As used herein, and unless otherwise indicated, the term "preventing" means prevention of the onset, recurrence, or spread of the disease or disorder, or symptoms associated with the disorder or disease, in a patient at risk for developing the disease or disorder.

As used herein, and unless otherwise specified, the term "therapeutically effective amount" of a compound refers to an amount sufficient to provide a therapeutic benefit in the treatment or management of the disease or to delay or minimize one or more symptoms associated with the disease. Further, a therapeutically effective amount of a compound means that amount of therapeutic agent alone, or in combination with other therapies, provides a therapeutic benefit in the treatment or management of the disease. The term "therapeutically effective amount" can encompass an amount that improves overall therapy, reduces or avoids symptoms or causes of disease, or enhances the therapeutic efficacy of another therapeutic agent.

As used herein, and unless otherwise indicated, the term "subject" or "patient" includes an animal, including, but not limited to, an animal such a cow, monkey, horse, sheep, pig, chicken, turkey, quail, cat, dog, mouse, rat, rabbit or guinea pig, in one embodiment a mammal, in another embodiment a human. In one embodiment a subject may be a cell from any one of the foregoing animals. In one embodiment, a subject or patient is a non-human animal, in another embodiment a non-human mammal. In another embodiment, a subject or patient is a human having or at risk for having a disease associated with an activated immune system. In certain embodiments, the disease or disorder can be treated and/or prevented with a selective S1P1 receptor agonist. In certain embodiments, the disease or disorder is selected from the group consisting of rejection of transplanted organs or tissue; graft-versus-host diseases brought about by transplantation; autoimmune syndromes including rheumatoid arthritis; systemic lupus erythematosus; Hashimoto's thyroiditis; lymphocytic thyroiditis; multiple sclerosis; myasthenia gravis; type I diabetes; uveitis; posterior uveitis; uveitis associated with Behcet's disease; uveomeningitis syndrome; allergic encephalomyelitis; chronic allograft vasculopathy; post-infectious autoimmune diseases including rheumatic fever and post-infectious glomerulonephritis; inflammatory and hyperproliferative skin diseases; psoriasis; atopic dermatitis; osteomyelitis; contact dermatitis; eczematous dermatitis; seborrhoeic dermatitis; lichen planus; pemphigus; bullous pemphigoid; epidermolysis bullosa; urticaria; angioedema; vasculitis; erythema; cutaneous eosinophilia; acne; alopecia areata; keratoconjunctivitis; vernal conjunctivitis; keratitis; herpetic keratitis; dystrophia epithelialis corneae; corneal leukoma; ocular pemphigus; Mooren's ulcer; ulcerative keratitis; scleritis; Graves' ophthalmopathy; Vogt-Koyanagi-Harada syndrome; sarcoidosis; pollen allergies; reversible obstructive airway disease; bronchial asthma; allergic asthma; intrinsic asthma; extrinsic asthma; dust asthma; chronic or inveterate asthma; late asthma and airway hyper-responsiveness; bronchitis; gastric ulcers; ischemic bowel diseases; inflammatory bowel diseases; necrotizing enterocolitis; intestinal lesions associated with thermal burns; coeliac diseases; proctitis; eosinophilic gastroenteritis; mastocytosis; Crohn's disease; ulcerative colitis; vascular damage caused by ischemic diseases and thrombosis; atherosclerosis; fatty heart; myocarditis; cardiac infarction; arteriosclerosis; aortitis syndrome; cachexia due to viral disease; vascular thrombosis; migraine; rhinitis; eczema; interstitial nephritis; IgA-induced nephropathy; Goodpasture's syndrome; hemolytic-uremic syndrome; diabetic nephropathy; glomerulosclerosis; glomerulonephritis; multiple myositis; Guillain-Barre syndrome; Meniere's disease; polyneuritis; multiple neuritis; mononeuritis; radiculopathy; hyperthyroidism; Basedow's disease; thyrotoxicosis; pure red cell aplasia; aplastic anemia; hypoplastic anemia; idiopathic thrombocytopenic purpura; autoimmune hemolytic anemia; agranulocytosis; pernicious anemia; megaloblastic anemia; anerythroplasia; osteoporosis; sarcoidosis; fibroid lung; idiopathic interstitial pneumonia; dermatomyositis; leukoderma vulgaris; ichthyosis vulgaris; photoallergic sensitivity; cutaneous T cell lymphoma; polyarteritis nodosa; Huntington's chorea; Sydenham's chorea; myocardosis; scleroderma; Wegener's granuloma; Sjogren's syndrome; adiposis; eosinophilic fascitis; lesions of gingiva, periodontium, alveolar bone, substantia ossea dentis; male pattern alopecia or alopecia *senilis*; muscular dystrophy; pyoderma; Sezary's syndrome; chronic adrenal insufficiency; Addison's disease; ischemia-reperfusion injury of organs which occurs upon preservation; endotoxin shock; pseudomembranous colitis; colitis caused by drug or radiation; ischemic acute renal insufficiency; chronic renal insufficiency; lung cancer; malignancy of lymphoid origin; acute or chronic lymphocytic leukemias; lymphoma; psoriasis; pulmonary emphysema; cataracta; siderosis; retinitis pigmentosa; senile macular degeneration; vitreal scarring; corneal alkali burn; dermatitis erythema; ballous dermatitis; cement dermatitis; gingivitis; periodontitis; sepsis; pancreatitis; carcinogenesis; metastasis of carcinoma; hypobaropathy; autoimmune hepatitis; primary biliary cirrhosis; sclerosing cholangitis; partial liver resection; acute liver necrosis; cirrhosis; alcoholic cirrhosis; hepatic failure; fulminant hepatic failure; late-onset hepatic failure; "acute-on-chronic" liver failure.

As used herein, and unless otherwise indicated, the term "zwitterion(s)" means compound(s) containing both a basic moiety, including but not limited to, for example, pyridine and imidazole; and an acidic moiety including but not limited to, for example, a carboxylic acid.

Unless otherwise specified, to the extent that there is a discrepancy between a depicted chemical structure of a compound provided herein and a chemical name of a compound provided herein, the chemical structure shall control.

5.2 Compound 1

The co-crystals, compositions, formulations, and methods of use provided herein relate to co-crystals of Compound 1:

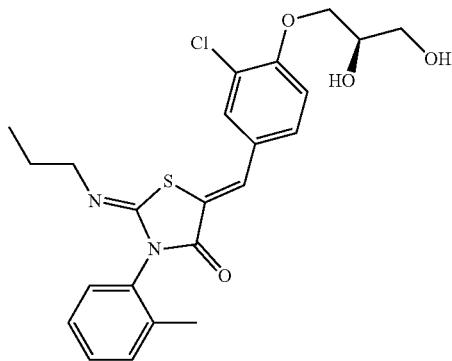

having the chemical name (Z)-5-((Z)-3-chloro-4-((R)-2,3-dihydroxypropoxy)benzylidene)-2-(propylimino)-3-(o-tolyl)thiazolidin-4-one (also known as ponesimod). Compound 1 may be prepared according to any procedure known in the art. See, e.g., International Patent Application Publication Nos. WO 2005/054215, WO 2008/062376, and WO 2014/027330.

In certain embodiments, for example, other configurations of Compound 1 are provided. In certain embodiments, for example, the co-crystals, solids forms, compositions, formulations, and methods of use provided herein may comprise one or more other configurations of Compound 1, or a mixture of Compound 1 with another configuration of Compound 1. For example, the co-crystals, solid forms, compositions, formulations, and methods of use provided herein can comprise, 5-(3-chloro-4-(2,3-dihydroxypropoxy)benzylidene)-2-(propylimino)-3-(o-tolyl)thiazolidin-4-one, in which the chiral center can have a R configuration or a S configuration. Likewise, the co-crystals, solid forms, compositions, formulations, and methods of use provided herein can comprise, 5-(3-chloro-4-(2,3-dihydroxypropoxy)benzylidene)-2-(propylimino)-3-(o-tolyl)thiazolidin-4-one in any geometric configuration, e.g., any combination of E and/or Z configurations.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

5.3 Co-Crystals and Other Solid Forms of Compound 1

While not intending to be bound by any particular theory, certain co-crystals are characterized by physical properties, e.g., stability, solubility and dissolution rate, appropriate for pharmaceutical and therapeutic dosage forms. Moreover, while not wishing to be bound by any particular theory, certain co-crystals are characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid form co-crystals suitable for the manufacture of a solid dosage form. Such properties can be determined using particular analytical chemical techniques, including solid-state analytical techniques (e.g., X-ray diffraction, microscopy, spectroscopy and thermal analysis), as described herein and known in the art.

In one embodiment, provided herein are co-crystals of Compound 1 comprising (a) Compound 1; and (b) a coformer. In one embodiment, Compound 1 is in the form of a free base. In one embodiment, Compound 1 is in the form of a free acid. In certain embodiments, Compound 1 is in the form of a zwitterion. Compound 1 can be synthesized or obtained according to a method known in the literature or based upon the teachings herein, including the methods described in detail in the examples herein.

In certain embodiments, for example, the coformer may be selected from the group consisting of L-aspartic acid, maleic acid, L-glutamic acid, pamoic acid, 1-hydroxy-2-naphthoic acid, malonic acid, gentisic acid, L-tartaric acid (for example (+)-L-tartaric acid), fumaric acid, citric acid, L-malic acid (for example (−)-L-malic acid), hippuric acid, ascorbic acid, L-ascorbic acid, benzoic acid, succinic acid, glutaric acid, camphoric acid (for example (+)-camphoric acid), nicotinic acid, orotic acid, DL-mandelic acid, 2-aminobenzoic acid, gallic acid, urea, caffeine, nicotinamide, isonicotinamide, L-prolinamide, vanillin, methyl paraben, propyl paraben, butylated hydroxyanisole, pyrogallol, chrysin, resveratrol, quercetin, saccharin, aspartame, xylitol, sucralose, D-mannitol, L-mandelic acid (for example L-(+)-mandelic acid), theophyline, sodium chloride, glycine, adenine, 2-aminopyridine, acetamide, vanillyl alcohol, lysine, glutamine, menthol, a combination of two or more of the foregoing, and derivatives thereof. In certain embodiments, for example, the coformer may be L-aspartic acid. In certain embodiments, for example, the coformer may be maleic acid. In certain embodiments, for example, the coformer may be L-glutamic acid. In certain embodiments, for example, the coformer may be pamoic acid. In certain embodiments, for example, the coformer may be 1-hydroxy-2-naphthoic acid. In certain embodiments, for example, the coformer may be malonic acid. In certain embodiments, for example, the coformer may be gentisic acid. In certain embodiments, for example, the coformer may be (+)-L-tartaric acid. In certain embodiments, for example, the coformer may be fumaric acid. In certain embodiments, for example, the coformer may be citric acid. In certain embodiments, for example, the coformer may be (−)-L-malic acid. In certain embodiments, for example, the coformer may be hippuric acid. In certain embodiments, for example, the coformer may be ascorbic acid. In certain embodiments, for example, the coformer may be L-ascorbic acid. In certain embodiments, for example, the coformer may be benzoic acid. In certain embodiments, for example, the coformer may be succinic acid. In certain embodiments, for example, the coformer may be glutaric acid. In certain embodiments, for example, the coformer may be (+)-camphoric acid. In certain embodiments, for example, the coformer may be nicotinic acid. In certain embodiments, for example, the coformer may be orotic acid. In certain embodiments, for example, the coformer may be DL-mandelic acid. In certain embodiments, for example, the coformer may be 2-aminobenzoic acid. In certain embodiments, for example, the coformer may be gallic acid. In certain embodiments, for example, the coformer may be urea. In certain embodiments, for example, the coformer may be caffeine. In certain embodiments, for example, the coformer may be nicotinamide. In certain embodiments, for example, the coformer may be isonicotinamide. In certain embodiments, for example, the coformer may be L-prolinamide. In certain embodiments, for example, the coformer may be vanillin. In certain embodiments, for example, the coformer may be methyl paraben. In certain embodiments, for example, the coformer may be propyl paraben. In certain embodiments, for example, the coformer may be butylated hydroxyanisole. In certain embodiments, for example, the coformer may be pyrogallol. In certain embodiments, for example, the coformer may be chrysin. In certain embodiments, for example, the coformer may be resveratrol. In certain embodiments, for example, the coformer may be quercetin. In certain embodiments, for example, the coformer may be saccharin. In certain embodiments, for example, the coformer may be aspartame. In certain embodiments, for example, the coformer may be xylitol. In certain embodiments, for example, the coformer may be sucralose. In certain embodiments, for example, the coformer may be D-mannitol. In certain embodiments, for example, the coformer may be L-(+)-mandelic acid. In certain embodiments, for example, the coformer may be theophyline. In certain embodiments, for example, the coformer may be sodium chloride. In certain embodiments, for example, the coformer may be glycine. In certain embodiments, for example, the coformer may be adenine. In certain embodiments, for example, the coformer may be 2-aminopyridine. In certain embodiments, for example, the coformer may be acetamide. In certain embodiments, for example, the coformer may be vanillyl alcohol. In certain embodiments, for example, the coformer may be lysine. In certain embodiments, for example, the coformer may be glutamine. In certain embodiments, for example, the coformer may be menthol.

In one embodiment, provided herein is an unsolvated solid form comprising a co-crystal of Compound 1. In one embodiment, provided herein is an anhydrous solid form comprising a co-crystal of Compound 1. In one embodiment, provided herein is an unsolvated crystal form comprising a co-crystal of Compound 1. In one embodiment, provided herein is an anhydrous crystal form comprising a co-crystal of Compound 1. In one embodiment, provided herein is an unsolvated amorphous form comprising a co-crystal of Compound 1. In one embodiment, provided herein is an anhydrous amorphous form comprising (a) Compound 1 and (b) a coformer. In one embodiment, the anhydrous form is substantially amorphous. In one embodiment, the anhydrous form is substantially crystalline. In one embodiment, provided herein is an unsolvated co-crystal of Compound 1. In one embodiment, provided herein is an anhydrous co-crystal of Compound 1.

In one embodiment, provided herein is a solvated solid form comprising a co-crystal of Compound 1. In one embodiment, provided herein is a hydrated solid form comprising a co-crystal of Compound 1. In one embodiment, provided herein is a solvated crystal form comprising a co-crystal of Compound 1. In one embodiment, provided herein is a hydrated crystal form comprising a co-crystal of Compound 1. In one embodiment, provided herein is a solvated amorphous form comprising a co-crystal of Compound 1. In one embodiment, provided herein is hydrated amorphous form comprising a co-crystal of Compound 1. In one embodiment, provided herein is a solvated co-crystal of Compound 1. In one embodiment, provided herein is a hydrated co-crystal of Compound 1. In certain embodiments, the solvated form is solvated by water, acetonitrile, diisopropyl ether, heptanes, ethyl acetate, methyl isobutyl ketone, or nitromethane. In certain embodiments, the hydrated form includes, but is not limited to, a hemihydrate, a monohydrate, a dihydrate, a trihydrate, and the like.

The co-crystals and other solid forms provided herein can be prepared by the methods described herein, or by techniques, including, but not limited to, heating, cooling, freeze drying, spray drying, lyophilization, quench cooling the melt, rapid solvent evaporation, slow solvent evaporation, solvent recrystallization, antisolvent addition, slurry recrystallization, crystallization from the melt, desolvation, recrystallization in confined spaces, such as, e.g., in nanopores or capillaries, recrystallization on surfaces or templates, such as, e.g., on polymers, recrystallization in the presence of additives, such as, e.g., co-crystal counter-molecules, desolvation, dehydration, rapid cooling, slow cooling, exposure to solvent and/or water, drying, including, e.g., vacuum drying, vapor diffusion, sublimation, grinding (including, e.g., cryo-grinding and solvent-drop grinding), microwave-induced precipitation, sonication-induced precipitation, laser-induced precipitation, and precipitation from a supercritical fluid. The particle size of the resulting solid forms, which can vary (e.g., from nanometer dimensions to millimeter dimensions), can be controlled, e.g., by varying crystallization conditions, such as, e.g., the rate of crystallization and/or the crystallization solvent system, or by particle-size reduction techniques, e.g., grinding, milling, micronizing, or sonication.

In some embodiments, the co-crystals and other solid forms can be obtained by crystallization from certain solvent systems, for example, solvent systems comprising one or more of the following solvents: ethanol, ethyl acetate, diisopropyl ether (IPE), isopropyl alcohol (IPA), methyl isobutyl ketone (MIBK), nitromethane, t-butyl methyl ether (MTBE), acetonitrile (MeCN), a mixture of MeCN and water (for example MeCN in water at a ratio of 1:9 v/v), ethyl acetate in heptane (for example ethyl acetate in heptanes at a ratio of 1:19 v/v or 1:8 v/v), nitromethane, 1-Butanol, and Toluene. In a particular embodiment, the co-crystal and/or other solid form is solvated by diisopropyl ether. In certain embodiments, a co-crystal or solid form provided herein can be obtained by cooling and evaporation crystallization, slurry-ripening crystallization, temperature-cycling crystallization, and grinding crystallization.

(a) Methods of Preparing Co-Crystals and Other Solid Forms

Co-crystals and other solid forms provided herein can be prepared by the methods described herein, or by techniques, including, but not limited to, heating, cooling, freeze drying, spray drying, lyophilization, quench cooling the melt, rapid solvent evaporation, slow solvent evaporation, solvent recrystallization, antisolvent addition, slurry recrystallization, crystallization from the melt, desolvation, recrystallization in confined spaces, such as, e.g., in nanopores or capillaries, recrystallization on surfaces or templates, such as, e.g., on polymers, recrystallization in the presence of additives, such as, e.g., desolvation, dehydration, rapid cooling, slow cooling, exposure to solvent and/or water, drying, including, e.g., vacuum drying, vapor diffusion, sublimation, grinding (including, e.g., cryo-grinding and solvent-drop grinding), microwave-induced precipitation, sonication-induced precipitation, laser-induced precipitation, and precipitation from a supercritical fluid.

In certain embodiments, the coformer is a solid under ambient temperature conditions when in its pure form.

In certain embodiments, co-crystals and other solid forms can be prepared using solid-state methods such as solid-state grinding and solvent-drop grinding. In certain embodiments, co-crystals and other solid forms can be prepared using high-throughput screening. In certain embodiments co-crystals and other solid forms can be prepared using solution-based crystallization.

In certain embodiments, co-crystal formation can lead to enhancement of physical properties of the resulting solid forms, such as solubility, dissolution rate, bioavailability, physical stability, chemical stability, flowability, fractability, or compressibility.

In certain embodiments, provided herein are grinding methods for making a co-crystal of Compound 1, comprising 1) adding Compound 1, a coformer, and a solvent into a grinding machine equipped with one or two milling balls; 2) shaking the container for a particular time at a particular frequency at ambient temperature; and 3) collecting the resulting solid. In certain embodiments, the solvent comprises one or more of the following solvents: ethanol, ethyl acetate, diisopropyl ether (IPE), isopropyl alcohol (IPA), methyl isobutyl ketone (MIBK), nitromethane, t-butyl methyl ether (MTBE), acetonitrile (MeCN), a mixture of MeCN and water (for example MeCN in water at a ratio of 1:9 v/v), ethyl acetate in heptane (for example ethyl acetate in heptanes at a ratio of 1:19 v/v or 1:8 v/v), nitromethane, 1-Butanol, and Toluene. In one embodiment, the molar ratio of Compound 1 and the coformers is about 1:1. In certain embodiments, the period of time is about 15 minutes, about 20 minutes or about 30 minutes. In one embodiment, the frequency is about 15 Hz, about 20 Hz or about 30 Hz.

Certain embodiments may provide, for example, a method for making a solid form and/or a co-crystal of Compound 1. In certain embodiments, for example, the method may comprise solvent drop grinding. In certain embodiments, for example, the solvent drop grinding may comprise: 1) combining a quantity of Compound 1 and a quantity of coformer (for example stoichiometric amounts of each) with a quantity solvent in a milling vessel; and 2) grinding with one or more (for example one) milling balls at least a predetermined rate (for example a predetermined rate of at least 20 Hz) for at least a predetermined period of time (for example a predetermined time of at least 15 minutes). In certain embodiments, for example, stoichiometric amounts of Compound 1 and a coformer may be combined in a milling vessel and ground with a Retsch Mill (Model MM301) at a temperature of 23° C. with one milling ball at 20 Hz for 15 minutes. In certain further embodiments, for example, Compound 1 and/or the coformer may be pre-ground (for example with a mortar and pestle) prior to the grinding. In certain embodiments, for example, the solvent utilized in the slurry ripening may be selected from the group consisting of ethanol, ethyl acetate, diisopropyl ether (IPE), isopropyl alcohol (IPA), methyl isobutyl ketone (MIBK), nitromethane, t-butyl methyl ether (MTBE), acetonitrile (MeCN), a mixture of MeCN and water (for example MeCN in water at a ratio of 1:9 v/v), ethyl acetate in heptane (for example ethyl acetate in heptanes at a ratio of 1:19 v/v or 1:8 v/v), nitromethane, 1-Butanol, and Toluene.

In certain embodiments, for example, the method may comprise slurry ripening. In certain embodiments, for example, the slurry ripening may comprise forming a mixture containing a quantity of Compound 1 and a quantity of a coformer (at a 1:1 molar equivalent ratio) in a solvent, e.g., a solvent saturated with the coformer, followed by temperature cycling between two predetermined temperatures (for example between 25° C. and 5° C.) for a predetermined period of time (for example a time of 10 days). In certain embodiments, the solvent is 1-butanol or toluene.

In certain embodiments, provided herein are combinations of grinding and slurry methods comprising 1) adding Compound 1, a coformer, and a solvent into a grinding container equipped with one or two milling balls; 2) shaking the container for a particular time at a particular frequency; 3) collecting the solids and transferring them to vials containing a tumble stir disc with a solvent to obtain a slurry; 4) stirring the slurry for a period of time while cycling the temperature between two set temperatures (for example between 25° C. and 5° C.); 5) collecting a solid from the slurry by filtration (e.g., centrifuge filtration); and 6) drying the collected solids for a period of time to yield the co-crystal of Compound 1. In certain embodiments, the solvent employed in the grinding container is ethanol, ethyl acetate, t-butyl methyl ether, a mixture of acetonitrile (MeCN) and water (for example MeCN in water at a ratio of 1:9 v/v), toluene, and isopropyl alcohol. In one embodiment, the molar ratio of Compound 1 and the coformers is about 1:1. In certain embodiments, the mixture is Compound 1 and saturated coformer solution. In certain embodiments, the period of time of shaking the grinding container is 15 minutes, 20 minutes or about 30 minutes. In one embodiment, the frequency of shaking the grinding container is about 15 Hz, about 20 Hz or about 30 Hz. In one embodiment, the solvent used to obtain a slurry is ethanol, ethyl acetate, t-butyl methyl ether, a mixture of acetonitrile (MeCN) and water (for example MeCN in water at a ratio of 1:9 v/v). In one embodiment, the period of time for stirring the slurry is about 10 days. In one embodiment, the temperature of the slurry is cycled between about 25° C. and about 5° C., for about one hour at each temperature over the course of about 10 days. In certain embodiments, additional solvent of the same kind may be added to yield mixable suspensions for final isolations. In one embodiment, the solids are isolated by filtration and air-dried for 18 hours.

In certain embodiments, for example, the saturated coformer solution may be prepared by 1) combining the quantity of coformer in a quantity (for example, about 2 mL) of solvent; 2) mixing the combined quantities at a predetermined temperature (for example 23° C.) for a predetermined period of time (for example at least about 16 hours or less than about 16 hours) to form a suspension; and 3) filtering the suspension (for example filtering the suspension through an 0.2 micron PTFE filter if the solvent is an organic solvent or an 0.45 micron filter if the solvent is an organic solvent mixed with water). In certain embodiments, for example, the solvent may be selected from the group consisting of ethyl alcohol, a solution of ethyl acetate and heptane (for example a solution having an ethyl acetate to heptane at ratio of 2:8 v/v), a solution of acetonitrile and water (for example a solution having a acetonitrile to water ratio of 1:9 v/v), and t-butyl methyl ether (MTBE), or a combination of two or more of the foregoing.

In certain embodiments, for example, the method may comprise evaporation.

In certain embodiments, provided herein are evaporation methods for making a co-crystal of Compound 1 from solutions resulting from slurry ripening method. The resultant solutions are slowly evaporated in a fume hood until dryness at ambient temperature.

The co-crystals and other solid forms provided herein may be characterized using a number of methods known to a person having ordinary skill in the art, including, but not limited to, single crystal X-ray diffraction, X-ray powder diffraction (PXRD), microscopy (e.g., polarized light microscopy (PLM), scanning electron microscopy (SEM)), thermal analysis (e.g., differential scanning calorimetry (DSC), thermal gravimetric analysis (TGA), single differential thermal analysis (SDTA), and hot-stage microscopy), spectroscopy (e.g., infrared, Raman, and nuclear magnetic resonance), high performance liquid chromatography coupled with mass spectroscopy (HPLC-MS), thermogravimetrical analysis coupled with infrared analysis (TG-IR), and thermogravimetric analysis coupled with mass spectroscopy (TGA-MS). The particle size and size distribution of the solid form provided herein may be determined by conventional methods, such as laser light diffraction technique.

The purity of the co-crystals and other solid forms provided herein may be determined by standard analytical methods, such as thin layer chromatography (TLC), gel electrophoresis, gas chromatography, high performance liquid chromatography (HPLC), and mass spectrometry.

It should be understood that the numerical values of the peaks of an X-ray powder diffraction pattern may vary slightly from one machine to another or from one sample to another, and so the values quoted are not to be construed as absolute, but with an allowable variability, such as ±0.2 degrees two theta (2θ) (see, United States Pharmacopoeia, page 2228 (2003)).

(b) Co-Crystal Form 1: A Co-Crystal Comprising Compound 1 and L-Prolinamide

Provided herein is co-crystal Form 1, i.e., a co-crystal comprising Compound 1 and L-prolinamide. In one embodiment, provided herein is a solid form comprising co-crystal Form 1. In one embodiment, provided herein is a solid form comprising (i) co-crystal Form 1 and (ii) an amorphous form of Compound 1. In one embodiment, provided herein is a solid form comprising (i) co-crystal Form 1 and (ii) one or more additional crystal forms of Compound 1. Provided herein are various embodiments, preparations, or modifications of co-crystal Form 1.

In one embodiment, co-crystal Form 1 is a non-solvated form. In another embodiment, co-crystal Form 1 is a solvated form.

In one embodiment, co-crystal Form 1 has an X-ray powder diffraction pattern substantially as shown in FIG. 1. In one embodiment, co-crystal Form 1 has an X-ray powder diffraction pattern comprising one or more (i.e., one, two, three, four, five, six, seven, eight, nine, ten, eleven, twelve, thirteen, or fourteen) characteristic X-ray powder diffraction peaks at 2θ angles of approximately 6.8, 11.2, 12.7, 13.1, 15.2, 15.6, 16.7, 19.4, 20.5, 21.4, 22.9, 23.8, 25.5, and 26.0±0.2 2θ as depicted in FIG. 1. In one embodiment, co-crystal Form 1 has an X-ray powder diffraction pattern comprising one or more (i.e., one, two, three, four, five, six, seven, eight, or nine) characteristic X-ray powder diffraction peaks at 2θ angles of approximately 6.8, 11.2, 16.7, 19.4, 20.5, 21.4, 22.9, 23.8, and 26.0±0.2 2θ as depicted in FIG. 1. In one embodiment, co-crystal Form 1 has an X-ray powder diffraction pattern comprising one or more (i.e., one, two, three, four, five, six, or seven) characteristic X-ray powder diffraction peaks at 2θ angles of approximately 6.8, 11.2, 16.7, 20.5, 21.4, 22.9, and 23.8±0.2 2θ as depicted in FIG. 1. In one embodiment, co-crystal Form 1 has an X-ray powder diffraction pattern comprising one or more (i.e., one, two, or three) characteristic X-ray powder diffraction peaks at 2θ angles of approximately 6.8, 11.2, and 19.4±0.2 2θ as depicted in FIG. 1.

Figure 2:
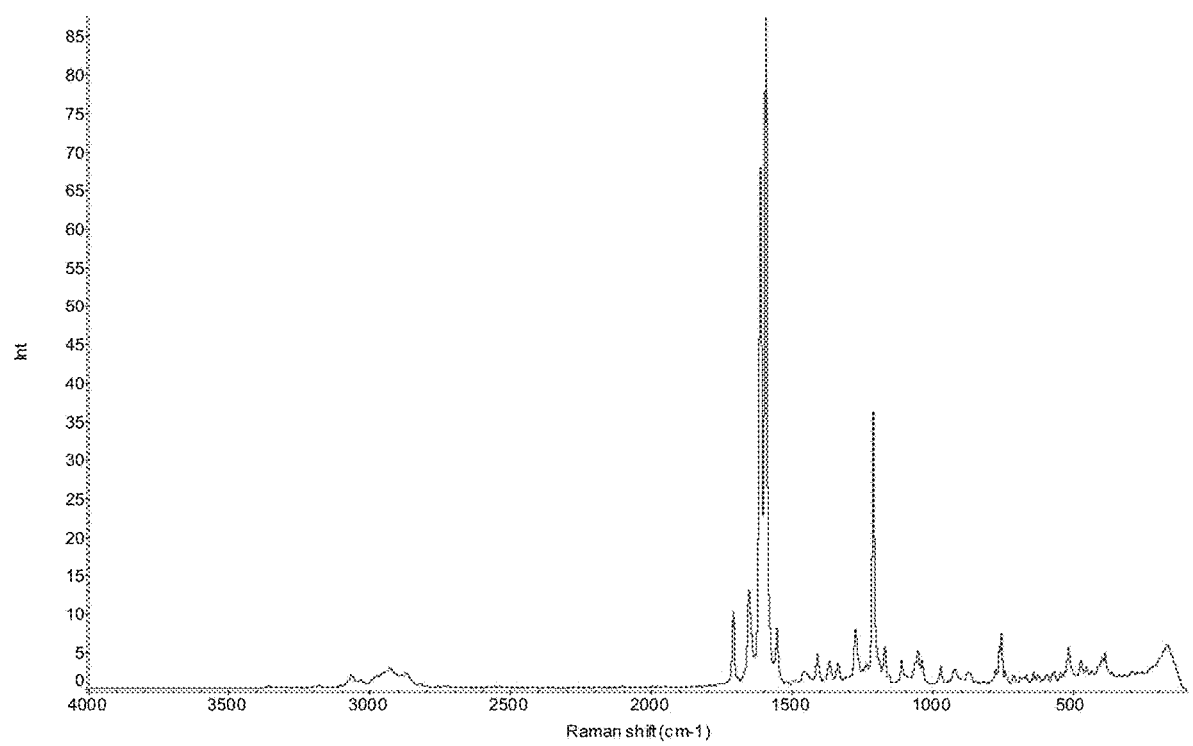
FIG. 2 depicts a representative FT-Raman spectrum of co-crystal Form 1 of Compound 1.

In one embodiment, co-crystal Form 1 has an FT-Raman Spectrum substantially as depicted in FIG. 2.

Figure 3:
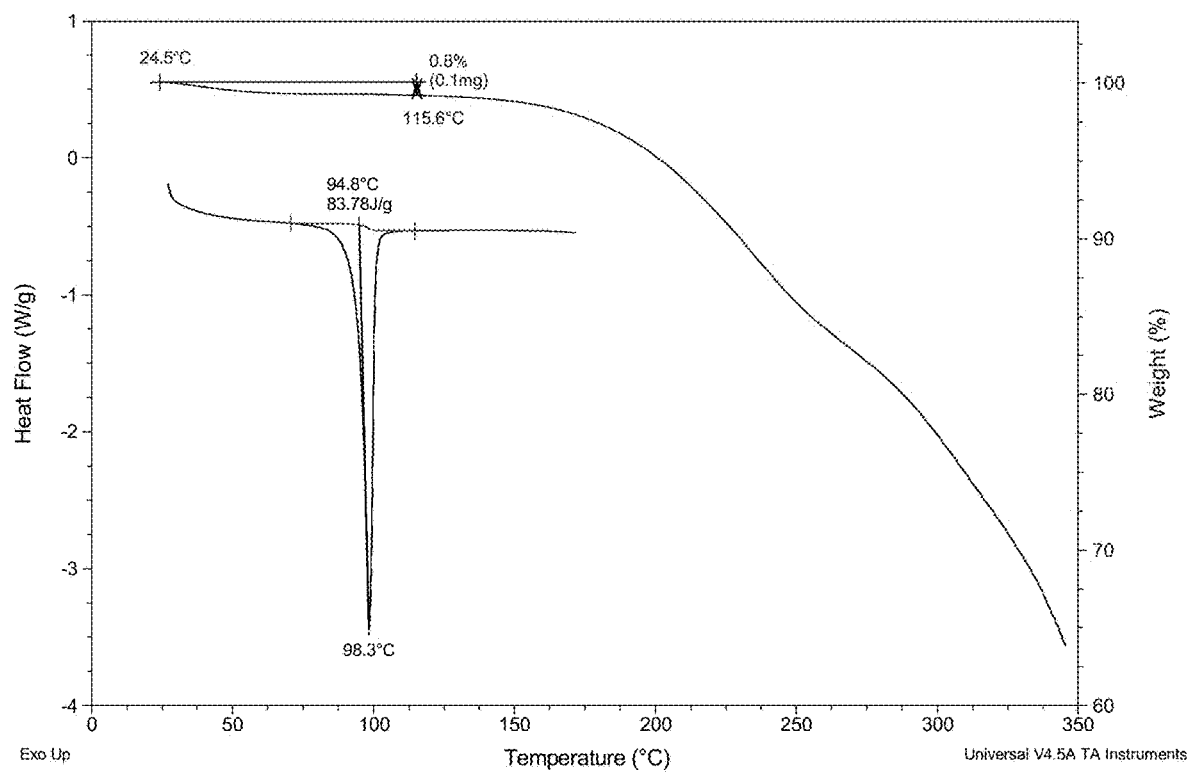
FIG. 3 depicts representative differential scanning calorimetry (DSC) and thermal gravimetric analysis (TGA) thermograms of co-crystal Form 1 of Compound 1.

In one embodiment, co-crystal Form 1 has a DSC thermograph substantially as depicted in FIG. 3. In one embodiment, DSC analysis of co-crystal Form 1 showed a melting endotherm with onset at about 94.8° C.

In one embodiment, co-crystal Form 1 has a TGA thermograph substantially as depicted in FIG. 3. In one embodiment, TGA-IR analysis of co-crystal Form 1 shows about 0.8% weight loss between 24.5-115.6° C.

Figure 4:
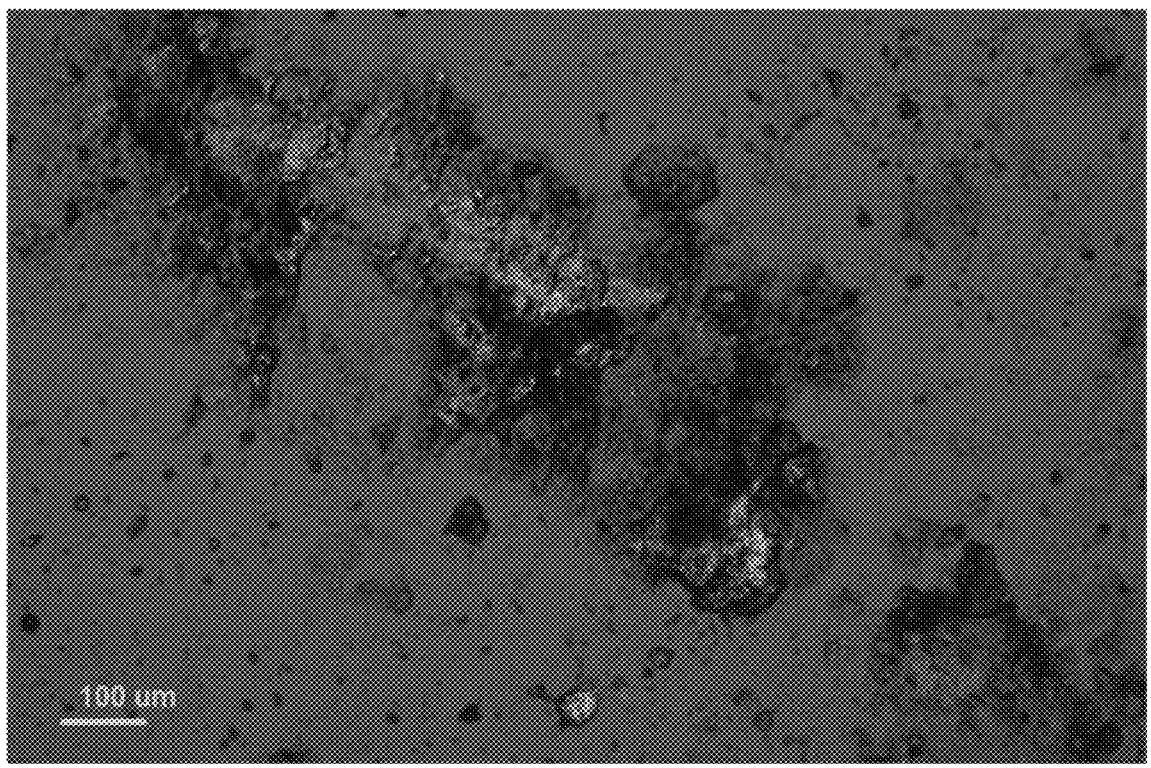
FIG. 4 depicts a representative polarized-light microscopy (PLM) image of co-crystal Form 1 of Compound 1.

In one embodiment, co-crystal Form 1 has a polarized-light microscopy substantially as depicted in FIG. 4.

In one embodiment, proton PLM analysis of co-crystal Form 1 indicates a 1:1.1 stoichiometry of Compound 1 to L-prolinamide. Accordingly, in an embodiment, co-crystal Form 1 includes a Compound 1-to-L-prolinamide ratio of about 1:1.1.

In still another embodiment, co-crystal Form 1 is substantially pure. In certain embodiments, the substantially pure co-crystal Form 1 is substantially free of other solid forms, e.g., free of amorphous forms. In certain embodiments, the purity of the substantially pure co-crystal Form 1 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

In certain embodiments, co-crystal Form 1 is obtained by combinations of grinding and slurry experiments comprising 1) adding Compound 1, L-prolinamide and a solvent into a grinding container equipped with one or two milling balls; 2) shaking the container for a particular time at a particular frequency; 3) collecting the solids and transferring them to vials containing a tumble stir disc with a solvent to obtain a slurry; 4) stirring the slurry for a period of time while cycling the temperature between two set temperatures; 5) collecting a solid from the slurry by filtration; and 6) drying the collected solids for a period of time to yield co-crystal Form 1. In one embodiment, the solids are dried using air. In certain embodiments, the method further comprises the step of evaporating the supernatant under a flow of nitrogen gas at a certain temperature (e.g., ambient temperature) over a period of time to yield the co-crystal Form 1. In certain embodiments, the solvent employed in the grinding container is ethanol, ethyl acetate, methyl t-butyl ether, or acetonitrile in water at a ratio of 1:9 v/v. In one embodiment, the molar ratio of Compound 1 and the coformers is about 1:1. In certain embodiments, the period of time of shaking the grinding container is about 15 minutes, about 20 minutes or about 30 minutes. In certain embodiments, the frequency of shaking the grinding container is about 20 Hz or about 30 Hz. In certain embodiments, the solvent used to obtain a slurry is ethanol, methyl t-butyl ether, ethyl acetate to heptane at ratio of 2:8 v/v, 1-butanol, or toluene. In certain embodiments, the solvent is saturated with coformer. In one embodiment, the period of time for stirring the slurry is about 44 hours while cycling temperature between 35° C. and 20° C. with 0.1° C./min slow cool, followed by cycling temperature between 25° C. and 5° C. with 1 hour hold at each temperature for 3 days.

(c) Co-Crystal Form 2: A Co-Crystal Comprising Compound 1 and Pyrogallol

Provided herein is co-crystal Form 2, i.e., a co-crystal comprising Compound 1 and pyrogallol. In one embodiment, provided herein is a solid form comprising co-crystal Form 2. In one embodiment, provided herein is a solid form comprising (i) co-crystal Form 2 and (ii) an amorphous form of Compound 1. In one embodiment, provided herein is a solid form comprising (i) co-crystal Form 2 and (ii) one or more additional crystal forms of Compound 1. Provided herein are various embodiments, preparations, or modifications of co-crystal Form 2. In one embodiment, co-crystal Form 2 is a non-solvated form. In another embodiment, co-crystal Form 2 is a solvated form.

Figure 5:
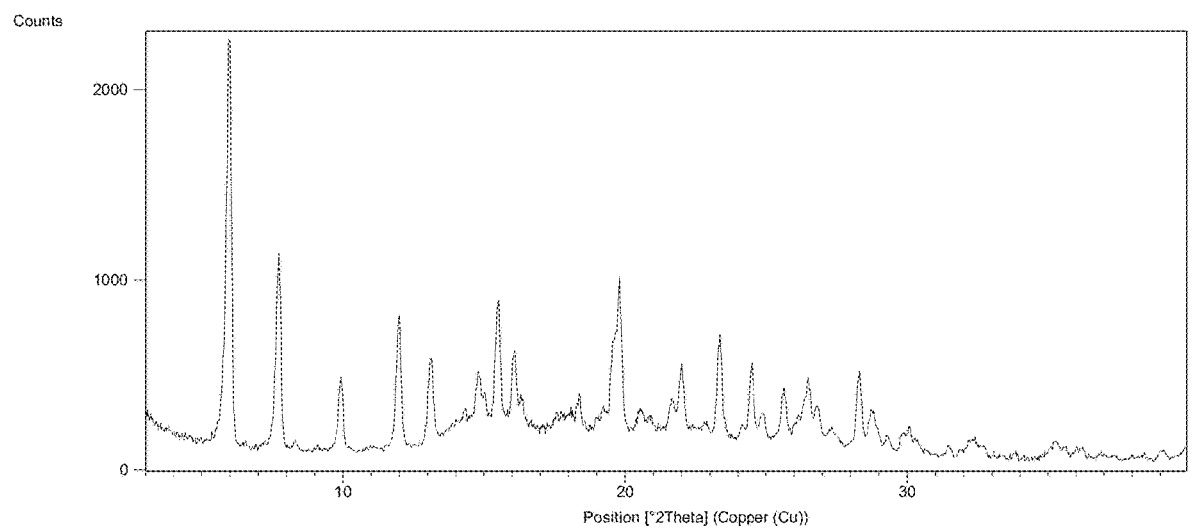
FIG. 5 depicts a representative PXRD pattern of co-crystal Form 2 of Compound 1.

In one embodiment, co-crystal Form 2 has an X-ray powder diffraction pattern substantially as shown in FIG. 5. In one embodiment, co-crystal Form 2 has an X-ray powder diffraction pattern comprising one or more (i.e., one, two, three, four, five, six, seven, eight, nine, ten, eleven, twelve, thirteen, fourteen, fifteen, sixteen, or seventeen) characteristic X-ray powder diffraction peaks at 2θ angles of approximately 6.0, 7.7, 9.9, 12.0, 13.1, 14.8, 15.5, 16.1, 18.4, 19.8, 22.0, 23.3, 24.5, 25.6, 26.5, 28.3, and 28.8±0.2 2θ as depicted in FIG. 5. In one embodiment, co-crystal Form 2 has an X-ray powder diffraction pattern comprising one or more (i.e., one, two, three, four, five, six, seven, eight, nine, ten, eleven, twelve, or thirteen) characteristic X-ray powder diffraction peaks at 2θ angles of approximately 6.0, 7.7, 9.9, 12.0, 14.8, 15.5, 16.1, 18.4, 19.8, 23.3, 26.5, 28.3, and 28.8±0.2 2θ as depicted in FIG. 5. In one embodiment, co-crystal Form 2 has an X-ray powder diffraction pattern comprising one or more (i.e., one, two, three, four, five, six, seven, or eight) characteristic X-ray powder diffraction peaks at 2θ angles of approximately 6.0, 7.7, 9.9, 12.0, 14.8, 16.1, 19.8, and 28.8±0.2 2θ as depicted in FIG. 5. In one embodiment, co-crystal Form 2 has an X-ray powder diffraction pattern comprising one or more (i.e., one, two, or three) characteristic X-ray powder diffraction peaks 2θ angles of approximately 6.0, 7.7, and 12.0±0.2 2θ as depicted in FIG. 5.

Figure 6:
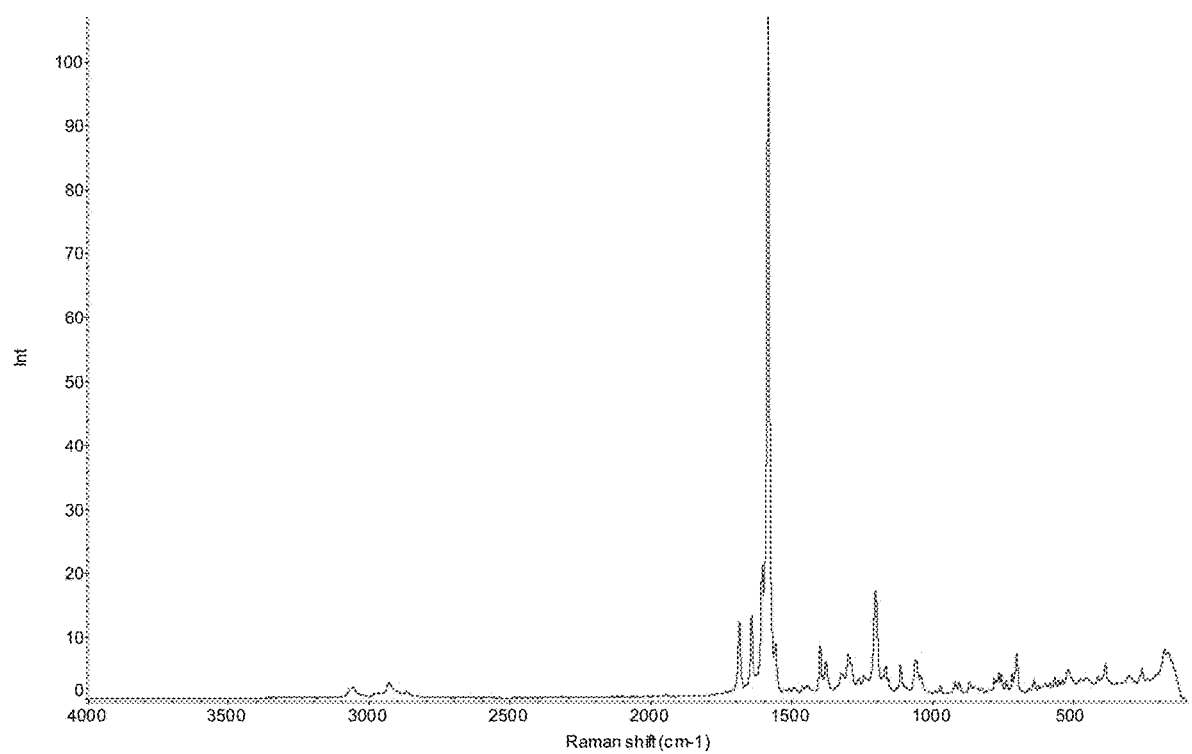
FIG. 6 depicts a representative FT-Raman spectrum of co-crystal Form 2 of Compound 1.

In one embodiment, co-crystal Form 2 has an FT-Raman Spectrum substantially as depicted in FIG. 6.

Figure 7:
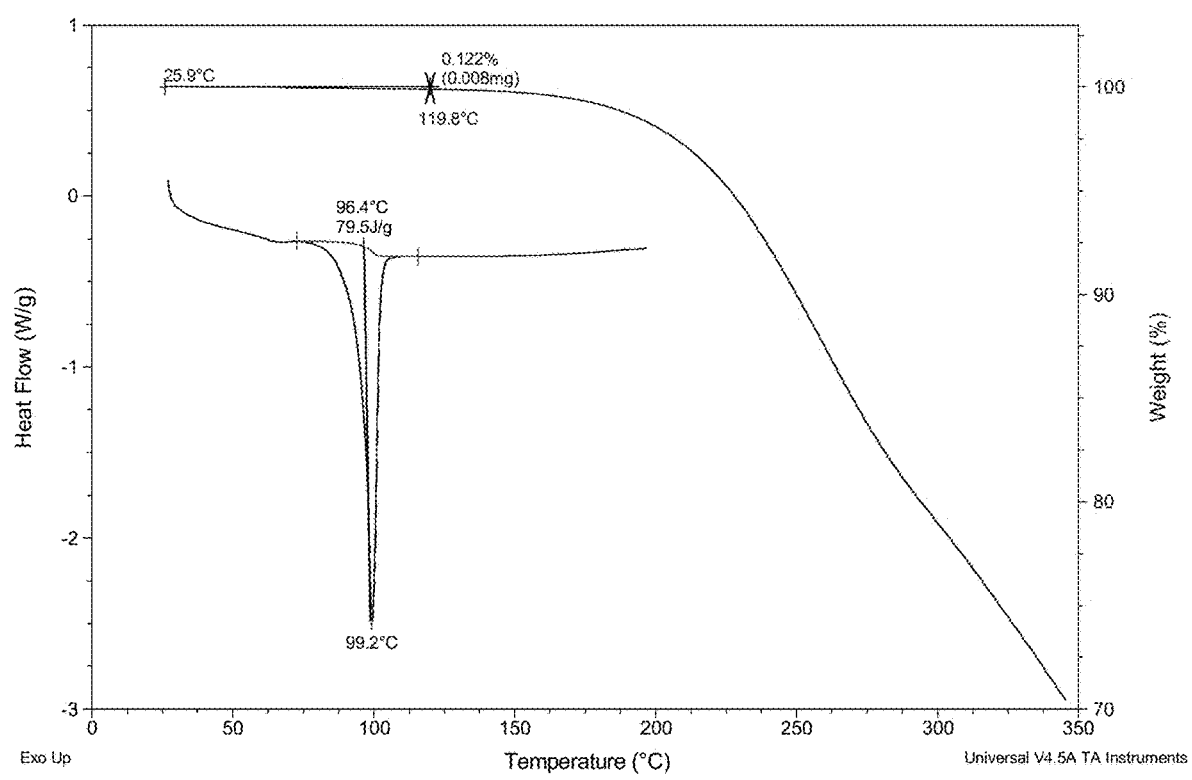
FIG. 7 depicts representative DSC and TGA thermograms of co-crystal Form 2 of Compound 1.

In one embodiment, co-crystal Form 2 has a DSC thermograph substantially as depicted in FIG. 7. In one embodiment, DSC analysis of co-crystal Form 2 showed a melting endotherm with onset temperature at about 96.4° C.

In one embodiment, co-crystal Form 2 has a TGA thermograph substantially as depicted in FIG. 7. In one embodiment, TGA-IR analysis of co-crystal Form 2 showed about 0.1% weight loss between 25.9-119.8° C.

Figure 8:
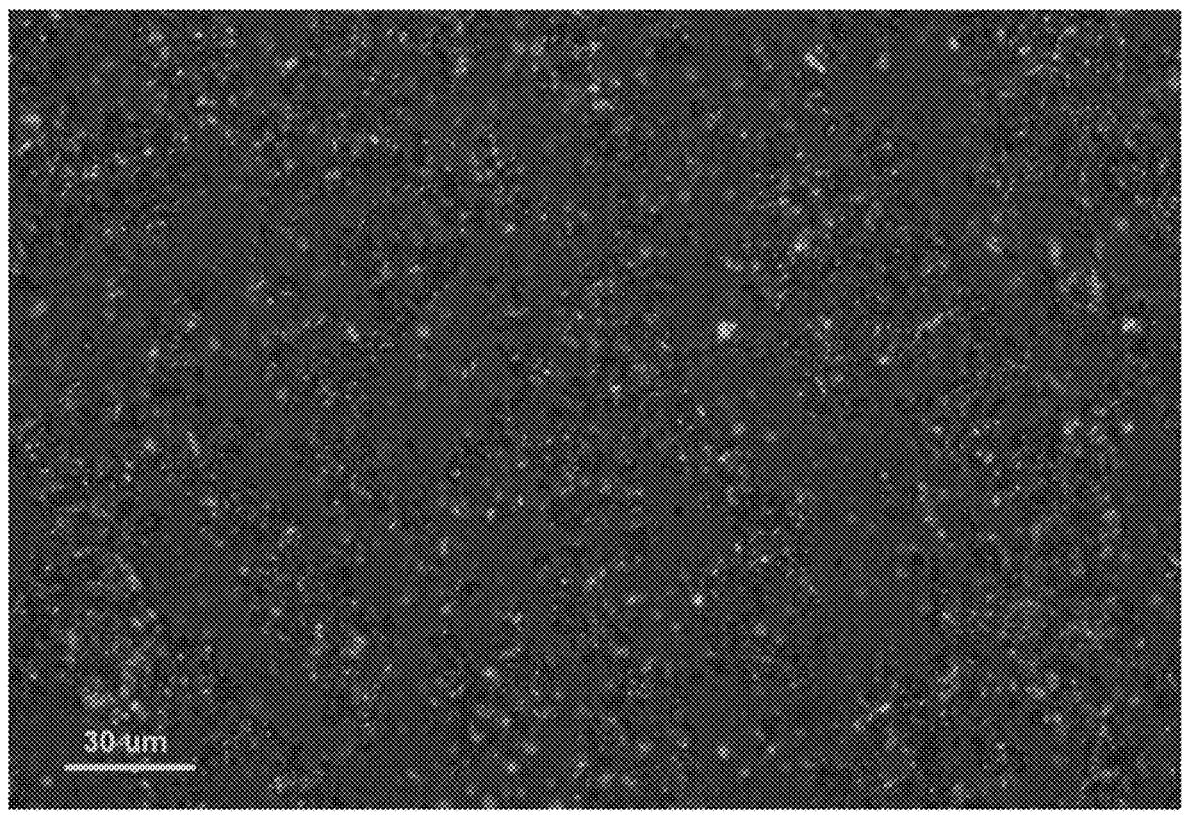
FIG. 8 depicts a representative PLM image of co-crystal Form 2 of Compound 1.

In one embodiment, co-crystal Form 2 has a polarized light microscopy substantially as depicted in FIG. 8.

In one embodiment, proton PLM analysis of co-crystal Form 2 indicates a 1:1.2 stoichiometry of Compound 1 to pyrogallol. Accordingly, in some embodiments, co-crystal Form 2 includes a Compound 1-to-pyrogallol ratio of about 1:1.2.

In still another embodiment, co-crystal Form 2 is substantially pure. In certain embodiments, the substantially pure co-crystal Form 2 is substantially free of other solid forms, e.g., free of amorphous forms. In certain embodiments, the purity of the substantially pure co-crystal Form 2 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

In certain embodiments, co-crystal Form 2 is obtained by combinations of grinding and slurry experiments comprising 1) adding Compound 1, pyrogallol, and a solvent into a grinding container equipped with one or two milling balls; 2) shaking the container for a particular time at a particular frequency; 3) collecting the solids and transferring them to vials containing a tumble stir disc with a solvent to obtain a slurry; 4) stirring the slurry for a period of time while cycling the temperature between two set temperatures; 5) collecting a solid from the slurry by filtration; and 6) drying the collected solids for a period of time to yield co-crystal Form 2. In one embodiment, the solids are dried using air. In certain embodiments, the method further comprises the step of evaporating the supernatant under a flow of nitrogen gas at a certain temperature (e.g., ambient temperature) over a period of time to yield co-crystal Form 2. In certain embodiments, the solvent employed in the grinding container is ethanol, ethyl acetate, methyl t-butyl ether, or acetonitrile in water at a ratio of 1:9 v/v. In one embodiment, the molar ratio of Compound 1 and the coformers is about 1:1. In certain embodiments, the period of time of shaking the grinding container is about 15 minutes, about 20 minutes, or about 30 minutes. In certain embodiments, the frequency of shaking the grinding container is about 20 Hz or about 30 Hz. In certain embodiments, the solvent used to obtain a slurry is ethanol, ethyl acetate in heptane at a ratio of 2:8 v/v, methyl t-butyl ether, 1-butanol, or toluene. In certain embodiments, the solvent is saturated with coformer. In one embodiment, the period of time for stirring the slurry is about 3 days while cycling temperature between 25° C. and 5° C. with 0.1° C./min slow cool.

(d) Co-Crystal Form 3: A Co-Crystal Comprising Compound 1 and Aspartame

Provided herein is co-crystal Form 3, a co-crystal comprising Compound 1 and aspartame. In one embodiment, provided herein is a solid form comprising co-crystal Form 3. In one embodiment, provided herein is a solid form comprising (i) co-crystal Form 3 and (ii) an amorphous form of Compound 1. In one embodiment, provided herein is a solid form comprising (i) co-crystal Form 3 and (ii) one or more additional crystal forms of Compound 1. Provided herein are various embodiments, preparations, or modifications of co-crystal Form 3.

In one embodiment, co-crystal Form 3 is a hydrated form. In one embodiment, co-crystal Form 3 is a non-solvated form. In another embodiment, co-crystal Form 3 is a solvated form.

Figure 9:
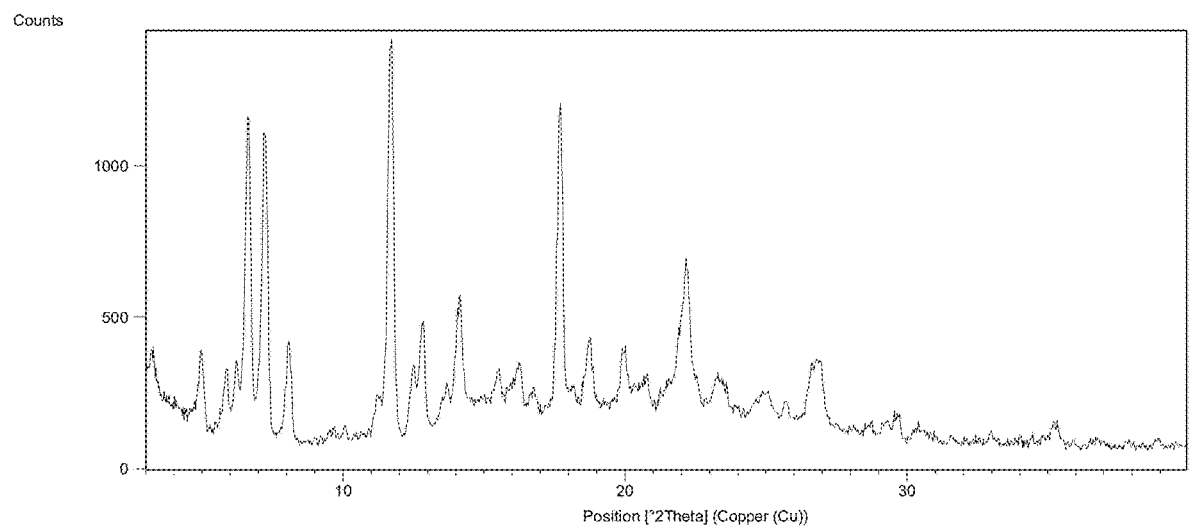
FIG. 9 depicts a representative PXRD pattern of co-crystal Form 3 of Compound 1.

In one embodiment, co-crystal Form 3 has an X-ray powder diffraction pattern substantially as shown in FIG. 9. In one embodiment, co-crystal Form 3 has an X-ray powder diffraction pattern comprising one or more (i.e., one, two, three, four, five, six, seven, eight, nine, ten, eleven, or twelve) characteristic X-ray powder diffraction peaks at 2θ angles of approximately 5.0, 5.9, 6.2, 6.7, 7.3, 8.1, 11.7, 12.8, 14.2, 17.7, 18.7, and 22.2±0.2 2θ as depicted in FIG. 9. In one embodiment, co-crystal Form 3 has an X-ray powder diffraction pattern comprising one or more (i.e., one, two, three, or four) characteristic X-ray powder diffraction peaks at 2θ angles of approximately 5.0, 6.7, 11.7, and 17.7±0.2 2θ as depicted in FIG. 9. In one embodiments, co-crystal Form 3 has an X-ray powder diffraction pattern comprising one or more (i.e., one, two, or three) characteristic X-ray powder diffraction peaks at 2θ angles of approximately 5.0, 6.7, and 17.7±0.2 2θ as depicted in FIG. 9.

Figure 10:
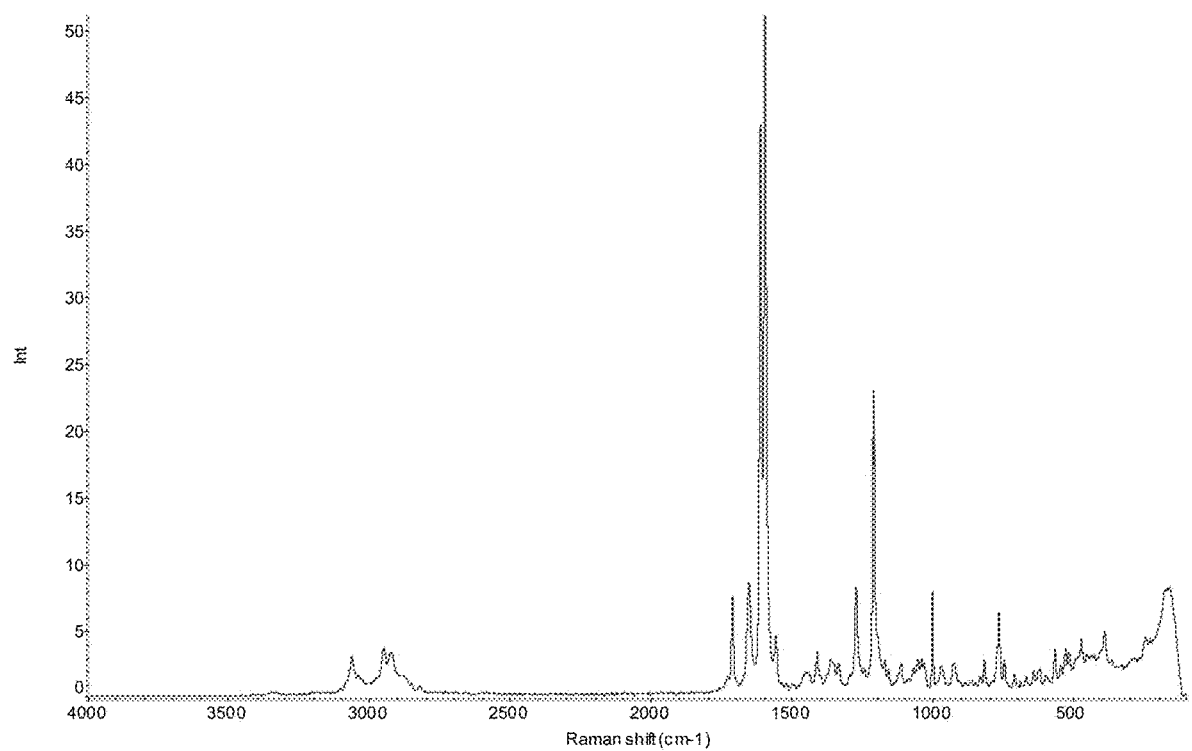
FIG. 10 depicts a representative FT-Raman spectrum of co-crystal Form 3 of Compound 1.

In one embodiment, co-crystal Form 3 has an FT-Raman Spectrum substantially as depicted in FIG. 10.

Figure 11:
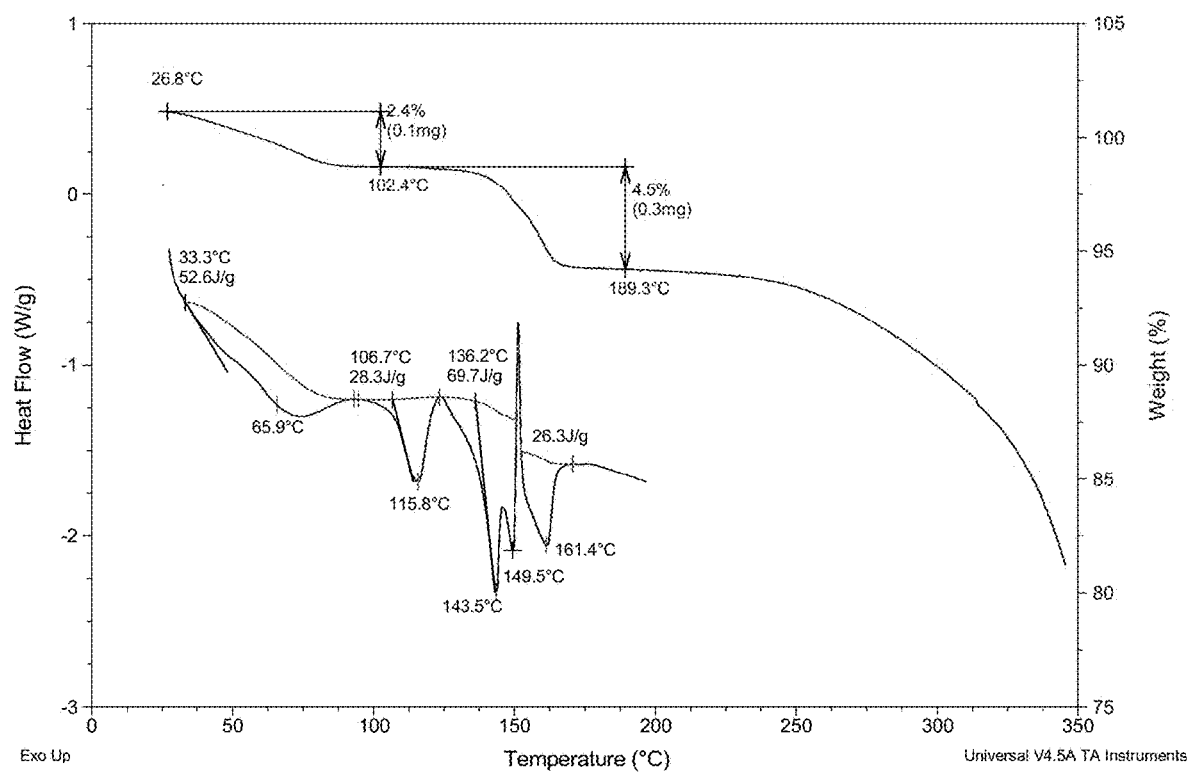
FIG. 11 depicts representative DSC and TGA thermograms of co-crystal Form 3 of Compound 1.

In one embodiment, co-crystal Form 3 has a DSC thermograph substantially as depicted in FIG. 11. In one embodiment, DSC analysis of co-crystal Form 3 shows a dehydration endotherm with onset at about 33.3° C., a melting endotherm with onset at about 106.7° C., and a possible decomposition exotherm with onset at about 136.2° C.

In one embodiment, co-crystal Form 3 has a TGA thermograph substantially as depicted in FIG. 11. In one embodiment, TGA-IR analysis of co-crystal Form 3 shows about 2.4% weight loss of water between 26.8-102.4° C., followed by about 4.5% weight loss of methanol up to about 189.3° C. Without being bound by any particular theory, the loss of water may indicate a hydrate form. Without being bound by any particular theory, the loss of methanol may indicate decomposition of aspartame.

Figure 12:
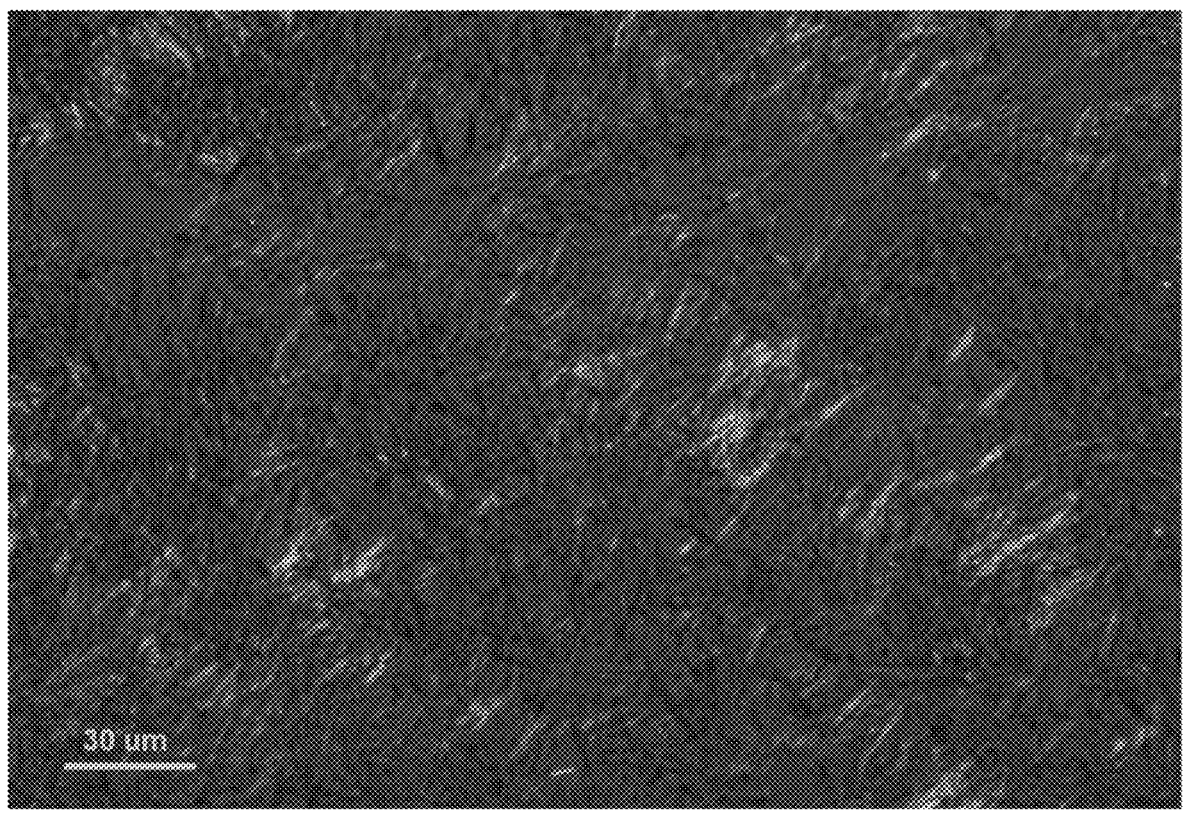
FIG. 12 depicts a representative PLM image of co-crystal Form 3 of Compound 1.

In one embodiment, co-crystal Form 3 has a polarized light microscopy substantially as depicted in FIG. 12.

In one embodiment, proton PLM analysis of co-crystal Form 3 indicates a 1:1.2 stoichiometry of Compound 1 to aspartame. Accordingly, in certain embodiments, co-crystal Form 3 includes a Compound 1-to-aspartame ratio of about 1:1.2.

In still another embodiment, co-crystal Form 3 is substantially pure. In certain embodiments, the substantially pure co-crystal Form 3 is substantially free of other solid forms, e.g., free of amorphous forms. In certain embodiments, the purity of the substantially pure co-crystal Form 3 is no less than about 95% pure, no less than about 96% pure, no less than about 97% pure, no less than about 98% pure, no less than about 98.5% pure, no less than about 99% pure, no less than about 99.5% pure, or no less than about 99.8% pure.

In certain embodiments, co-crystal Form 3 is obtained by combinations of grinding and slurry experiments comprising 1) adding Compound 1, aspartame, and a solvent into a grinding container equipped with one or two milling balls; 2) shaking the container for a particular time at a particular frequency; 3) collecting the solids and transferring them to vials containing a tumble stir disc with a solvent to obtain a slurry; 4) stirring the slurry for a period of time while cycling the temperature between two set temperatures; 5) collecting a solid from the slurry by filtration; and 6) drying the collected solids for a period of time to yield co-crystal Form 3. In one embodiment, the solids are dried using air. In certain embodiments, the method further comprises the step of evaporating the supernatant under a flow of nitrogen gas at a certain temperature (e.g., ambient temperature) over a period of time to yield co-crystal Form 3. In certain embodiments, the solvent employed in the grinding container is ethanol, ethyl acetate, methyl t-butyl ether, or acetonitrile in water at a ratio of 1:9 v/v. In one embodiment, the molar ratio of Compound 1 and the coformers is about 1:1. In certain embodiments, the period of time of shaking the grinding container is about 15 minutes, about 20 minutes, or about 30 minutes. In certain embodiments, the frequency of shaking the grinding container is about 20 Hz or about 30 Hz. In certain embodiments, the solvent used to obtain a slurry is ethanol, or 1-butanol. In certain embodiments, the solvent is saturated with coformer. In one embodiment, the period of time for stirring the slurry is about 44 hours while cycling temperature between 25° C. and 5° C. with 0.1° C. slow cool.

(e) Solid Form A: Compound 1 and Citric Acid

Provided herein is Solid Form A, which comprises Compound 1 and citric acid. In one embodiment, provided herein is a solid form comprising Solid Form A. In one embodiment, Solid Form A is a co-crystal. In one embodiment, provided herein is a solid form comprising (i) Solid Form A and (ii) an amorphous form of Compound 1. In one embodiment, provided herein is a solid form comprising (i) Solid Form A and (ii) one or more additional crystal forms of Compound 1. Provided herein are various embodiments, preparations, or modifications of Solid Form A.

Figure 13:
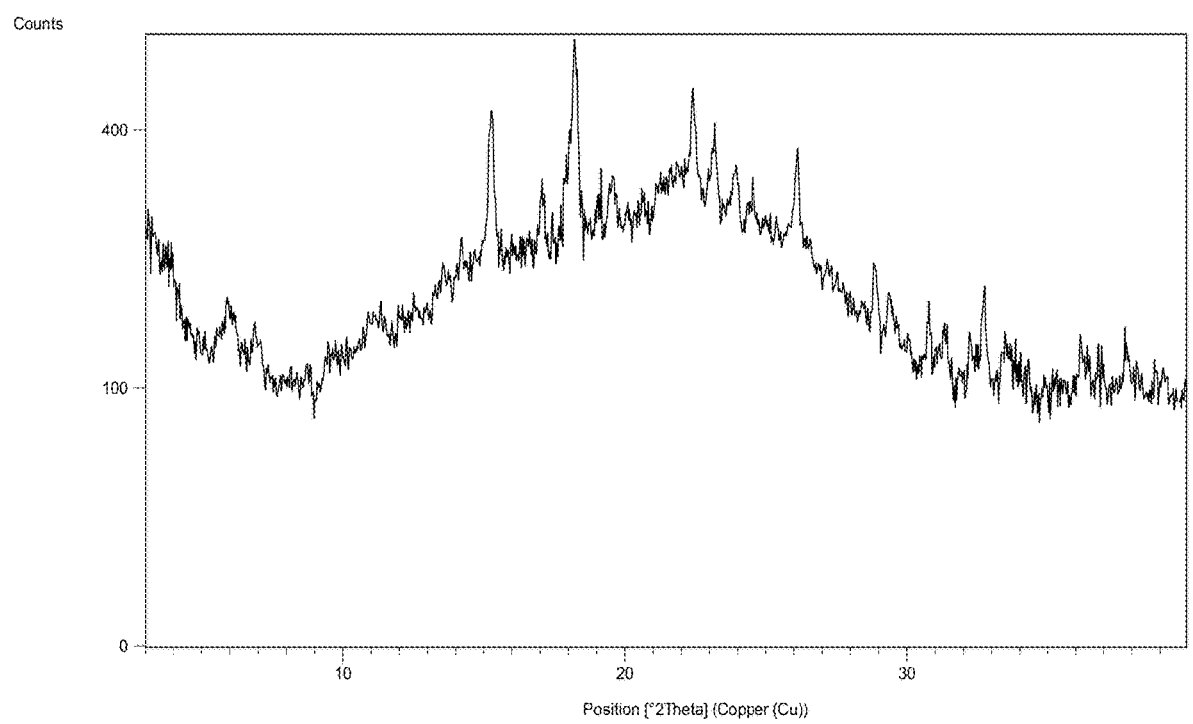
FIG. 13 depicts a representative PXRD pattern of Solid Form A of Compound 1.

In one embodiment, Solid Form A has an X-ray powder diffraction pattern substantially as shown in FIG. 13. In one embodiment, Solid Form A has an X-ray powder diffraction pattern comprising one or more (i.e., one, two, or three) characteristic X-ray powder diffraction peaks at a 2θ angle of approximately 15.3, 18.2, and 22.4±0.2 2θ, as depicted in FIG. 13.

Figure 14:
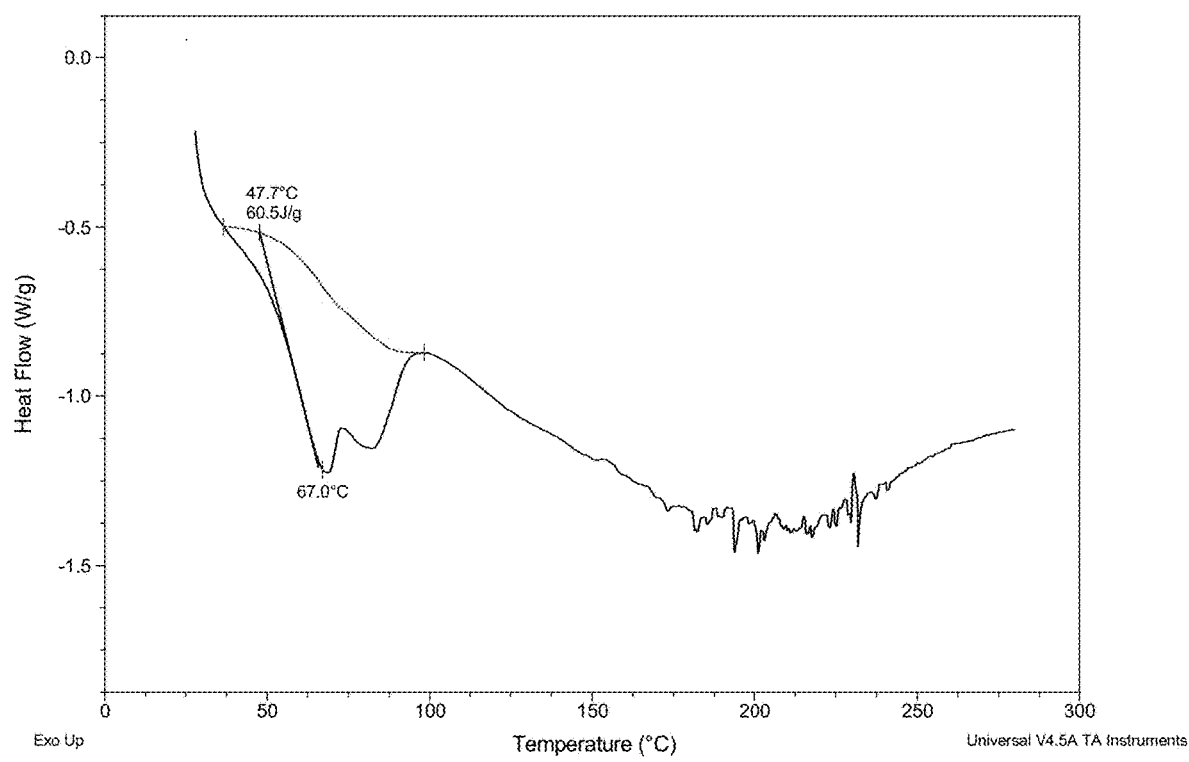
FIG. 14 depicts a representative DSC thermogram of Solid Form A of Compound 1.

In one embodiment, Solid Form A has a DSC thermograph substantially as depicted in FIG. 14. In one embodiment, DSC analysis of Solid Form A shows an endotherm with onset at about 47.7° C.

In still another embodiment, Solid Form A is substantially pure. In certain embodiments, the substantially pure Solid Form A is substantially free of other solid forms, e.g., amorphous form. In certain embodiments, the purity of the substantially pure Solid Form A is no less than about 95% pure, no less than about 96% pure, no less than about 97% pure, no less than about 98% pure, no less than about 98.5% pure, no less than about 99% pure, no less than about 99.5% pure, or no less than about 99.8% pure.

(f) Solid Form B: Compound 1 and Nicotinamide

Provided herein is Solid Form B which comprises Compound 1 and nicotinamide. In one embodiment, provided herein is a solid form comprising Solid Form B. In one embodiment, Solid Form B is a co-crystal. In one embodiment, provided herein is a solid form comprising (i) Solid Form B and (ii) an amorphous form of Compound 1. In one embodiment, provided herein is a solid form comprising (i) Solid Form B and (ii) one or more additional crystal forms of Compound 1. Provided herein are various embodiments, preparations, or modifications of Solid Form B.

Figure 21:
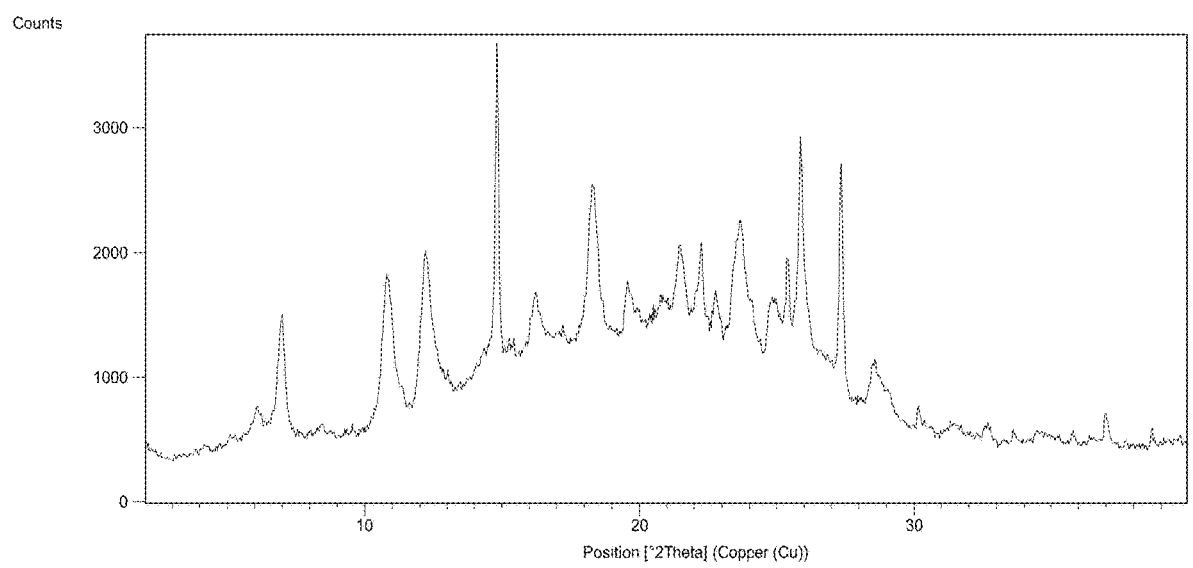
FIG. 21 depicts a representative PXRD pattern of Solid Form B of Compound 1.

In one embodiment, Solid Form B has an X-ray powder diffraction pattern substantially as shown in FIG. 21. In one embodiment, Solid Form B has an X-ray powder diffraction pattern comprising one or more (i.e., one, two, three, four, five, or six) characteristic X-ray powder diffraction peaks at 2θ angles of approximately 7.0, 10.8, 12.2, 14.8, 16.2, and 18.3±0.2 2θ, as depicted in FIG. 21.

In one embodiment, Solid Form B is a hydrated form. In one embodiment, Solid Form B is a non-solvated form. In another embodiment, Solid Form B is solvated form.

Figure 15:
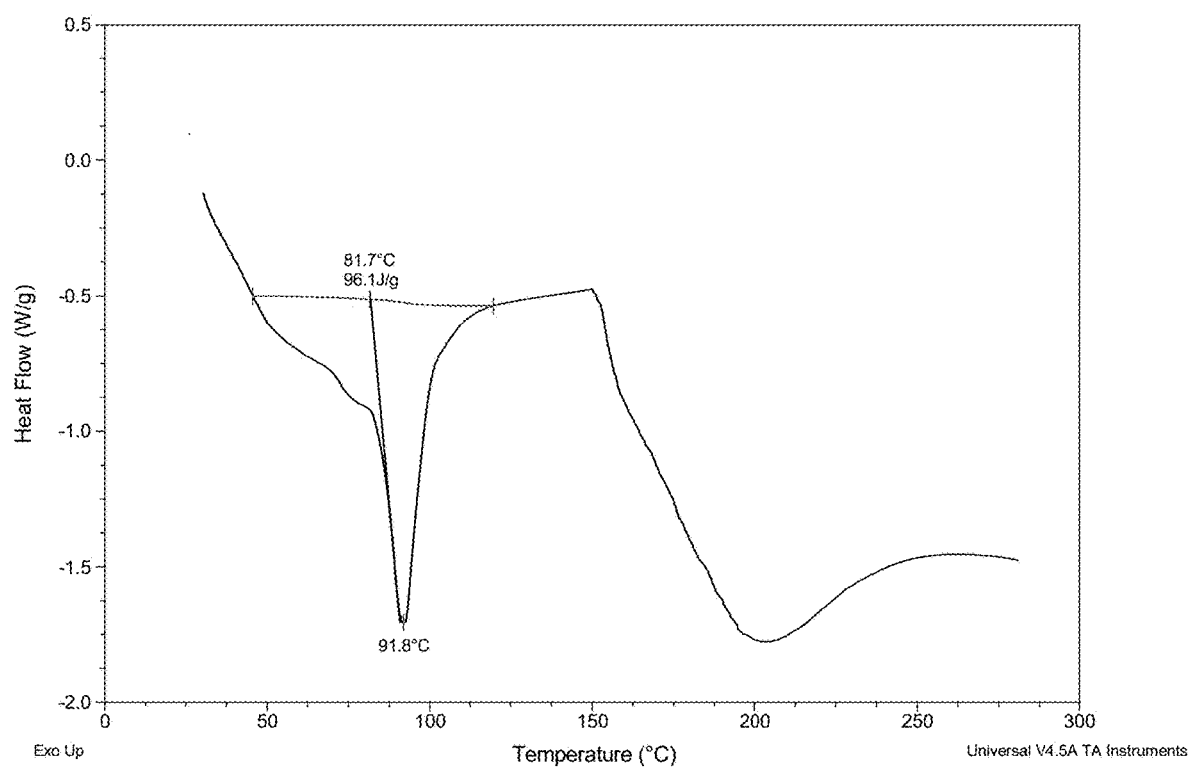
FIG. 15 depicts a representative DSC thermogram of Solid Form B of Compound 1.

In one embodiment, Solid Form B has a DSC thermograph substantially as depicted in FIG. 15. In one embodiment, DSC analysis of Solid Form B shows an endotherm with onset at 81.7° C.

In still another embodiment, Solid Form B is substantially pure. In certain embodiments, the substantially pure Solid Form B is substantially free of other solid forms, e.g., amorphous form. In certain embodiments, the purity of the substantially pure Solid Form B is no less than about 95% pure, no less than about 96% pure, no less than about 97% pure, no less than about 98% pure, no less than about 98.5% pure, no less than about 99% pure, no less than about 99.5% pure, or no less than about 99.8% pure.

(g) Solid Form C: Compound 1 and Nicotinamide

Provided herein is Solid Form C, which comprises Compound 1 and nicotinamide. In one embodiment, provided herein is a solid form comprising Solid Form C. In one embodiment, Solid Form C is a co-crystal. In one embodiment, provided herein is a solid form comprising (i) Solid Form C and (ii) an amorphous form of Compound 1. In one embodiment, provided herein is a solid form comprising (i) Solid Form C and (ii) one or more additional crystal forms of Compound 1. Provided herein are various embodiments, preparations, or modifications of a co-crystal comprising Solid Form C.

Figure 22:
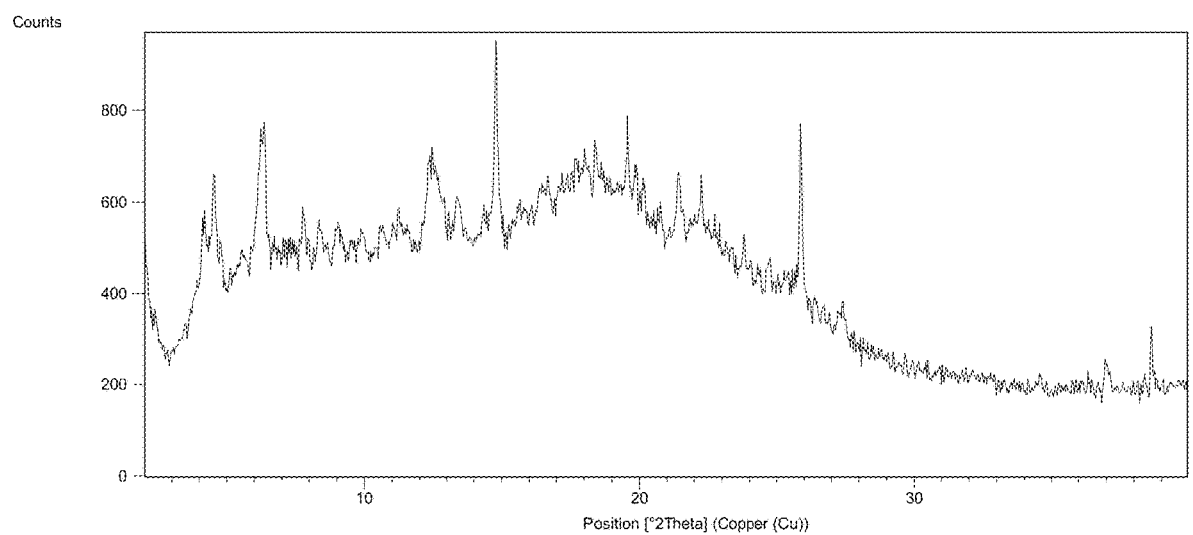
FIG. 22 depicts a representative PXRD pattern of Solid Form C of Compound 1.

In one embodiment, Solid Form C has an X-ray powder diffraction pattern substantially as shown in FIG. 22. In one embodiment, Solid Form C has an X-ray powder diffraction pattern comprising one or more (i.e., one, two, three, four, or five) characteristic X-ray powder diffraction peaks at 2θ angles of approximately 4.2, 4.5, 6.4, 14.8, and 25.9±0.2 2θ, as depicted in FIG. 22.

Figure 16:
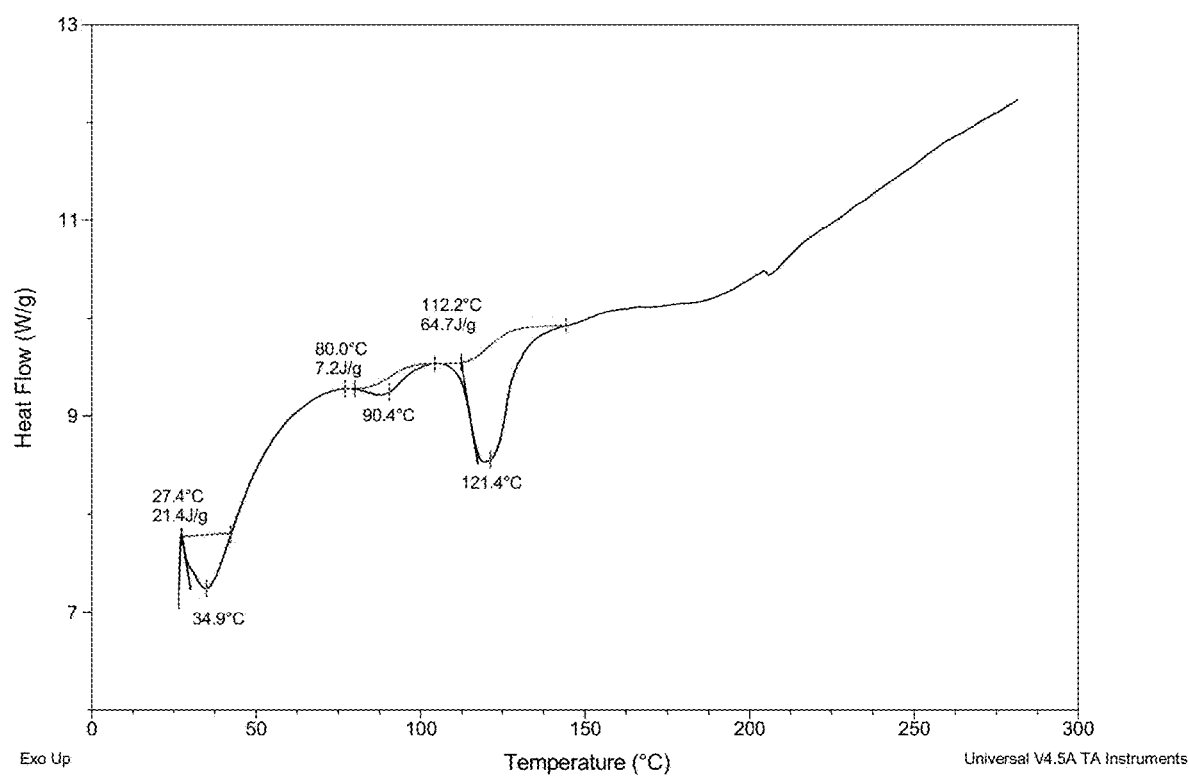
FIG. 16 depicts a representative DSC thermogram of Solid Form C of Compound 1.

In one embodiment, Solid Form C has a DSC thermograph substantially as depicted in FIG. 16. In one embodiment, DSC analysis of Solid Form C shows an endotherm with onset at about 27.4° C., an endotherm with onset at about 80.0° C., and a possible endotherm with onset at about 112.2° C.

In still another embodiment, Solid Form C is substantially pure. In certain embodiments, the substantially pure Solid Form C is substantially free of other solid forms, e.g., amorphous form. In certain embodiments, the purity of the substantially pure Solid Form C is no less than about 95% pure, no less than about 96% pure, no less than about 97% pure, no less than about 98% pure, no less than about 98.5% pure, no less than about 99% pure, no less than about 99.5% pure, or no less than about 99.8% pure.

(h) Solid Form D: Compound 1 and 1-Hydroxy-2-Naphthoic Acid

Provided herein is Solid Form D, which comprises Compound 1 and 1-hydroxy-2-naphthoic acid. In one embodiment, provided herein is a solid form comprising Solid Form D. In one embodiment, Solid Form D is a co-crystal. In one embodiment, provided herein is a solid form comprising (i) Solid Form D and (ii) an amorphous form of Compound 1. In one embodiment, provided herein is a solid form comprising (i) Solid Form D and (ii) one or more additional crystal forms of Compound 1. Provided herein are various embodiments, preparations, or modifications of Solid Form D.

In one embodiment, Solid Form D is a hydrated form. In one embodiment, Solid Form D is a non-solvated form. In another embodiment, Solid Form D is a solvated form.

Figure 17:
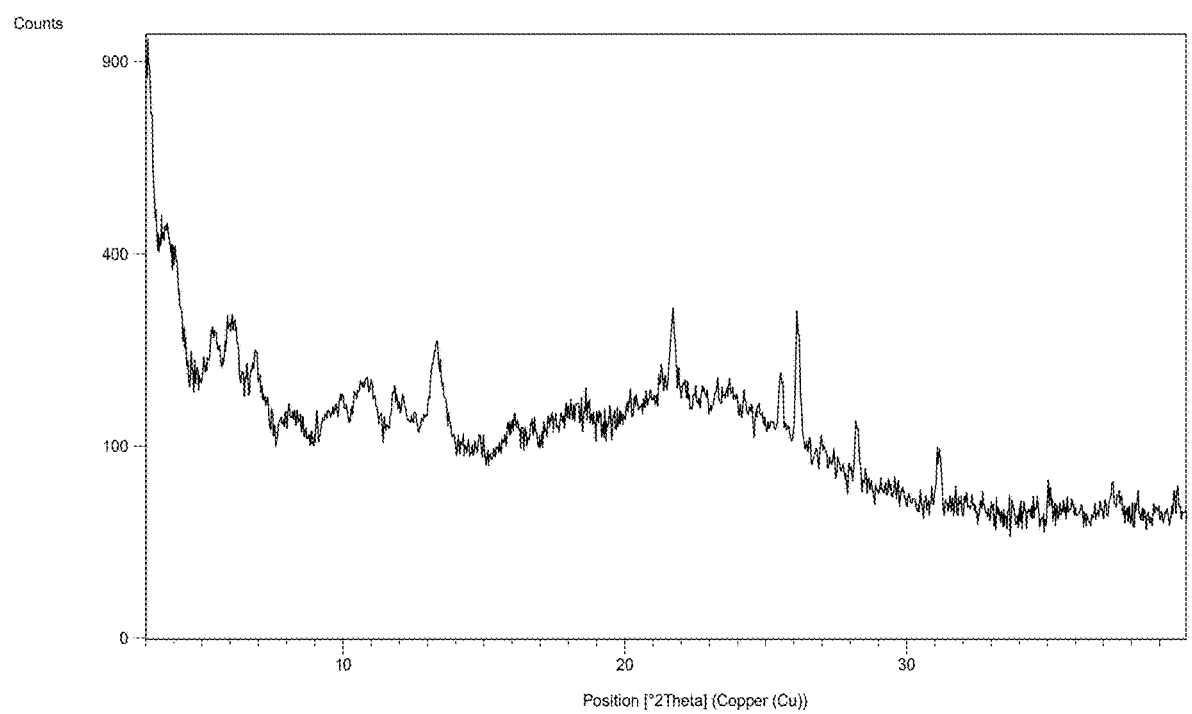
FIG. 17 depicts a representative PXRD pattern of Solid Form D of Compound 1.

In one embodiment, Solid Form D has an X-ray powder diffraction pattern substantially as shown in FIG. 17. In one embodiment, Solid Form D has an X-ray powder diffraction pattern comprising one or more (i.e., one, two, or three) characteristic X-ray powder diffraction peaks at 2θ angles of approximately 13.3, 21.7, and 26.1±0.2 2θ, as depicted in FIG. 17.

In still another embodiment, Solid Form D is substantially pure. In certain embodiments, the substantially pure Solid Form D is substantially free of other solid forms, e.g., amorphous form. In certain embodiments, the purity of the substantially pure Solid Form D is no less than about 95% pure, no less than about 96% pure, no less than about 97% pure, no less than about 98% pure, no less than about 98.5% pure, no less than about 99% pure, no less than about 99.5% pure, or no less than about 99.8% pure.

(i) Solid Form E: Compound 1 and (−)-L-Malic Acid

Provided herein is Solid Form E, which comprises Compound 1 and (−)-L-malic acid. In one embodiment, provided herein is a solid form comprising Solid Form E. In one embodiment, Solid Form E is a co-crystal. In one embodiment, provided herein is a solid form comprising (i) Solid Form E and (ii) an amorphous form of Compound 1. In one embodiment, provided herein is a solid form comprising (i) Solid Form E and (ii) one or more additional crystal forms of Compound 1. Provided herein are various embodiments, preparations, or modifications of Solid Form E.

Figure 18:
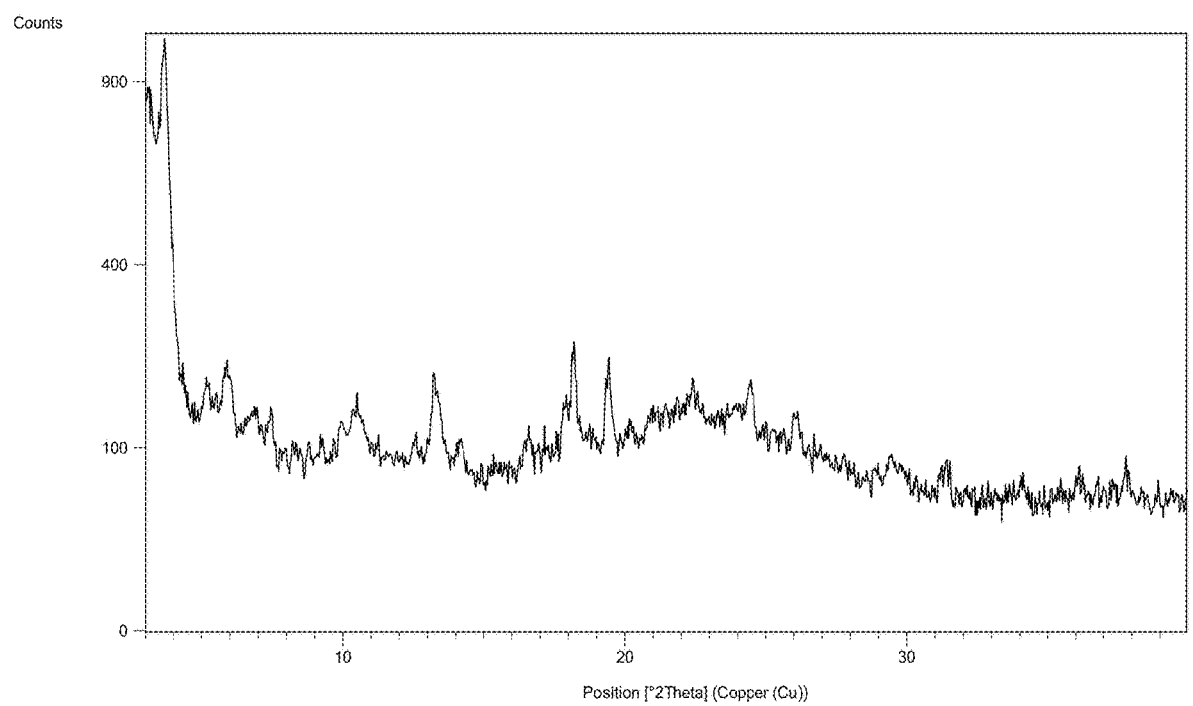
FIG. 18 depicts a representative PXRD pattern of Solid Form E of Compound 1.

In one embodiment, Solid Form E has an X-ray powder diffraction pattern substantially as shown in FIG. 18. In one embodiment, Solid Form E has an X-ray powder diffraction pattern comprising one or more (i.e., one, two, or three) characteristic X-ray powder diffraction peaks at 2θ angles of approximately 3.7, 13.3, and 18.2±0.2 2θ, as depicted in FIG. 18.

Figure 19:
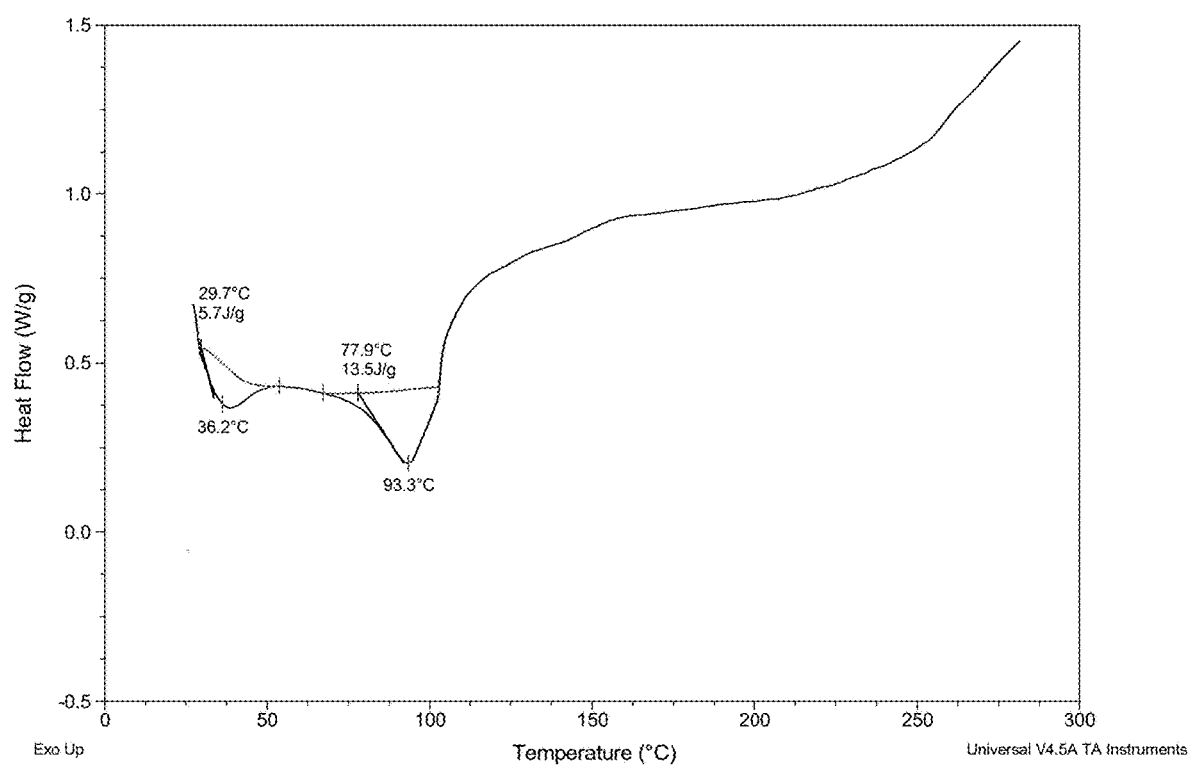
FIG. 19 depicts a representative DSC thermogram of Solid Form E of Compound 1.

In one embodiment, Solid Form E has a DSC thermograph substantially as depicted in FIG. 19. In one embodiment, DSC analysis of Solid Form E shows an endotherm with onset at about 29.7° C. and an endotherm with onset at about 77.9° C.

In still another embodiment, Solid Form E is substantially pure. In certain embodiments, the substantially pure crystal Solid Form E is substantially free of other solid forms, e.g., amorphous form. In certain embodiments, the purity of the substantially pure Solid Form E is no less than about 95% pure, no less than about 96% pure, no less than about 97% pure, no less than about 98% pure, no less than about 98.5% pure, no less than about 99% pure, no less than about 99.5% pure, or no less than about 99.8% pure.

(j) Solid Form F: Compound 1 and Urea

Provided herein is Solid Form F, which comprises Compound 1 and urea. In one embodiment, provided herein is a solid form comprising Solid Form F. In one embodiment, Solid Form F is a co-crystal. In one embodiment, provided herein is a solid form comprising (i) Solid Form F and (ii) an amorphous form of Compound 1. In one embodiment, provided herein is a solid form comprising (i) Solid Form F and (ii) one or more additional crystal forms of Compound 1. Provided herein are various embodiments, preparations, or modifications of Solid Form F.

Figure 23:
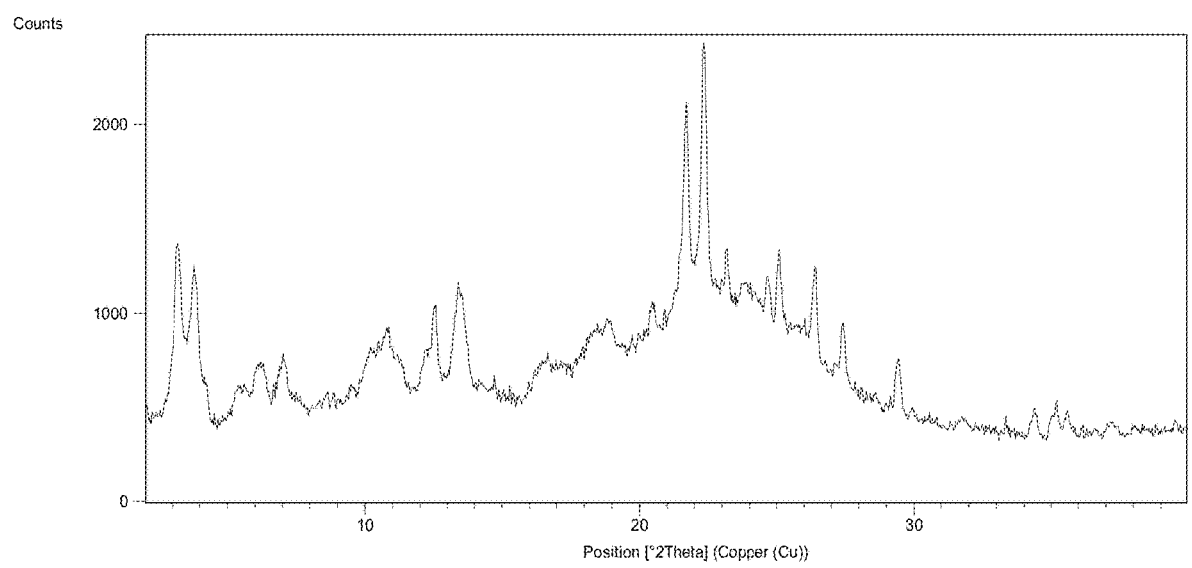
FIG. 23 depicts a representative PXRD pattern of Solid Form F of Compound 1.

In one embodiment, Solid Form F has an X-ray powder diffraction pattern substantially as shown in FIG. 23. In one embodiment, Solid Form F has an X-ray powder diffraction pattern comprising one or more (i.e., one, two, three, four, five, or six) characteristic X-ray powder diffraction peaks at 2θ angles of approximately 3.2, 12.6, 13.4, 21.7, 25.1, and 26.4±0.2 2θ, as depicted in FIG. 23.

In one embodiment, Solid Form F is a hydrated form. In one embodiment, Solid Form F is a non-solvated form. In another embodiment, Solid Form F is a solvated form.

Figure 20:
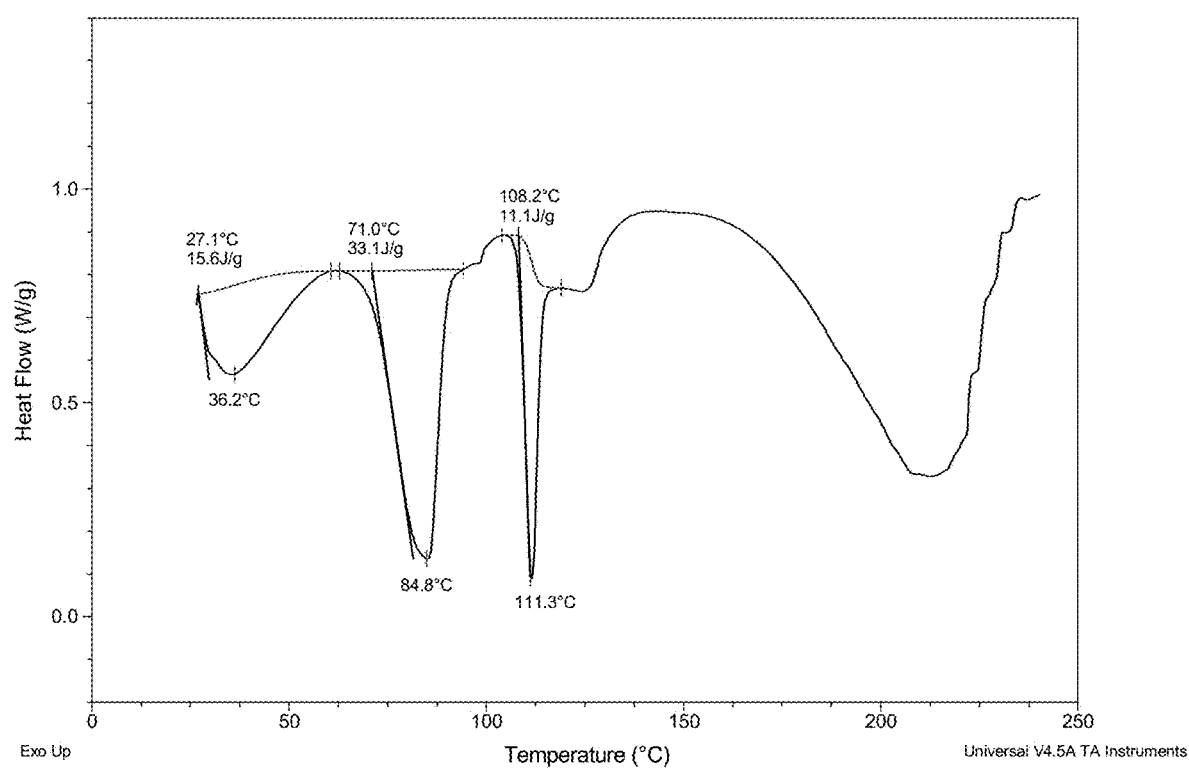
FIG. 20 depicts a representative DSC thermogram of Solid Form F of Compound 1.

In one embodiment, Solid Form F has a DSC thermograph substantially as depicted in FIG. 20. In one embodiment, DSC analysis of Solid Form F shows an endotherm with onset at 27.1° C., an endotherm with onset at 71.0° C., an endotherm with onset at 108.2° C.

In still another embodiment, Solid Form F is substantially pure. In certain embodiments, the substantially pure Solid Form F is substantially free of other solid forms, e.g., amorphous form. In certain embodiments, the purity of the substantially pure Solid Form F is no less than about 95% pure, no less than about 96% pure, no less than about 97% pure, no less than about 98% pure, no less than about 98.5% pure, no less than about 99% pure, no less than about 99.5% pure, or no less than about 99.8% pure.

(k) Solid Form G: Compound 1 and Quercetin

Provided herein is Solid Form G, which comprises Compound 1 and quercetin. In one embodiment, provided herein is a solid form comprising Solid Form G. In one embodiment Solid Form G is a co-crystal. In one embodiment, provided herein is a solid form comprising (i) Solid Form G and (ii) an amorphous form of Compound 1. In one embodiment, provided herein is a solid form comprising (i) Solid Form G and (ii) one or more additional crystal forms of Compound 1. Provided herein are various embodiments, preparations, or modifications of Solid Form G.

Figure 24:
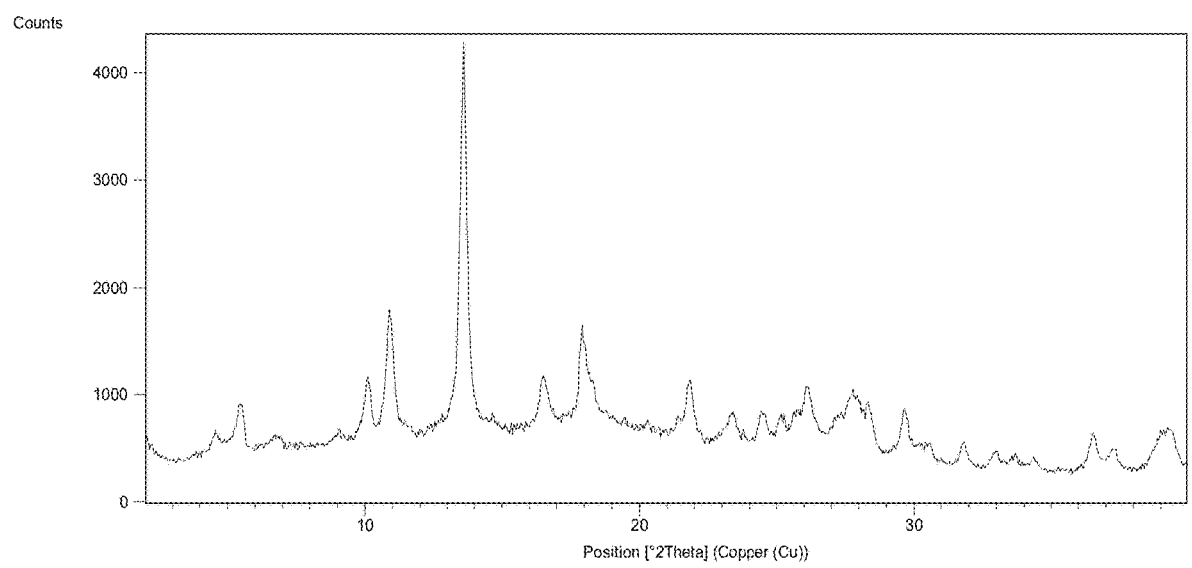
FIG. 24 depicts a representative PXRD pattern of Solid Form G of Compound 1.

In one embodiment, Solid Form G has an X-ray powder diffraction pattern substantially as shown in FIG. 24. In one embodiment, Solid Form G has an X-ray powder diffraction pattern comprising one or more (i.e., one, two, three, four, or five) characteristic X-ray powder diffraction peaks at 2θ angles of approximately 4.6, 5.6, 13.6, 17.9, 21.8±0.2 2θ, as depicted in FIG. 24.

In one embodiment, Solid Form G is a hydrated form. In one embodiment, Solid Form G is a non-solvated form. In another embodiment, Solid Form G is a solvated form.

In still another embodiment, Solid Form G is substantially pure. In certain embodiments, the substantially pure Solid Form G is substantially free of other solid forms, e.g., amorphous form. In certain embodiments, the purity of the substantially pure Solid Form G is no less than about 95% pure, no less than about 96% pure, no less than about 97% pure, no less than about 98% pure, no less than about 98.5% pure, no less than about 99% pure, no less than about 99.5% pure, or no less than about 99.8% pure.

(l) Solid Form H: Compound 1 and (+)-Camphoric Acid

Provided herein is Solid Form H, which comprises Compound 1 and (+)-camphoric acid. In one embodiment, provided herein is a solid form comprising Solid Form H. In one embodiment, Solid Form H is a co-crystal. In one embodiment, provided herein is a solid form comprising (i) Solid Form H and (ii) an amorphous form of Compound 1. In one embodiment, provided herein is a solid form comprising (i) Solid Form H and (ii) one or more additional crystal forms of Compound 1. Provided herein are various embodiments, preparations, or modifications of Solid Form H.

In one embodiment, Solid Form H is a hydrated form. In one embodiment, Solid Form H is a non-solvated form. In another embodiment, Solid Form H is a solvate.

In still another embodiment, Solid Form H is substantially pure. In certain embodiments, the substantially pure Solid Form H is substantially free of other solid forms, e.g., amorphous form. In certain embodiments, the purity of the substantially pure Solid Form H is no less than about 95% pure, no less than about 96% pure, no less than about 97% pure, no less than about 98% pure, no less than about 98.5% pure, no less than about 99% pure, no less than about 99.5% pure, or no less than about 99.8% pure.

(m) Solid Form I: Compound 1 and L-(+)-Mandelic Acid

Provided herein is Solid Form I, which comprises Compound 1 and L-(+)-mandelic acid. In one embodiment, provided herein is a solid form comprising Solid Form I. In one embodiment, Solid Form I is a co-crystal. In one embodiment, provided herein is a solid form comprising (i) Solid Form I and (ii) an amorphous form of Compound 1. In one embodiment, provided herein is a solid form comprising (i) Solid Form I and (ii) one or more additional crystal forms of Compound 1. Provided herein are various embodiments, preparations, or modifications of a co-crystal comprising Solid Form I.

In one embodiment, Solid Form I is a hydrated form. In one embodiment, Solid Form I is a non-solvated form. In another embodiment, Solid Form I is crystalline.

In still another embodiment, Solid Form I is substantially pure. In certain embodiments, the substantially pure Solid Form I is substantially free of other solid forms, e.g., amorphous form. In certain embodiments, the purity of the substantially pure Solid Form I is no less than about 95% pure, no less than about 96% pure, no less than about 97% pure, no less than about 98% pure, no less than about 98.5% pure, no less than about 99% pure, no less than about 99.5% pure, or no less than about 99.8% pure.

5.3 Evaluation of Solid Forms (a) Solubility Measurements

A weighed sample of each of co-crystal Form 1, co-crystal Form 2, co-crystal Form 3, Solid Form A, Solid Form B, Solid Form C, Solid Form D, Solid Form E, Solid Form F, Solid Form G, Solid Form H, and Solid Form I is treated with aliquots of the test solvent at ambient temperature or elevated temperature. Complete dissolution of the test material is determined by visual inspection. Solubility is estimated based on the total solvent used to provide complete dissolution of the sample. The actual solubility may be greater than the value calculated because of the use of solvent aliquots that were too large or due to a slow rate of dissolution.

(b) Stability Measurements

Stability of each of co-crystal Form 1, co-crystal Form 2, co-crystal Form 3, Solid Form A, Solid Form B, Solid Form C, Solid Form D, Solid Form E, Solid Form F, Solid Form G, Solid Form H, and Solid Form I is determined by exposing the sample to a 40° C./75% relative humidity (RH) environment for four weeks or 11% RH at ambient temperature for four days.

(c) S1P1 Assays

The compounds are useful in the treatment of a variety of S1P1 receptor-mediated clinical conditions, including diseases or disorders associated with an activated immune system; rheumatoid arthritis; lupus; insulin dependent diabetes (Type I); non-insulin dependent diabetes (Type II); multiple sclerosis; psoriasis; ulcerative colitis; inflammatory bowel disease; Crohn's disease; acute and chronic lymphocytic leukemias and lymphomas. Therefore, the compounds of the invention may be assayed for their ability to modulate the S1P1 receptor activity. Solid forms may be assayed for their ability to modulate the S1P1 receptor activity. See Colandrea, *Biorg. Med. Chem. Lett.* 2006, 16(11):2905-2908.

(i) In Vitro Binding Assay

The solid forms described herein (e.g., of co-crystal Form 1, co-crystal Form 2, co-crystal Form 3, Solid Form A, Solid Form B, Solid Form C, Solid Form D, Solid Form E, Solid Form F, Solid Form G, Solid Form H, and Solid Form I) are evaluated using a [$^{35}$S]-GTP-gamma-S binding assay to monitor dose-dependent selectivity against S1P1 receptors. The assay is completed with sample solid forms subjected to an eight-point, four-fold dose response curve with starting concentration of 10 μM. Selectivity is determined upon initial addition of solid forms followed by an incubation period. Following compound incubation, bounded [355]-GTP-gamma-S is determined by filtration and scintillation counting. Percentage activation and inhibition values are determined relative to the reference agonist at S1P1.

(ii) In Vivo Blood Lymphocyte Depletion Assay

In addition to their S1P1 binding properties, modulators of the S1P1 receptor also have accelerating lymphocyte homing properties. These properties may be measured using a blood lymphocyte depletion assay. Solid forms are administered orally by gavage to rats. Tail blood for hematological monitoring is obtained on day 1 to give the baseline individual values, and at 2, 6, 24, 48 and 72 hours after application. The change in peripheral blood lymphocytes is measured across different doses of the solid forms co-crystal Form 1, co-crystal Form 2, co-crystal Form 3, Solid Form A, Solid Form B, Solid Form C, Solid Form D, Solid Form E, Solid Form F, Solid Form G, Solid Form H, and Solid Form I.

(d) In Vitro Metabolic Disposition in Liver Microsomal Fractions

The stability of the solid forms described herein (e.g., co-crystal Form 1, co-crystal Form 2, co-crystal Form 3, Solid Form A, Solid Form B, Solid Form C, Solid Form D, Solid Form E, Solid Form F, Solid Form G, Solid Form H, and Solid Form I) is determined according to standard procedures known in the art. An in vitro hepatic microsome stability assay, for example, measures the stability of one or more subject compounds when reacting with mouse, rat or human microsomes.

Incubations with liver microsomes are conducted in a final volume of 0.1 mL per incubation time point. 10 µM of the subject solid form from a stock solution in DMSO (final DMSO concentration of 0.1%) is incubated at 37° C. from 0-60 min with pooled microsomal protein (1.0 mg/mL), suspended in incubation buffer (0.1 M potassium phosphate, pH 7.4, 5 mM $MgCl_2$, and 0.1 mM EDTA). The microsomal reaction is initiated by the addition of NADPH (3 mM final concentration). Incubations with (a) no protein or (b) no NADPH serve as controls. Reactions are terminated by the addition of 0.2 mL of stop solution (acetonitrile). The samples are vortex-mixed for 30 sec and then centrifuged at 10,000×g for 10 min. The supernatant is dried using a Labconco CentriVap concentrator and the dry residue reconstituted in water, transferred to an HPLC glass vial and analyzed by HPLC-UV. The disappearance of the subject compound is used to evaluate the in vitro metabolism thereof 5.4 Methods of Use The solid forms and the pharmaceutical compositions provided herein can be used in all the methods provided herein. The co-crystals, pharmaceutical compositions, and formulations provided herein can be used in the treatment of all diseases, disorders or conditions provided herein.

Provided herein are methods for treating a subject suffering from or at risk for having a disease or disorder associated with an activated immune system, or a disease or disorder that can be treated and/or prevented with a selective S1P1 receptor agonist, wherein the method comprises administering to said subject a solid form of Compound 1 (for example a co-crystal form of Compound 1 such as co-crystals Form 1, Form 2, or Form 3) provided herein or a pharmaceutical composition thereof.

In certain embodiments, the disease or disorder associated with an activated immune system, or a disease or disorder that can be treated and/or prevented with a selective S1P1 receptor agonist is selected from the group consisting of rejection of transplanted organs or tissue; graft-versus-host diseases brought about by transplantation; autoimmune syndromes including rheumatoid arthritis; systemic lupus erythematosus; Hashimoto's thyroiditis; lymphocytic thyroiditis; multiple sclerosis; myasthenia gravis; type I diabetes; uveitis; posterior uveitis; uveitis associated with Behcet's disease; uveomeningitis syndrome; allergic encephalomyelitis; chronic allograft vasculopathy; post-infectious autoimmune diseases including rheumatic fever and post-infectious glomerulonephritis; inflammatory and hyperproliferative skin diseases; psoriasis; atopic dermatitis; osteomyelitis; contact dermatitis; eczematous dermatitis; seborrhoeic dermatitis; lichen planus; pemphigus; bullous pemphigoid; epidermolysis bullosa; urticaria; angioedema; vasculitis; erythema; cutaneous eosinophilia; acne; alopecia areata; keratoconjunctivitis; vernal conjunctivitis; keratitis; herpetic keratitis; dystrophia epithelialis corneae; corneal leukoma; ocular pemphigus; Mooren's ulcer; ulcerative keratitis; scleritis; Graves' ophthalmopathy; Vogt-Koyanagi-Harada syndrome; sarcoidosis; pollen allergies; reversible obstructive airway disease; bronchial asthma; allergic asthma; intrinsic asthma; extrinsic asthma; dust asthma; chronic or inveterate asthma; late asthma and airway hyper-responsiveness; bronchitis; gastric ulcers; ischemic bowel diseases; inflammatory bowel diseases; necrotizing enterocolitis; intestinal lesions associated with thermal burns; coeliac diseases; proctitis; eosinophilic gastroenteritis; mastocytosis; Crohn's disease; ulcerative colitis; vascular damage caused by ischemic diseases and thrombosis; atherosclerosis; fatty heart; myocarditis; cardiac infarction; arteriosclerosis; aortitis syndrome; cachexia due to viral disease; vascular thrombosis; migraine; rhinitis; eczema; interstitial nephritis; IgA-induced nephropathy; Goodpasture's syndrome; hemolytic-uremic syndrome; diabetic nephropathy; glomerulosclerosis; glomerulonephritis; multiple myositis; Guillain-Barre syndrome; Meniere's disease; polyneuritis; multiple neuritis; mononeuritis; radiculopathy; hyperthyroidism; Basedow's disease; thyrotoxicosis; pure red cell aplasia; aplastic anemia; hypoplastic anemia; idiopathic thrombocytopenic purpura; autoimmune hemolytic anemia; agranulocytosis; pernicious anemia; megaloblastic anemia; anerythroplasia; osteoporosis; sarcoidosis; fibroid lung; idiopathic interstitial pneumonia; dermatomyositis; leukoderma vulgaris; ichthyosis vulgaris; photoallergic sensitivity; cutaneous T cell lymphoma; polyarteritis *nodosa*; Huntington's chorea; Sydenham's chorea; myocardosis; scleroderma; Wegener's granuloma; Sjogren's syndrome; adiposis; eosinophilic fascitis; lesions of gingiva, periodontium, alveolar bone, substantia ossea dentis; male pattern alopecia or alopecia *senilis*; muscular dystrophy; pyoderma; Sezary's syndrome; chronic adrenal insufficiency; Addison's disease; ischemia-reperfusion injury of organs which occurs upon preservation; endotoxin shock; pseudomembranous colitis; colitis caused by drug or radiation; ischemic acute renal insufficiency; chronic renal insufficiency; lung cancer; malignancy of lymphoid origin; acute or chronic lymphocytic leukemias; lymphoma; psoriasis; pulmonary emphysema; cataracta; siderosis; retinitis pigmentosa; senile macular degeneration; vitreal scarring; corneal alkali burn; dermatitis erythema; ballous dermatitis; cement dermatitis; gingivitis; periodontitis; sepsis; pancreatitis; carcinogenesis; metastasis of carcinoma; hypobaropathy; autoimmune hepatitis; primary biliary cirrhosis; sclerosing cholangitis; partial liver resection; acute liver necrosis; cirrhosis; alcoholic cirrhosis; hepatic failure; fulminant hepatic failure; late-onset hepatic failure; "acute-on-chronic" liver failure.

In certain embodiments, the disease or disorder is selected from the group consisting of rejection of transplanted organs such as kidney, liver, heart, lung, pancreas, cornea, and skin; graft-versus-host disease, e.g., brought about by stem cell transplantation; autoimmune syndromes including rheumatoid arthritis, multiple sclerosis, inflammatory bowel diseases such as Crohn's disease and ulcerative colitis, psoriasis, psoriatic arthritis, thyroiditis such as Hashimoto's thyroiditis, and uveo-retinitis; atopic diseases such as rhinitis, conjunctivitis, and dermatitis; asthma; type I diabetes; post-infectious autoimmune diseases including rheumatic fever and post-infectious glomerulonephritis; solid cancers; and tumor metastasis.

In certain embodiments, the disease or disorder is selected from the group consisting of rejection of transplanted organs or tissue; graft-versus-host diseases brought about by transplantation; autoimmune syndromes including rheumatoid arthritis, multiple sclerosis, myasthenia gravis; pollen allergies; type I diabetes; prevention of psoriasis; Crohn's disease; post-infectious autoimmune diseases including rheumatic fever and post-infectious glomerulonephritis; and metastasis of carcinoma.

In certain embodiments, the disease or disorder is selected from the group consisting of rejection of transplanted organs selected from kidney, liver, heart and lung; graft-versus-host diseases brought about by stem cell transplantation; autoimmune syndromes selected from rheumatoid arthritis, multiple sclerosis, psoriasis, psoriatic arthritis, Crohn's disease, and Hashimoto's thyroiditis; and atopic dermatitis.

In certain embodiments, the disease or disorder is selected from multiple sclerosis and psoriasis.

In certain embodiments, the disease or disorder is selected from multiple sclerosis and psoriasis.

In certain embodiments, the disease or disorder is moderate to severe chronic plaque psoriasis.

In certain embodiments, the disease multiple sclerosis.

In certain embodiments, the disease is selected from relapsing multiple sclerosis and relapsing-remitting multiple sclerosis.

In certain embodiments, the disease is relapsing multiple sclerosis.

In certain embodiments, the disease is relapsing-remitting multiple sclerosis.

In certain embodiments, for example, the solid form is co-crystal Form 1. In certain embodiments, for example, the solid form is co-crystal Form 2. In certain embodiments, for example, the solid form is co-crystal Form 3. In certain embodiments, for example, the solid form is Solid Form A. In certain embodiments, for example, the solid form is Solid Form B. In certain embodiments, for example, the solid form is Solid Form C. In certain embodiments, for example, the solid form is Solid Form D. In certain embodiments, for example, the solid form is Solid Form E. In certain embodiments, for example, the solid form is Solid Form F. In certain embodiments, for example, the solid form is Solid Form G. In certain embodiments, for example, the solid form is Solid Form H. In certain embodiments, for example, the solid form is Solid Form I. In certain embodiments, for example, a treatment for multiple sclerosis comprises administration of one solid form of Compound 1 with at least one other form. In certain embodiments, for example, the at least one other form comprises another form of Compound 1 (for example a non-co-crystal form of Compound 1, e.g., an amorphous form of Compound 1).

Provided herein are methods for treating a subject suffering from or at risk for having a disease or disorder associated with sphingosine 1-phosphate. In certain embodiments, the method for treating a subject suffering from or at risk of having a disease or disorder associated with disease or disorder associated with sphingosine 1-phosphate comprises administering a solid form of Compound 1. In certain embodiments, for example, the solid form is co-crystal Form 1. In certain embodiments, for example, the solid form is co-crystal Form 2. In certain embodiments, for example, the solid form is co-crystal Form 3. In certain embodiments, for example, the solid form is Solid Form A. In certain embodiments, for example, the solid form is Solid Form B. In certain embodiments, for example, the solid form is Solid Form C. In certain embodiments, for example, the solid form is Solid Form D. In certain embodiments, for example, the solid form is Solid Form E. In certain embodiments, for example, the solid form is Solid Form F. In certain embodiments, for example, the solid form is Solid Form G. In certain embodiments, for example, the solid form is Solid Form H. In certain embodiments, for example, the solid form is Solid Form I. In certain embodiments, for example, a treatment for a disease or disorder associated with sphingosine 1-phosphate comprises administration of one solid form of Compound 1 with at least one other form. In certain embodiments, for example, the at least one other form comprises another form of Compound 1 (for example a non-co-crystal form of Compound 1 e.g., an amorphous form of Compound 1).

5.5 Pharmaceutical Compositions

Provided herein are pharmaceutical compositions comprising solid forms of Compound 1 provided herein (e.g., co-crystal Form 1, co-crystal Form 2, co-crystal Form 3, Solid Form A, Solid Form B, Solid Form C, Solid Form D, Solid Form E, Solid Form F, Solid Form G, Solid Form H, and Solid Form I). In one embodiment, the compositions provided herein may comprise a co-crystal of Compound 1 and may further comprise a crystal form of Compound 1, an amorphous form of Compound 1, or mixtures thereof (e.g., mixtures of crystal forms, or mixtures of crystal and amorphous forms). In one embodiment, provided herein is a composition comprising a co-crystal of Compound 1, i.e., (a) Compound 1; and (b) a coformer. In one embodiment, provided herein is a mixture comprising (i) a co-crystal of Compound 1; and (ii) a crystal form of Compound 1. In one embodiment, provided herein is a mixture comprising (i) a co-crystal of Compound 1; and (ii) an amorphous form of Compound 1.

In certain embodiments, the pharmaceutical compositions comprise a single solid form of Compound 1, e.g., a solid form selected from the group consisting of co-crystal Form 1, co-crystal Form 2, co-crystal Form 3, Solid Form A, Solid Form B, Solid Form C, Solid Form D, Solid Form E, Solid Form F, Solid Form G, Solid Form H, and Solid Form I. In certain embodiments, the pharmaceutical compositions comprise a mixture of solid forms of Compound 1. In some embodiments, the pharmaceutical compositions comprise at least one of co-crystal Form 1, co-crystal Form 2, co-crystal Form 3, Solid Form A, Solid Form B, Solid Form C, Solid Form D, Solid Form E, Solid Form F, Solid Form G, Solid Form H, and Solid Form I. In some embodiments, the pharmaceutical compositions comprise at least one of co-crystal Form 1, co-crystal Form 2, co-crystal Form 3, Solid Form A, Solid Form B, Solid Form C, Solid Form D, Solid Form E, Solid Form F, Solid Form G, Solid Form H, and Solid Form I; and an additional form of Compound 1, e.g., any of the forms described above in Section 5.3, e.g., a solvated form, amorphous form, and the like.

In one embodiment, provided herein are pharmaceutical formulations comprising an effective amount of a solid form of Compound 1 and a pharmaceutically acceptable vehicle, carrier, diluent, or excipient, or a mixture thereof. In certain embodiments, the pharmaceutically acceptable carrier is hydroxypropyl methylcellulose. In some embodiments, the pharmaceutical compositions described herein are suitable for oral, parenteral, mucosal, transdermal or topical administration. In certain embodiments, the solid form of Compound 1 is selected from the group consisting of co-crystal Form 1, co-crystal Form 2, co-crystal Form 3, Solid Form A, Solid Form B, Solid Form C, Solid Form D, Solid Form E, Solid Form F, Solid Form G, Solid Form H, and Solid Form I. In certain embodiments, the pharmaceutical formulations comprise a mixture of solid forms of Compound 1 and a pharmaceutically acceptable vehicle, carrier, diluent, or excipient, or a mixture thereof. In some embodiments, the pharmaceutical formulations comprise at least one of co-crystal Form 1, co-crystal Form 2, co-crystal Form 3, Solid Form A, Solid Form B, Solid Form C, Solid Form D, Solid Form E, Solid Form F, Solid Form G, Solid Form H, and Solid Form I; and a pharmaceutically acceptable vehicle, carrier, diluent, or excipient, or a mixture thereof. In some embodiments, the pharmaceutical formulations comprise at least one of co-crystal Form 1, co-crystal Form 2, co-crystal Form 3, Solid Form A, Solid Form B, Solid Form C, Solid Form D, Solid Form E, Solid Form F, Solid Form G, Solid Form H, and Solid Form I; an additional form of Compound 1, e.g., any of the forms described above in Section 5.3, e.g., a solvated form, amorphous form, and the like; and a pharmaceutically acceptable vehicle, carrier, diluent, or excipient, or a mixture thereof. co-crystal 5.6 Additional Active Pharmaceutical Ingredients (APIs)

In certain embodiments, the compositions or formulations described herein can be combined with one or more additional active pharmaceutical ingredients. In certain embodiments, the additional active can be selected from the group comprising or consisting of immunosuppressants, corticosteroids, nonsteroidal anti-inflammatory drugs, cytotoxic drugs, adhesion molecule inhibitors, cytokines, cytokine inhibitors, cytokine receptor antagonists and recombinant cytokine receptors. In certain embodiments, the additional active can be an immunosuppressant agent. In certain embodiments, the additional active can be selected from the group consisting of cyclosporin, daclizumab, basiliximab, everolimus, tacrolimus (FK506), azathiopirene, leflunomide, and 15-deoxyspergualin.

In certain embodiments, the additional active can be selected from the group consisting of methyl fumarate, dimethyl fumarate, (N,N-diethylcarbamoyl)methyl methyl (2E)but-2-ene-1,4-dioate, and 2-(2,5-dioxopyrrolidin-1-yl) ethyl methyl (2E)but-2-ene-1,4-dioate, or a pharmaceutically acceptable salt thereof.

In certain embodiments, the additional active pharmaceutical ingredient can be administered simultaneously, separately, or sequentially with the co-crystals and/or other solid forms of Compound 1. In certain embodiments, the additional active pharmaceutical ingredient can be administered simultaneously, separately, or sequentially with the pharmaceutical compositions, and pharmaceutical formulations disclosed herein. In certain embodiments, the additional active pharmaceutical ingredient can be administered simultaneously in the same dosage form. In certain embodiments, the additional active pharmaceutical ingredient can be administered simultaneously in the separate dosage forms. In certain embodiments, the additional active pharmaceutical ingredient can be administered separately from the co-crystals and/or other solid forms, pharmaceutical compositions, and pharmaceutical formulations disclosed herein 5.7 Oral Administration The pharmaceutical compositions provided herein may be administered orally, for example in solid, semisolid, or liquid dosage forms. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

In one embodiment, the pharmaceutically acceptable carrier or excipient is selected from the group consisting of lactose (e.g., as lactose monohydrate); microcrystalline cellulose; non-basic polymers (e.g., homopolymers of cross-linked N-vinyl-2-pyrrolidone (crospovidone), hypromellose (hydroxypropylmethyl cellulose), and ethyl cellulose); waxes; colloidal silicon dioxide; stearic acid; hydrogenated vegetable oil; mineral oil; polyethylene glycol (e.g., polyethylene glycol 4000-6000); glyceryl palmitostearate; and glyceryl behenate. In another embodiment, the pharmaceutically acceptable carrier or excipient is microcrystalline cellulose.

Binders or granulators impart cohesiveness to a tablet to ensure the tablet remains intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The pharmaceutical compositions provided herein may contain from about 0.5% to about 15% or from about 1% to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1% to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic acid, sodium benzoate, and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

5.8 Parenteral Administration

The pharmaceutical compositions provided herein can be administered parenterally, for example, by injection, infusion, or implantation techniques, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, e.g., *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfate and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

5.9 Dosing Regmines

In certain embodiments, a dose of Compound 1 in the pharmaceutical composition is between about 0.1 mg and about 1000 mg per day. In certain embodiments, the dose is between about 0.1 mg and about 500 mg per day. In certain embodiments, the dose is between about 0.5 mg and about 500 mg per day. In certain embodiments, the dose is between about 0.1 mg and about 200 mg per day. In certain embodiments, the dose is between about 0.1 mg and about 100 mg per day. In certain embodiments, the dose is between about 0.1 mg and about 50 mg per day. In certain embodiments, the dose is between about 0.1 mg and about 30 mg per day. In certain embodiments, the dose is between about 0.1 mg and about 20 mg per day. In certain embodiments, the dose is between about 0.5 mg and about 20 mg per day. In certain embodiments, the dose is between about 1 mg and about 20 mg per day. In certain embodiments, the dose is between about 1 mg and about 15 mg per day. In certain embodiments, the dose is between about 1 mg and about 10 mg per day. In certain embodiments, the dose is between about 1 mg and about 5 mg per day. In certain embodiments, the dose is between about 1 mg and about 500 mg per day. In certain embodiments, the dose is between about 5 mg and about 200 mg per day.

In certain embodiments, a maintenance dose of Compound 1 in the pharmaceutical composition is between about 0.1 mg and about 20 mg orally once daily. In certain embodiments, the maintenance dose is between about 0.5 mg and about 20 mg orally once daily. In certain embodiments, the maintenance dose is between about 0.1 mg and about 15 mg orally once daily. In certain embodiments, the maintenance dose is between about 0.5 mg and about 15 mg orally once daily. In certain embodiments, the maintenance dose is between about 0.1 mg and about 10 mg orally once daily. In certain embodiments, the maintenance dose is between about 0.5 mg and about 10 mg orally once daily. In certain embodiments, the maintenance dose is between about 0.1 mg and about 5 mg orally once daily. In certain embodiments, the maintenance dose is between about 0.5 mg and about 5 mg orally once daily.

In certain embodiments, a maintenance dose of Compound 1 in the pharmaceutical composition is about 10 mg or about 20 mg orally once daily. In certain embodiments, the maintenance dose is about 20 mg orally once daily. In certain embodiments, the maintenance dose is 20 mg once daily. In certain embodiments, the maintenance dose is 20 mg administered as a monotherapy.

In certain embodiments, Compound 1 can be administered orally once daily a dose of about 10 mg for 7 days followed by about 20 mg on day 8.

In certain embodiments, the dosing regimen can comprise administration of: about 2 mg of Compound 1 on days 1 and 2; about 3 mg on days 3 and 4; about 4 mg on days 5 and 6; about 5 mg of the on day 7; about 6 mg on day 8; about 7 mg of on day 9; about 8 mg on day 10; and about 9 mg on day 11; followed by: (a) a maintenance dose of about 10 mg of Compound 1 administered orally once daily from day 12 onwards; or (b) about 10 mg administered orally once daily for 2, 3 or 4 days (i.e., on days 12 and 13; days 12, 13, and 14; or days 12, 13, 14, and 15), or for 3 days (i.e., on days 12, 13, and 14), followed by a maintenance dose of about 20 mg administered orally once daily (i.e., from the day following the day of the last administration of the about 10 mg dose onwards).

In certain embodiments, the dosing regimen can comprise administration of: about 2 mg of Compound 1 on days 1 and 2; about 3 mg on days 3 and 4; about 4 mg on days 5 and 6; about 5 mg on day 7; about 6 mg on day 8; about 7 mg on day 9; about 8 mg on day 10; and about 9 mg on day 11; followed by about 10 mg of Compound 1 administered orally once daily for 2, 3 or 4 days; followed by the maintenance dose of about 20 mg administered orally once daily.

In certain embodiments, about 10 mg of Compound 1 can be administered orally once daily on days 12, 13, and 14; followed by a maintenance dose of 20 mg administered orally once daily from day 15 onwards.

In certain embodiments, the dosing regimen can comprise administration of: about 2 mg of Compound 1 on days 1 and 2; about 3 mg on days 3 and 4; about 4 mg on days 5 and 6; about 5 mg on day 7; about 6 mg on day 8; about 7 mg day 9; about 8 mg on day 10; and about 9 mg on day 11; followed by the maintenance dose of about 10 mg of Compound 1 administered orally once daily from day 12 onwards.

For clarity reasons, it is noted that the doses referred to herein refer to the amount of the Compound 1 in its free form. In case that for example a pharmaceutically acceptable salt of the Compound 1 is used, the amounts given above will need to be adapted accordingly. Additionally, the dose of Compound 1 referred to herein indicates the total dose of all forms of Compound 1 in the pharmaceutical composition.

The compounds, compositions, methods, and uses disclosed herein are not to be limited in scope by the specific embodiments described herein. For example, all disclosed compounds can be in their free base form, or a pharmaceutically acceptable salt, hydrate, solvate, clathrate, prodrug, or polymorph thereof. Indeed, various modifications of the compounds, compositions, methods, and uses in addition to those described will become apparent to those skilled in the art from the foregoing description. Such modifications are intended to fall within the scope of the appended claims.

Various publications, patents and patent applications are cited herein, the disclosures of which are incorporated by reference in their entities.

6. EXAMPLES

The following Examples are presented by way of illustration, not limitation.

Examples

Co-crystals Form 1, Form 2, and Form 3 were prepared by slurry ripening as described in Table 1 and tested as shown in Table 2.

TABLE 1

Slurry Ripening Procedure for Preparation of Forms 1-3 of Compound 1

| Step | Form 1 | Form 2 | Form 3 |
|---|---|---|---|
| Preparing a coformer-saturated solvent | Methyl tert-butyl ether solvent saturated with L-prolinamide | Ethyl acetate/heptane (2:8 v/v) solvent saturated with pyrogallol | Ethanol solvent saturated with aspartame |
| Combining with coformer and mixing with the coformer-saturated solvent. | Combine 307.7 mg Compound 1 with 72.1 mg coformer and mix with 1.5 mL of the solvent for 30 min. at 25° C. | Combine 306.9 mg Compound 1 with 79.6 mg coformer and mix with 0.9 mL of the solvent for 30 min. at 25° C. | Combine 410.8 mg Compound 1 with 248.7 mg coformer and mix with 8 mL of the solvent for 30 min. at 25° C. |
| Seeding | Seed and mix for 1 hr. at 25° C. | Seed and mix with spatula, add 1.4 mL of the solvent, and cycle temperature (25-5° C. with 0.1° C. slow cool) with mixing for 3 days | Seed and cycle temperature 35-5° C. with 0.1° C. slow cool) with mixing for 2 days |
| Ripening | Add 5.5 mL of the solvent solution and mix for 1 hr. at 25° C., followed by cycling temperature (35-20° C. with 0.1° C. slow cool) with mixing for 44 hrs., followed by cycling temperature (25-5° C. 1 hr. at each temperature) with mixing for 3 days. | Add 2 mL of the solvent and mix for 1 hr. at 25° C., followed by cycling temperature (25-5° C. with 0.1° C./min slow cool) with mixing for 4 hrs. | Add 5 mL of the solvent and mix for 2 hrs. at 25° C. |
| Isolation | Vacuum filtration followed by air drying for 18 hours to yield 235 mg Form 1. | Vacuum filtration followed by air drying for 18 hours to yield 306 mg Form 2. | Vacuum filtration followed by air drying for 19 hours to yield 486 mg Form 3. |

TABLE 2

Testing of Forms 1-3 of Compound 1.

| Form | PXRD[1] | FT-Raman Spectroscopy[2] | DSC[3] | TGA & TGA-IR[4,5] | Stoichiometry by 1H NMR[6] (Compound 1:Coformer) | PLM[7] |
|---|---|---|---|---|---|---|
| 1 | Table 3 & FIG. 1 | FIG. 2 | FIG. 3 Melting endotherm with onset at 94.8° C. | FIG. 3 0.8% weight loss between 25° C. and 115.6° C. (non-solvated) | 1:1.1 | FIG. 4 |

TABLE 2-continued

Testing of Forms 1-3 of Compound 1.

| Form | PXRD[1] | FT-Raman Spectroscopy[2] | DSC[3] | TGA & TGA-IR[4,5] | Stoichiometry by 1H NMR[6] (Compound 1:Coformer) | PLM[7] |
|---|---|---|---|---|---|---|
| 1 | Table 3 & FIG. 5 | FIG. 6 | FIG. 7 Melting endotherm with onset at 96.4° C. | FIG. 7 0.1% weight loss between 25.9° C. and 119.8° C. (non-solvated) | 1:1.2 | FIG. 8 |
| 1 | Table 3 & FIG. 9 | FIG. 10 | FIG. 11 Dehydration endotherm with onset at 33.3° C. Melting endotherm with onset at 106.7° C. Decomposition endotherm with onset at 136.2° C. | FIG. 11 2.4% weight loss of water between 26.8° C. and 102.4° C., followed by 4.5% weight loss of methanol | 1:1.2 | FIG. 12 |

[1]Powder X-Ray Diffraction (PXRD). PXRD diffractograms were acquired on PANalytical X'Pert Pro diffractometer using Ni-filtered Cu Kα (45 kV/40 mA) radiation and a step size of 0.03° 2θ and X'celerator ™ RTMS (Real Time Multi-Strip) detector. Configuration on the incidental beam side: variable divergence slits (10 mm irradiated length), 0.04 rad Soller slits, fixed anti-scatter slit (0.25°), and 10 mm beam mask. Configuration on the diffracted beam side: variable anti-scatter slit (10 mm observed length) and 0.02 rad Sollerslit. Samples were mounted flat on zero-background Si wafers. Alternatively, PXRD diffractograms were acquired on a Bruker D8 Advance system (SN:2631) using Cu Kα (40 kV/40 mA) radiation and a step size of 0.017° 2θ and LynxEye detector. Configuration on the incidental beam side: fixed divergence slit (0.2 mm), 4 mm Soller slits, beam knife. Configuration on the diffracted beam side: anti- scatter slit (8 mm) and 2.5 deg. Soller slit. Samples were mounted flat on zero-background Si wafers.
[2]FT-Raman Spectroscopy. Raman spectra were collected with a Nicolet NXR9650 or NXR 960 spectrometer (Thermo Electron) equipped with 1064 nm Nd:YVO$_4$ excitation laser, InGaAs and liquid-N$_2$ cooled Ge detectors, and a MicroStage. All spectra were acquired at 4 cm$^{-1}$ resolution, 64 scans, using Happ- Genzel apodization function and 2-level zero-filling.
[3]Differential Scanning Calorimetry (DSC). DSC was conducted with a TA Instruments Q100 differential scanning calorimeter equipped with an autosampler and a refrigerated cooling system under 40 mL/min N$_2$ purge. DSC thermograms were obtained at 15° C./min in crimped Al pans.
[4]Thermogravimetric Analysis (TGA). TGA thermograms were obtained with a TA Instruments Q50 thermogravimetric analyzer under 40 mL/min N2 purge in Al pans. TGA thermograms of screening samples were obtained at 15° C./min, unless noted otherwise. TGA thermograms of input and scaled-up material were obtained at 10° C./min.
[5]Thermogravimetric Analysis with IR Off-Gas Detection (TGA-IR). TGA-IR was conducted with a TA Instruments Q5000 thermogravimetric analyzer interfaced to a Nicolet 6700 FT-IR spectrometer (Thermo Electron) equipped with an external TGA-IR module with a gas flow cell and DTGS detector. TGA was conducted with 25 mL/min N$_2$ flow and heating rate of 10° C./min or 15° C./min in Al pans. IR spectra were collected at 4 cm$^{-1}$ resolution and 32 scans at each time point.
[6]Proton Nuclear Magnetic Resonance (1H NMR). 1H NMR spectra were collected using an Agilent DD2 500 MHz spectrometer with tetramethylsilane reference. Samples were dissolved in deuterated dimethyl sulfoxide.
[7]Polarized Light Microscopy (PLM). The PLM photomicrographs were collected using an Olympus BX60 polarized-light microscope equipped with Olympus DP70 camera.

TABLE 3

Powder X-Ray Diffraction Peaks for Forms 1-3 of Compound 1.

| Form 1 | | | Form 2 | | | Form 3 | | |
|---|---|---|---|---|---|---|---|---|
| 2Theta (°) | d Space (Å) | Height (counts) | 2Theta (°) | d Space (Å) | Height (counts) | 2Theta (°) | d Space (Å) | Height (counts) |
| 6.8 | 12.915 | 13335 | 6.0 | 14.747 | 2131 | 5.0 | 17.748 | 249 |
| 11.2 | 7.899 | 7457 | 7.7 | 11.417 | 981 | 5.9 | 15.058 | 200 |
| 12.7 | 6.959 | 1943 | 9.9 | 8.892 | 377 | 6.2 | 14.228 | 226 |
| 13.1 | 6.755 | 2368 | 12.0 | 7.384 | 702 | 6.7 | 13.285 | 1043 |
| 15.2 | 5.845 | 1039 | 13.1 | 6.749 | 426 | 7.3 | 12.179 | 974 |
| 15.6 | 5.664 | 2027 | 14.8 | 5.974 | 273 | 8.1 | 10.945 | 328 |
| 16.7 | 5.319 | 2438 | 15.5 | 5.707 | 663 | 11.7 | 7.554 | 1336 |
| 19.4 | 4.575 | 7978 | 16.1 | 5.520 | 364 | 12.8 | 6.900 | 356 |
| 20.5 | 4.339 | 1924 | 18.4 | 4.824 | 186 | 14.2 | 6.257 | 361 |
| 21.4 | 4.151 | 6109 | 19.8 | 4.481 | 686 | 17.7 | 5.007 | 1006 |
| 22.9 | 3.881 | 1128 | 22.0 | 4.038 | 335 | 18.7 | 4.733 | 224 |
| 23.8 | 3.737 | 1212 | 23.3 | 3.811 | 535 | 22.2 | 4.008 | 485 |
| 25.5 | 3.497 | 1514 | 24.5 | 3.633 | 374 | | | |
| 26.0 | 3.431 | 2553 | 25.6 | 3.477 | 240 | | | |
| | | | 26.5 | 3.361 | 301 | | | |
| | | | 28.3 | 3.155 | 363 | | | |
| | | | 28.8 | 3.102 | 175 | | | |

Other Solid Forms

A series of comparative crystallization experiments were conducted with 41 potential coformers and 7 solvents by two different methods. Results are presented in Tables 4 and 5. As shown, Forms 1-3 were detected in experiments with L-prolinamide, pyrogallol, and aspartame, respectively. Poorly crystalline results were obtained between Compound 1 and citric acid (Solid Form A), Compound 1 and nicotinamide (Solid Forms B and C), Compound 1 and 1-hydroxy-2-naphthoic acid (Solid Form D), Compound 1 and (−)-L-malic acid (Solid Form E), Compound 1 and urea (Solid Form F), Compound 1 and quercetin (Solid Form G), Compound 1 and (+)-camphoric acid (Solid Form H), and Compound 1 and L-(+)-mandelic acid (Solid Form I). Solid Forms A-G were tested as shown in Table 6. The remaining experiments did not yield potential co-crystals.

TABLE 4

Solvent-Drop Grinding Results of the Comparative Experiments.[1]

| # | CCF | EtOH | | EtOAc | | MTBE | | MeCN/Water (1:9) | |
|---|---|---|---|---|---|---|---|---|---|
| 1 | L-Aspartic acid | AM | CF | AM | CF | AM | CF | AM | CF |
| 2 | Maleic acid | AM | AM | AM | CF | AM | AM | PB | PB |
| 3 | L-Glutamic acid | AM | CF | AM | CF | AM | CF | AM | CF |
| 4 | Pamoic acid | AM | CF | PA | CF | AM | CF | AM | CF |
| 5 | 1-Hydroxy-2-Naphthoic acid | AM | CF | PA | CF | AM | CF | AM | CF |
| 6 | Malonic acid | AM | CF | PA | CF | AM | AM | PB* | PB* |
| 7 | Gentisic acid | AM | CF | AM | CF | AM | CF | PB | CF |
| 8 | (+)-L-Tartaric acid | AM | CF | AM | CF | AM | CF | AM | CF |
| 9 | Fumaric acid | AM | CF | AM | CF | AM | CF | AM | CF |
| 10 | Citric acid | AM | CF | AM | CF | AM | CF | PCH | PCH |
| 11 | (−)-L-Malic acid | AM | CF | AM | CF | AM | CF | PB* | PB* |
| 12 | Hippuric acid | AM | CF | AM | CF | AM | CF | AM | CF |
| 13 | L-Ascorbic acid | AM | CF | PA | CF | AM | CF | AM | CF |
| 14 | Benzoic acid | AM | CF | AM | CF | AM | CF | PB | CF |
| 15 | Succinic acid | AM | CF | AM | CF | AM | CF | PB | CF |
| 16 | Glutaric acid | PA | CF | PA | CF | | CF | PA | CF |
| 17 | (+)-Camphoric acid | AM | CF | AM | CF | AM | CF | PB | CF |
| 18 | Nicotinic acid | AM | CF | AM | CF | AM | CF | PA | CF |
| 19 | Orotic acid | AM | CF | PA | CF | AM | CF | PA | CF |
| 20 | L-(+)-Mandelic acid | AM | CF | PA | CF | AM | CF | PB | CF |
| 21 | 2-Aminobenzoic acid | AM | CF | AM | CF | AM | CF | PB | CF |
| 22 | Gallic acid | AM | CF | AM | CF | AM | CF | AM | CF |
| 23 | Urea | AM | CF | AM | CF | AM | CF | AM | CF |
| 24 | Caffeine | AM | CF | AM | CF | AM | CF | AM | CF |
| 25 | Nicotinamide | AM | CF | AM | CF | AM | CF | PCH | CF |
| 26 | Isonicotinamide | AM | CF | AM | CF | AM | CF | AM | CF |
| 27 | L-Prolinamide | PCHA | PCHA | PCHA | CF | AM | CF | PCHA | PCHA |
| 28 | Vanillin | PA | CF | PA | CF | PA | CF | PB | CF |
| 29 | Methyl paraben | AM | CF | AM | CF | AM | CF | PB | CF |
| 30 | Propyl paraben | PA | CF | AM | CF | PA | CF | PB | CF |
| 31 | Butylated hydroxyanisole | AM | CF | AM | CF | AM | | AM | CF |
| 32 | Pyrogallol | PA | CF | PA | CF | PA | CF | AM | CF |
| 33 | Chrysin | PA | CF | PA | CF | AM | CF | PA | CF |
| 34 | Resveratrol | AM | CF | PA | CF | AM | CF | PB | CF |
| 35 | Quercetin | PA | CF | PA | CF | AM | CF | AM | CF |
| 36 | Saccharin | AM | CF | AM | CF | AM | CF | PB | CF |
| 37 | Aspartame | AM | CF | AM | CF | AM | CF | AM | CF |
| 38 | Xylitol | AM | CF | PA | CF | AM | CF | AM | CF |
| 39 | Sucralose | AM | CF | AM | CF | AM | CF | AM | CF |
| 40 | D-Mannitol | AM | CF | PA | CF | AM | CF | AM | CF |

TABLE 4-continued

Solvent-Drop Grinding Results of the Comparative Experiments.[1]

| # | CCF | EtOH | | EtOAc | | MTBE | | MeCN/ Water (1:9) | |
|---|---|---|---|---|---|---|---|---|---|
| 41 | DL-Mandelic acid | AM | CF | AM | CF | AM | CF | P B | CF |

Legend:
AM: amorphous
P = parent
PCH = poorly crystalline hit
* = poorly crystalline
CH = crystalline hit
CF = coformer
A, B = crystal forms

[1]Approximately 100 mg Compound 1 was combined with molar equivalent amounts of coformer and 2-15 μL solvent in a 10 mL stainless steel milling jar and milled at room temperature on a Retsch Mill (Model MM301) performed at 20 Hz for 15 minutes using one mill ball.

TABLE 5

Slurry Ripening Results of the Comparative Experiments.[1]

| # | CCF | EtOH | | EtOAc | | MTBE | | MeCN/ Water (1:9) | | 1-Butanol | | Toluene | |
|---|---|---|---|---|---|---|---|---|---|---|---|---|---|
| 1 | L-Aspartic acid | P H | CF | P F | CF | P A | CF | P B | CF | P | CF | P F | CF |
| 2 | Maleic acid | P H | CF | AM | AM | AM | AM | P B | P B | P H | CF | P F | CF |
| 3 | L-Glutamic acid | P B | CF | P | CF | P A | CF | P B | CF | P H | CF | P F | CF |
| 4 | Pamoic acid | P H | CF | P A | CF | P H | P H | P B | CF | P H | CF | P F | CF |
| 5 | 1-Hydroxy-2-Naphthoic acid | P H | CF | PCH | PCH | P A* | CF | P B | CF | AM | CF | P F | CF |
| 6 | Malonic acid | AM | AM | AM | AM | AM | AM | P B | P B | P E | P E | P F | P F* |
| 7 | Gentisic acid | P H | P H | AM | AM | P A | CF | P B | P H | P B | CF | P F | CF |
| 8 | (+)-L-Tartaric acid | P H | P H | P F* | CF | P A | CF | P B | P B | P E | P E | P F | CF |
| 9 | Fumaric acid | P H | P H | P A | CF | P A | CF | P B | P B | P H | CF | P F | CF |
| 10 | Citric acid | P H | P H | P F | CF | P A | CF | P B | CF | AM | CF | P F | CF |
| 11 | (−)-L-Malic acid | PCH | PCH | PCH | PCH | P A | AM | P B | P B | P H | P H | P F | CF |
| 12 | Hippuric acid | P H | CF | P F | CF | P A | CF | P B | CF | P H | CF | INSUFFICENT SOLIDS | |
| 13 | L-Ascorbic acid | P H | CF | P F | CF | P A | CF | P B | P B | P E | CF | P F | CF |
| 14 | Benzoic acid | P F | P F | P F | P F | P A | P A | P B | CF | P E | CF | P F | P F |
| 15 | Succinic acid | P B | CF | P F | CF | P A | CF | P B | CF | P H | CF | P F | CF |
| 16 | Glutaric acid | P H | P H | P F | CF | P A | CF | P B | CF | P H | P H | P F | CF |
| 17 | (+)-Camphoric acid | P B | P B | P F | CF PCH | P A | P B | P B | P B | P E | P E | CF | CF |
| 18 | Nicotinic acid | P B | CF | P F | CF | P A | CF | P B | P B | P E | CF | P F | CF |
| 19 | Orotic acid | AM | CF | AM | CF | P A | CF | P B | CF | P E | CF | P F | CF |
| 20 | L-(+)-Mandelic acid | P B | P B | P F | CF PCH | P A | P B | P B | P E | P E | P E | P F | CF |
| 21 | 2-Aminobenzoic acid | P B | P B | P | CF | P A | CF | P B | P B | P E | P E | P F | CF |
| 22 | Gallic acid | CF | CF | P A | CF | P A | P A | P B | CF | P E | CF | P F | CF |
| 23 | Urea | P H | P H | P F | CF PCH | P H | P B | P B | PB | P H | P H | P F | CF |
| 24 | Caffeine | CF | CF | P F | CF | P A | CF | P B | CF | P E | CF | P H | CF |
| 25 | Nicotinamide | PCH | CF | P F | CF | P A | CF | P B | CF | P E | CF | P F | CF |
| 26 | Isonicotinamide | P B* | P B* | P F | CF | P A | CF | P B | P B | P E | CF | P F | CF |

TABLE 5-continued

Slurry Ripening Results of the Comparative Experiments.[1]

| # | CCF | EtOH | EtOAc | MTBE | MeCN/Water (1:9) | 1-Butanol | Toluene |
|---|---|---|---|---|---|---|---|
| 27 | L-Prolinamide | CHA, CHA | CHA, CHA | CHA, CHA | PB, CF | CHA, CHA | CHA, CHA |
| 28 | Vanillin | AM, AM | PF, CF | PA, PA | PB, CF | PE, CF | PF, CF |
| 29 | Methyl paraben | PB, PB | PF, CF | PA, PA | PB, CF | PE, PE | PF, CF |
| 30 | Propyl paraben | PH, PH | PF, CF | PA, PA | PB, CF | AM, AM | PF, CF |
| 31 | Butylated hydroxyanisole | PH, PH | PF, CF | PA, CF | PB, PB | PE, PE | PF, PF |
| 32 | Pyrogallol | PH, PH | PB, CHA | PA, PCH | PB, PB | AM, AM | PF, CHA |
| 33 | Chrysin | PH, CF | PA, CF | PA, CF | PB, CF | PE, CF | PF, CF |
| 34 | Resveratrol | PH, PH | PF, CF | PA, CF | PB, PB | PE, PE | PF, CF |
| 35 | Quercetin | PCH, CF | PA, CF | PA, CF | PB, CF | PH, PH | PF, CF |
| 36 | Saccharin | PH, CF | PF, CF | PA, CF | PB, CF | PE, CF | PF, CF |
| 37 | Aspartame | CH, CH (A+F) | PA, CF | PA, CF | PB, CF | CF, CHA | PF, CF |
| 38 | Xylitol | PH, CF | PF, CF | PA, CF | PB, CF | PE, CF | PF, CF |
| 39 | Sucralose | PH, PA | PA, CF | PA, CF | PB, CF | PE, CF | PF, CF |
| 40 | D-Mannitol | CF, CF | PA, CF | PA, CF | PB, PB | PE, CF | PF, CF |
| 41 | DL-Mandelic acid | PB, PB | PA, CF | PA, PA | PB, PB | PE, PE | PF, CF |

Legend:
AM: amorphous
P = parent
PCH = poorly crystalline hit
* = poorly crystalline
CH = crystalline hit
CF = coformer
A, B, F, H = crystal forms

[1] In each experiment, a product from the solvent-drop grinding experiment was placed in a 2 mL vials containing a tumble-stir disc and combined with up to 1500 μL of a solvent solution saturated with the respective coformer. Samples were mixed and temperature-cycled between 25° C. and 5° C. for 10 days. Solvent solution was added was added as needed to yield mixable suspensions with sufficient solids for isolation and analysis. Suspended solids were isolated by filtration and air-dried for 18 hours.

TABLE 6

Testing of Forms A-G of Compound 1.

| Form | Coformer | PXRD | DSC Endotherms (Onset, ° C.) | Description |
|---|---|---|---|---|
| A | Citric Acid | Table 7 & FIG. 13 | FIG. 14 47.7 | Poorly crystalline; Likely hydrated and/or solvated |
| B | Nicotinamide | Table 8 & FIG. 21 | FIG. 15 81.7 | Poorly crystalline; Mixture with coformer; Likely hydrated and/or solvated |
| C | Nicotinamide | Table 8 & FIG. 22 | FIG. 16 27.4 80.0 112.2 | Poorly crystalline; Mixture with coformer; Likely hydrated and/or solvated |
| D | 1-Hydroxy-2-Naphthoic acid | Table 7 & FIG. 17 | — | Poorly crystalline |
| E | L-malic acid | Table 7 & FIG. 18 | FIG. 19 29.7 77.9 | Did not crystallize over time; Likely hydrated and/or solvated |
| F | Urea | Table 9 & FIG. 23 | FIG. 20 27.1 71.0 108.2 | Poorly crystalline; Mixture with parent and coformer; Likely hydrated and/or solvated |
| G | Quercetin | Table 9 & FIG. 24 | — | Poorly crystalline; Mixture with coformer |

TABLE 7

Powder X-Ray Diffraction Peaks for Solid Forms A, D, and E of Compound 1.

| Solid Form A | | | Solid Form D | | | Solid Form E | | |
|---|---|---|---|---|---|---|---|---|
| 2Theta (°) | d Space (Å) | Height (counts) | 2Theta (°) | d Space (Å) | Height (counts) | 2Theta (°) | d Space (Å) | Height (counts) |
| 15.3 | 5.793 | 215 | 6.2 | 14.310 | 112 | 3.7 | 24.022 | 610 |
| 18.2 | 4.864 | 303 | 13.3 | 6.672 | 117 | 5.2 | 17.093 | 50 |
| 22.4 | 3.969 | 194 | 21.7 | 4.091 | 131 | 5.9 | 15.055 | 80 |
| 23.2 | 3.836 | 141 | 25.6 | 3.483 | 74 | 10.4 | 8.473 | 54 |
| 26.1 | 3.410 | 149 | 26.1 | 3.410 | 187 | 13.3 | 6.681 | 103 |
| 32.7 | 2.738 | 74 | 28.2 | 3.161 | 55 | 18.2 | 4.882 | 120 |
| | | | 31.2 | 2.866 | 44 | 19.5 | 4.564 | 115 |
| | | | | | | 24.5 | 3.638 | 64 |

TABLE 8

Powder X-Ray Diffraction Peaks for Solid Forms B and C of Compound 1.

| Solid Form B | | | Solid Form C | | |
|---|---|---|---|---|---|
| 2Theta (°) | d Space (Å) | Height (counts) | 2Theta (°) | d Space (Å) | Height (counts) |
| 6.1 | 14.486 | 1978 | 4.2 | 21.222 | 2260 |
| 7.0 | 12.679 | 6663 | 4.5 | 19.466 | 3342 |
| 10.8 | 8.183 | 5024 | 6.4 | 13.882 | 2761 |
| 12.2 | 7.260 | 4623 | 12.4 | 7.144 | 712 |
| 14.8 | 5.975 | 8655 | 14.8 | 5.987 | 1468 |
| 16.2 | 5.467 | 1338 | 19.6 | 4.536 | 600 |
| 18.3 | 4.839 | 3170 | 25.9 | 3.442 | 776 |
| 19.6 | 4.541 | 918 | | | |
| 21.5 | 4.143 | 1455 | | | |
| 22.2 | 3.996 | 1517 | | | |
| 23.7 | 3.756 | 1939 | | | |
| 25.4 | 3.504 | 1545 | | | |
| 25.9 | 3.442 | 3481 | | | |
| 27.3 | 3.261 | 3337 | | | |

TABLE 9

Powder X-Ray Diffraction Peaks for Solid Forms F and G of Compound 1.

| Solid Form F | | | Solid Form G | | |
|---|---|---|---|---|---|
| 2Theta (°) | d Space (Å) | Height (counts) | 2Theta (°) | d Space (Å) | Height (counts) |
| 3.2 | 27.874 | 14074 | 4.6 | 19.376 | 1929 |
| 3.9 | 22.912 | 9415 | 5.6 | 15.883 | 3094 |
| 5.3 | 16.524 | 1321 | 10.1 | 8.746 | 2544 |
| 6.1 | 14.426 | 1895 | 10.9 | 8.125 | 5166 |
| 7.0 | 12.549 | 1945 | 13.6 | 6.509 | 12914 |
| 10.8 | 8.183 | 1458 | 16.5 | 5.381 | 1202 |
| 12.6 | 7.047 | 1748 | 17.9 | 4.959 | 2083 |
| 13.4 | 6.608 | 2065 | 21.8 | 4.073 | 1192 |
| 21.7 | 4.094 | 2739 | 23.3 | 3.811 | 514 |
| 22.3 | 3.978 | 3312 | 24.4 | 3.642 | 488 |
| 23.2 | 3.838 | 881 | 26.1 | 3.413 | 804 |
| 24.7 | 3.609 | 649 | 27.7 | 3.220 | 739 |
| 25.1 | 3.550 | 949 | 29.6 | 3.013 | 728 |
| 26.4 | 3.375 | 948 | | | |
| 27.4 | 3.252 | 566 | | | |
| 29.4 | 3.040 | 433 | | | |

The embodiments disclosed herein are not to be limited in scope by the specific embodiments disclosed in the examples which are intended as illustrations of a few aspects of the disclosed embodiments and any embodiments that are functionally equivalent are encompassed by the present disclosure. Indeed, various modifications of the embodiments disclosed herein are in addition to those shown and described herein will become apparent to those skilled in the art and are intended to fall within the scope of the appended claims.

A number of references have been cited, the disclosures of which are incorporated herein by reference in their entirety.

What is claimed is:

1. A solid form comprising (a) Compound 1:

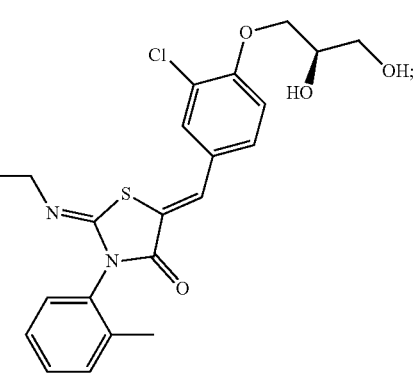

and
(b) a second compound selected from the group consisting of L-prolinamide, pyrogallol, aspartame, citric acid, nicotinamide, 1-hydroxy-2-naphthoic acid, L-malic acid, urea, quercetin, camphoric acid, and L-mandelic acid, wherein:
the second compound is L-prolinamide, and the solid form has an X-ray powder diffraction pattern comprising peaks at 2θ angles of 11.2, 19.4, and 21.4±0.2 2θ as acquired using Cu Kα radiation;
the second compound is pyrogallol, and the solid form has an X-ray powder diffraction pattern comprising peaks at 2θ angles of 7.7, 12.0, and 19.8±0.2 2θ as acquired using Cu Kα radiation;
the second compound is aspartame, and the solid form has an X-ray powder diffraction pattern comprising peaks at 2θ angles of 14.2, 17.7, and 18.7±0.2 2θ as acquired using Cu Kα radiation;
the second compound is citric acid, and the solid form has an X-ray powder diffraction pattern comprising a peak at a 2θ angle of 32.7±0.2 2θ and additional peaks at 2θ angles of 18.2 and 22.4±0.2 2θ as acquired using Cu Kα radiation;
the second compound is nicotinamide, and the solid form has an X-ray powder diffraction pattern comprising a peak at a 2θ angle of 14.8±0.2 2θ as acquired using Cu Kα radiation;

the second compound is 1-hydroxy-2-naphthoic acid, and the solid form has an X-ray powder diffraction pattern comprising peaks at 2θ angles of approximately 21.7 and 31.2±0.2 2θ and an additional peak at a 2θ angle of 13.3±0.2 2θ as acquired using Cu Kα radiation;

the second compound is L-malic acid, and the solid form has an X-ray powder diffraction pattern comprising peaks at 2θ angles of approximately 3.7 and 13.3±0.2 2θ, and an additional peak at a 2θ angle of 10.4±0.2 2θ as acquired using Cu Kα radiation;

the second compound is urea, and the solid form has an X-ray powder diffraction pattern comprising a peak at a 2θ angle of 25.1±0.2 2θ as acquired using Cu Kα radiation; and the second compound is quercetin, and the solid form has an X-ray powder diffraction pattern comprising a peak at a 2θ angle of 13.6±0.2 2θ as acquired using Cu Kα radiation.

2. The solid form of claim 1, comprising (a) Compound 1:

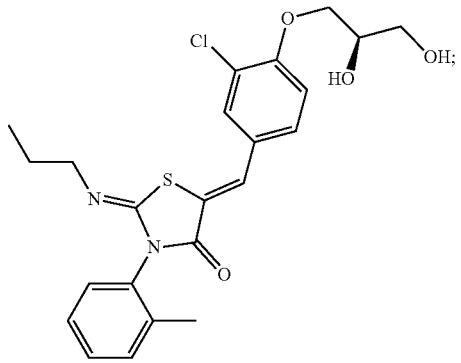

and
(b) L-prolinamide, the solid form having an X-ray powder diffraction pattern comprising peaks at 2θ angles of 11.2, 19.4, and 21.4±0.2 2θ as acquired using Cu Kα radiation.

3. The solid form of claim 1, comprising (a) Compound 1:

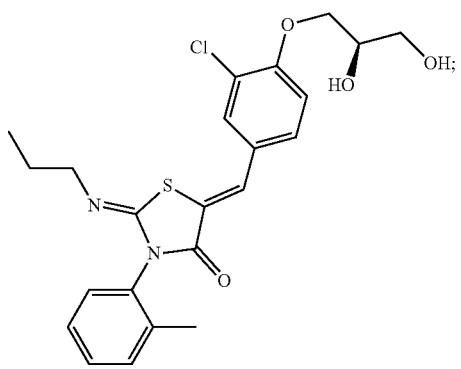

and
(b) pyrogallol, the solid form having an X-ray powder diffraction pattern comprising peaks at 2θ angles of 7.7, 12.0, and 19.8±0.2 2θ as acquired using Cu Kα radiation.

4. The solid form of claim 1, comprising (a) Compound 1:

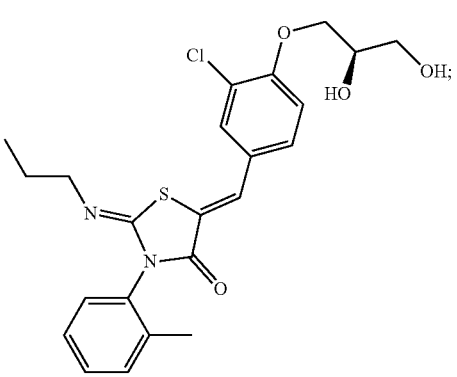

and
(b) aspartame, the solid form having an X-ray powder diffraction pattern comprising peaks at 2θ angles of 14.2, 17.7, and 18.7±0.2 2θ as acquired using Cu Kα radiation.

5. The solid form of claim 1, comprising (a) Compound 1:

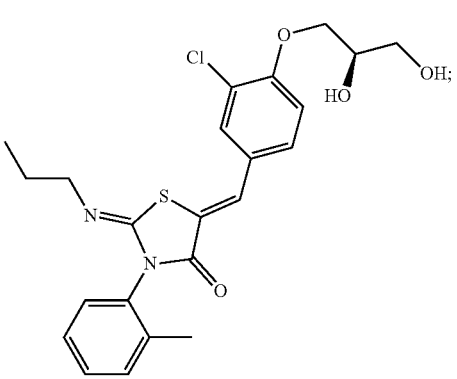

and
(b) citric acid, the solid form having an X-ray powder diffraction pattern comprising a peak at a 2θ angle of 32.7±0.2 2θ and additional peaks at 2θ angles of 18.2 and 22.4±0.2 2θ as acquired using Cu Kα radiation.

6. The solid form of claim 1, comprising (a) Compound 1:

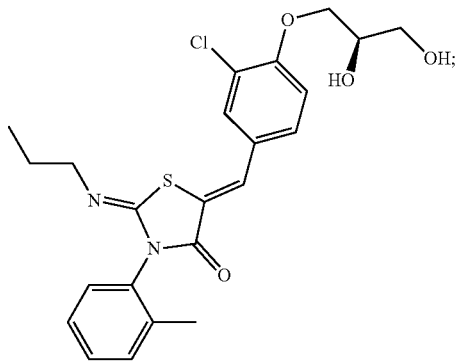

and
(b) nicotinamide, the solid form having an X-ray powder diffraction pattern comprising a peak at a 2θ angle of 14.8±0.2 2θ as acquired using Cu Kα radiation.

7. The solid form of claim 1, comprising (a) Compound 1:

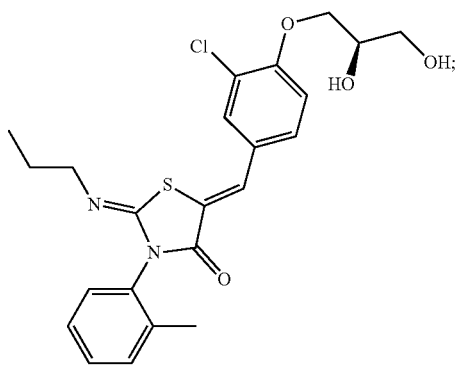

and
(b) 1-hydroxy-2-naphthoic acid, the solid form having an X-ray powder diffraction pattern comprising peaks at 2θ angles of approximately 21.7 and 31.2±0.2 2θ and an additional peak at a 2θ angle of 13.3±0.2 2θ as acquired using Cu Kα radiation.

8. The solid form of claim 1, comprising (a) Compound 1:

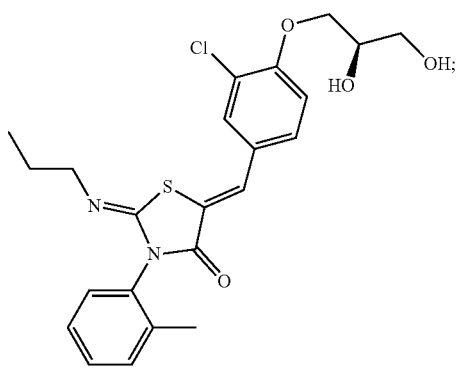

and
(b) L-malic acid, the solid form having an X-ray powder diffraction pattern comprising peaks at 2θ angles of approximately 3.7 and 13.3±0.2 2θ, and an additional peak at a 2θ angle of 10.4±0.2 2θ as acquired using Cu Kα radiation.

9. The solid form of claim 1, comprising (a) Compound 1:

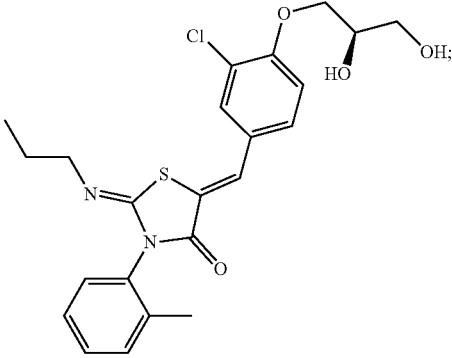

and
(b) urea, the solid form having an X-ray powder diffraction pattern comprising a peak at a 2θ angle of 25.1±0.2 2θ as acquired using Cu Kα radiation.

10. The solid form of claim 1, comprising (a) Compound 1:

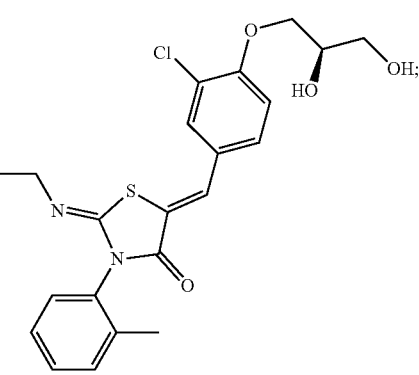

and
(b) quercetin, the solid form having an X-ray powder diffraction pattern comprising a peak at a 2θ angle of 13.6±0.2 2θ as acquired using Cu Kα radiation.

11. The solid form of claim 2, wherein the X-ray powder diffraction pattern further comprises peaks at 2θ angles of 15.2, 16.7, 20.5, 22.9, and 23.8±0.2 2θ as acquired using Cu Kα radiation.

12. The solid form of claim 2, which has a thermogravimetric analysis thermogram comprising a total mass loss of approximately 0.8% when heated from about 25° C. to about 116° C.

13. The solid form of claim 2, which has a differential scanning calorimetry thermogram comprising a melting endotherm with onset at approximately 94.8° C.

14. The solid form of claim 3, wherein the X-ray powder diffraction pattern further comprises peaks at 2θ angles of 9.9, 14.8, 16.1, 26.5, and 28.8±0.2 2θ as acquired using Cu Kα radiation.

15. The solid form of claim 3, which has a thermogravimetric analysis thermogram comprising a total mass loss of approximately 0.1% when heated from about 26° C. to about 120° C.

16. The solid form of claim 3, which has a differential scanning calorimetry thermogram comprising a melting endotherm with onset temperature at approximately 96.4° C.

17. The solid form of claim 4, wherein the X-ray powder diffraction pattern comprises a further peak at 2θ angle of 5.0±0.2 2θ as acquired using Cu Kα radiation.

18. The solid form of claim 17, wherein the X-ray powder diffraction pattern further comprises peaks at 2θ angles of 5.9, 6.2, 6.7, 7.3, 8.1, 11.7, and 12.8±0.2 2θ as acquired using Cu Kα radiation.

19. A method of preparing the solid form of claim 2, comprising solvent-drop grinding or slurry ripening.

20. A method of preparing the solid form of claim 3, comprising slurry ripening.

21. A method of preparing the solid form of claim 4, comprising slurry ripening.

22. A method of preparing the solid form of claim 5, comprising solvent-drop grinding.

23. A method of preparing the solid form of claim 6, comprising solvent-drop grinding or slurry ripening.

24. A method of preparing the solid form of claim 7, comprising slurry ripening.

25. A method of preparing the solid form of claim 8, comprising slurry ripening.

26. A method of preparing the solid form of claim 10, comprising slurry ripening.

27. A pharmaceutical composition comprising the solid form of claim 1.

28. A method of treating multiple sclerosis, wherein the method comprises administering to a patient in need thereof the solid form of claim 1.

29. A method of treating psoriasis, wherein the method comprises administering to a patient in need thereof the solid form of claim 1.

30. A method of treating multiple sclerosis or psoriasis, comprising: administering to a patient in need thereof the solid form of claim 1 in combination with one or several immunomodulating agents, the agents selected from the group consisting of immunosuppressants, corticosteroids, nonsteroidal anti-inflammatory drugs, cytotoxic drugs, adhesion molecule inhibitors, cytokines, cytokine inhibitors, cytokine receptor antagonists and recombinant cytokine receptors.

* * * * *